United States Patent
Lawson et al.

(10) Patent No.: US 11,407,838 B2
(45) Date of Patent: Aug. 9, 2022

(54) ERENUMAB COMPOSITIONS AND USES THEREOF

(71) Applicant: AMGEN INC., Thousand Oaks, CA (US)

(72) Inventors: Kenneth Lawson, Thousand Oaks, CA (US); Noel Rieder, Thousand Oaks, CA (US); Suminda Hapuarachchi, Camarillo, CA (US); Jose Gregorio Ramirez, Providence, RI (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 16/372,291

(22) Filed: Apr. 1, 2019

(65) Prior Publication Data

US 2019/0300617 A1    Oct. 3, 2019

Related U.S. Application Data

(60) Provisional application No. 62/651,651, filed on Apr. 2, 2018.

(51) Int. Cl.

| C07K 16/28 | (2006.01) |
| C07K 16/18 | (2006.01) |
| G01N 30/46 | (2006.01) |
| C07K 16/06 | (2006.01) |
| A61P 25/06 | (2006.01) |
| G01N 30/02 | (2006.01) |

(52) U.S. Cl.
CPC .......... *C07K 16/2869* (2013.01); *A61P 25/06* (2018.01); *C07K 16/065* (2013.01); *C07K 16/18* (2013.01); *G01N 30/463* (2013.01); *C07K 2317/51* (2013.01); *C07K 2317/515* (2013.01); *C07K 2317/90* (2013.01); *G01N 2030/027* (2013.01)

(58) Field of Classification Search
CPC .. C07K 16/2869; C07K 16/18; C07K 16/065; C07K 2317/51; C07K 2317/515; C07K 2317/90; C07K 2317/94; A61P 25/06; G01N 30/463; G01N 2030/027
See application file for complete search history.

(56) References Cited

U.S. PATENT DOCUMENTS

| 5,785,682 | A | 7/1998 | Grabenkort |
| 5,866,124 | A | 2/1999 | Hardman et al. |
| 7,193,070 | B2 | 3/2007 | Kane et al. |
| 7,288,251 | B2 | 10/2007 | Bedian et al. |
| 7,423,128 | B2 | 9/2008 | Gazit-Bornstein et al. |
| 7,658,924 | B2 | 2/2010 | Oliner et al. |
| 9,072,777 | B2 | 7/2015 | Shindo |
| 9,102,731 | B2 | 8/2015 | Boone et al. |
| 9,862,771 | B2 | 1/2018 | Boone et al. |
| 9,896,502 | B2 | 2/2018 | Bigal et al. |
| 10,259,877 | B2 | 4/2019 | Sun et al. |
| 2002/0164707 | A1 | 11/2002 | Adamou et al. |
| 2004/0110170 | A1 | 6/2004 | Pisegna |
| 2004/0132101 | A1 | 7/2004 | Lazar et al. |
| 2004/0176577 | A1 | 9/2004 | Rojer et al. |
| 2005/0282252 | A1 | 12/2005 | Siegel et al. |
| 2006/0018909 | A1 | 1/2006 | Oliner et al. |
| 2006/0246071 | A1 | 11/2006 | Green et al. |
| 2008/0057063 | A1 | 3/2008 | Rinkenberger et al. |
| 2009/0220489 | A1 | 9/2009 | Zeller et al. |
| 2012/0014968 | A1 | 1/2012 | Walsh et al. |
| 2012/0177640 | A1* | 7/2012 | Burg ............... C07K 16/32 424/133.1 |
| 2015/0266948 | A1 | 9/2015 | Bigal et al. |
| 2015/0322142 | A1 | 11/2015 | Bigal et al. |
| 2015/0376286 | A1 | 12/2015 | Boone et al. |
| 2016/0161455 | A1* | 6/2016 | McDonald ........ B01D 15/362 506/9 |
| 2016/0311913 | A1* | 10/2016 | Sun ............... C07K 16/2869 |
| 2017/0306033 | A1 | 10/2017 | Kannan et al. |

FOREIGN PATENT DOCUMENTS

| CN | 101128483 A | 2/2008 |
| JP | 2005-503809 A | 2/2005 |
| JP | 2007-525495 A | 9/2007 |
| WO | 98/03534 A1 | 1/1998 |
| WO | 02/066492 A2 | 8/2002 |
| WO | 2003/027252 A2 | 4/2003 |
| WO | 2004/014351 A2 | 2/2004 |
| WO | 2004/097421 A2 | 11/2004 |
| WO | 2005/077072 A2 | 8/2005 |
| WO | 2006/068953 A2 | 6/2006 |
| WO | 2006/134692 A1 | 12/2006 |

(Continued)

OTHER PUBLICATIONS

Assessment report for Aimovig (non-proprietary name: erenumab) by the European Medicines Agency (EMA), May 31, 2018, 104 pages. (Year: 2018).*
Dillon TM et al. Structural and functional characterization of disulfide isoforms of the human IgG2 subclass. J. Biol. Chem. 2008, 283(23), 16206-16215. (Year: 2008).*
Goswami S et al. Developments and challenges for mAb-based therapeutics. Antibodies, 2013, 2: 452-500. (Year: 2013).*
Khawli LA et al. Charge variants in IgG1: Isolation, characterization, in vitro binding properties and pharmacokinetics in rats. mAbs, 2010, 2(6):613-624. (Year: 2010).*

(Continued)

*Primary Examiner* — Kimberly Ballard

(74) *Attorney, Agent, or Firm* — Angela L. Purcell

(57) ABSTRACT

The present invention relates to compositions comprising erenumab and one or more erenumab variants, including isomerization variants, deamidation variants, acidic variants, and HMW species. Pharmaceutical formulations comprising the erenumab compositions and methods of using and characterizing the compositions are also described.

27 Claims, 24 Drawing Sheets

Specification includes a Sequence Listing.

(56) References Cited

FOREIGN PATENT DOCUMENTS

| | | | |
|---|---|---|---|
| WO | 2007/045927 A2 | 4/2007 | |
| WO | 2007/048026 A2 | 4/2007 | |
| WO | 2007/054809 A2 | 5/2007 | |
| WO | 2007/076336 A1 | 7/2007 | |
| WO | 2008/132453 A1 | 11/2008 | |
| WO | 2009/109908 A1 | 9/2009 | |
| WO | 2010/012911 A1 | 2/2010 | |
| WO | 2010/075238 A1 | 7/2010 | |
| WO | WO-2010102241 A1 * | 9/2010 | ............ C07K 16/18 |
| WO | 2011/024113 A1 | 3/2011 | |
| WO | 2012/162257 A2 | 11/2012 | |
| WO | 2014/144632 A2 | 9/2014 | |
| WO | 2016/044224 A1 | 3/2016 | |
| WO | 2016/171742 A1 | 10/2016 | |

OTHER PUBLICATIONS

Sydow JF et al. Structure-based prediction of asparagine and aspartate degradation sites in antibody variable regions. PLoS ONE, 2014, 9(6):e100736. (Year: 2014).*
Almagro and Fransson (2008), "Humanization of antibodies", Frontiers Biosci. 13:1619-1633.
De Hoon et al. (2015), "Single-dose and multiple dose, phase I, randomized, double-blind, placebo-controlled studies of AMG 334 in healthy subject and migraine patients", 57$^{th}$ Ann. Sci. Mtg., Am. Headache Soc., Washington D.C., Headache, vol. 55 (suppl. S3), 174-175, Abstract PS35, Jun. 17, 2015.
Vu et al. (2015), "Characterizing the relationship between AMG 334 concentration and capsaicin-induced increase in dermal blood flow in healthy subjects and migraine patients using pharmacokinetic-pharmacodynamic modeling", 57$^{th}$ Ann. Sci. Mtg., Am. Headache Soc., Washington D.C., Headache, vol. 55 (suppl. S3), 175-176, Abstract PS37, Jun. 17, 2015.
Ashina et al. (1999), "Plasma levels of substance P, neuropeptide Y and vasoactive intestinal polypeptide in patients with chronic tension-type headache". Pain, 83:541-547.
Ashina et al. (2000), "Plasma levels of calcitonin gene-related peptide in chronic tension-type headache", Neurol. 55(9):1335-1340.
Bendig, M. M. (1995). Humanization of rodent monoclonal antibodies by CDR grafting. Methods-Companion to Methods in Enzymology, 8(2), 83-93.
Bennett et al. (2000), "Alleviation of mechanical and thermal allodynia by CGRP8-37 in a rodent model of chronic central pain", Pain, 86(1-2): 163-175.
Berglund et al. (2008), "The epitope space of the human proteome", Protein Sci., 17:606-613.
Bigal and Walter (2014), "Monoclonal antibodies for migraine: preventing calcitonin gene-related peptide activity," CNS Drugs, 28:389-399.
Calcitonin receptor-like [Homo sapiens], NCBI Ref. Seq.: NP 005786.1 (Feb. 3, 2008).
Chauhan, M. et al. (2004), "Studies on the effects of the N-terminal domain antibodies of calcitonin receptor-like receptor and receptor activity-modifying protein 1 on calcitonin gene-related peptide-induced vasorelaxation in rat uterine artery", Biol.Reproduction, 70:1658-1663.
Colman, P.M. (1994), "Effects of amino acid sequence changes on antibody-antigen interactions", Research in Immunology, 145:33-36.
Committee on Methods of Producing Monoclonal Antibodies (1999), "Monoclonal antibody production", National Academy Press, Washington DC.
Corvera, Carlos U. et al. (2005), "Localization of calcitonin receptor-like receptor (CLR) and calcitonin gene-related peptide (CGRP) in human gut", Database Biosis, Ann. Mtg. Amer. Gastroenterol, Assoc./Digestive Disease Wk., Chicago, IL, 128(4, S2):A361.
Cottrell et al. (2005), "Localization of calcitonin receptor-like receptor and receptor activity modifying protein 1 in enteric neuron, dorsal root ganglia and the spinal cord of the rat", J. Comparative Neurol, 490:239-255.
Davis et al. (2008), "The tortuous road to an ideal CGRP function blocker for the treatment of migraine", Current Topics in Med. Chem., 8(16)1468-1479.
Deng et al. (2012), "Monoclonal antibodies: what are the pharmacokinetic and pharmacodynamic considerations for drug development?", Expert Opin. Drug Metab. Toxicol., 8(2):141-160.
Dong, Yuan-Lin et al. (2004), "Involvement of calcitonin gene-related peptide in control of human fetoplacental vascular tone", Amer. J. Physiol. Heart Circulation Physiol., 286:H230-H239.
Durham et al. (2004), "CGRP-receptor antagonists—a fresh approach to migraine therapy?", N. Eng. J. Med., 350(11):1073-1075.
Durham, Paul L. (2008), "Inhibition of calcitonin gene-related peptide function: a promising strategy for treating migraine", Headache, 48:1269-1275.
Edvinsson, Lars and HO, Tony W. (2010), "CGRP receptor antagonism and migraine", Neurotherap., 7(2):164-175.
Evans et al. (2000), "CGRP-RCP, a novel protein required for signal transduction at calcitonin gene-related peptide and adrenomedullin receptors", 275(40):31438-31443.
Goadsby et al. (1990), "Vasoactive peptide release in the extracerebral circulation of humans during migraine headache", Ann. Neurol., 28:183-187.
Goadsby et al. (2017), "A controlled trial of erenumab for episodic migraine", N. Engl. J. Med., 377(22):2123-2132.
Greenspan et al. (1999), "Defining epitopes: It's not as easy as it seems", Nature Biotech., 17:936-937.
Hay, D.L. (2007), "What makes a CGRP$_2$ receptor?", Clin. Exper. Pharmacol. Physiol., 34:963-971, doi:10.1111/j.1440-1681.2007.04703.x.
The International Classification of Headache Disorders, 2nd ed. (2004), Cephalalgia, 24(Suppl. 1):9-160.
Jiang et al. (2005), "A novel peptide isolated from a phage display peptide library with trastuzumab can mimic antigen epitope of HER-2*", J. Biol. Chem., 280(6):4656-4662.
Kuwasako et al. (2000), "Visualization of the calcitonin receptor-like receptor and its receptor activity-modifying proteins during internalization and recycling", J. Biol. Chem., 275(28):29602-29609.
Lennerz et al. (2008), "Calcitonin receptor-like receptor (CLR), receptor activity-modifying protein 1 (Ramp1), and calcitonin gene-related peptide (CGRP) immunoreactivity in the rat trigeminovascular system: differences between peripheral and central CGRP receptor distribution", J. Comparative Neurol., 507(3):1277-1299.
Mach et al. (2002), "Origins of skeletal pain: sensory and sympathetic innervation for the mouse femur", Neurosci., 113(1):155-166.
McAllister, Peter (Mar. 7, 2015), "CGRP Research in 2015: Where are we now and where are we going?" The 25th Annual Headache Symposium, HCNE Headache Cooperative of New England, Presentation.
McLatchie, L.M. et al. (1998), "RAMPs regulate the transport and ligand specificity of the calcitonin-receptor-like receptor", Nature, 393:333-339.
Paul, William E. (1993), "Fv structure and diversity in three dimensions", Fundamental Immunology, 3$^{rd}$ ed., pp. 292-295.
Perena, M.J. et al. (2000), "Neuroanatomia del dolor", Rev. Soc. Esp. Dolor, 7(Supl II): 5-10.
Perena, M.J. et al. (2000), "Neuroanatomia del dolor", Rev. Soc. Esp. Dolor, 7(Supl II): 5-10. * Machine Translation into English.
Poyner et al. (2002), "International union of pharmacology, XXXII. The mammalian calcitonin gene-related peptides, adrenomedullin, amylin, and calcitonin receptors", Pharmacol. Rev., 54(2).
Receptor activity-modifying protein 1 precursor [Homo sapiens] NCBI Ref. Seq.: NP 005846.1 (Feb. 3, 2008).
Rudikoff, Stuart et al. (1982), "Single amino acid substitution altering antigen-binding specificity", PNAS USA, 79(6):1979-1983.
Stancoviski et al. (1991), "Mechanistic aspects of the opposing effects of monoclonal antibodies to the ERBB2 receptor on tumor growth", PNAS USA, 88:8691-8695.
Taylor, Christopher K. et al. (2006), "Pharmacological characterization of novel α-calcitonin gene related peptide (CGRP) receptor peptide antagonists that are selective for human CGRP receptors", J. Pharmacol. Exper. Therap., 319(2):749-757.

(56) References Cited

OTHER PUBLICATIONS

Tepper et al. (2017), "Safety and efficacy of erenumab for preventive treatment of chronic migraine: a randomised, double-blind, placebo-controlled phase 2 trial", Lancet Neurol., 16:425-434.

Vecsei, Laszlo et al. (2015), "CGRP antagonists and antibodies for the treatment of migraine", Expert Opin. Invest. Drugs, 24(1):31-41.

Walker and Hay (2013), "CGRP in the trigeminovascular system: a role for CGRP, adrenomedullin and amylin receptors?", British J. of Pharmacol., 170:1293-1307.

Walter, Sarah and Bigal, Marcelo E. (2015), "TEV-48125: A review of a monoclonal CGRP antibody in development for the preventive treatment of migraine", Curr. Pain Headache Rep., 19(6):1-6.

Wang, W. et al. (2008), "Monoclonal antibody pharmacokinetics and pharmacodynamics", Clin. Pharmacol. Therap., 84(5):548-558.

Wimalawansa et al. (1989), "Isolation, purification and raising of monoclonal antibodies for calcitonin gene-related peptide (CGRP) receptor", Reg. Peptides, 26(1).

Wyon et al. (2000), "Concentrations of calcitonin gene-related peptide and neuropeptide Y in plasma increase during flushes in postmenopausal women", Menopause, 7(1):25-30.

Zeller, J. et al. (2008), "CGRP function-blocking antibodies inhibit neurogenic vasodilatation without affecting heart rate or arterial blood pressure in the rat", British J. Pharmacol., 155(7):1093-1103.

Yasuo Ito and Nobuo Araki (2014), "Kakusyu Yakuzai no Jyozu na Tsukaikata, Henzutu Chiryoyaku (Migraine-Abortive Agents, Selection and Quality Use of Medicine)", Rinsyo to Kenkyu (JP J. Clin. & Exper. Medicine), 91(3):365-370.

Koichi Shibata (2014), "Henzutsu Yobo Ryoho (Migraine Prevention Therapy)", Saishin Igaku (Medical Frontline), 69(6):1130-1136.

International Search Report for PCT/US2019/025223 dated Aug. 2, 2019.

Notice of Rejection (English Translation) for Japanese Appl. No. 2018-154482 dated Jul. 2, 2019.

Wagner-Rousset et al. (2017), "Development of a fast workflow to screen the charge variants of therapeutic antibodies", J. Chromatography A, 1498:147-154.

Written Opinion for PCT/US2019/025223 dated Aug. 2, 2019.

Booe et al. (2015), "Structural Basis for Receptor Activity-Modifying Protein-Dependent Selective Peptide Recognition by a G Protein-Coupled Receptor", Molecular Cell, 58:1040-1052.

Demaagd et al. (2008), "The Pharmacological Management of Migraine, Part 1; Overview of Abortive Therapy", Pharmacy and Therapeutics, 33 (7): 404-416.

Demaagd, George (2008), "The pharmacological management of migraine, part 2, preventative therapy", Pharm. Therap., 33(8):480-487.

Irimia et al. (2011), "Refractory migraine in a headache clinic population", BMC Neurol., 11(94):1-6.

Khantasup et al. (2015), "Design and generation of humanized single-chain Fv derived from mouse hybridoma for potential targeting application", Monoclonal Antibodies in Immunodiagnosis & Immunotherapy, 34(6):404-417.

Marquez de Prado and Russo (2006), "CGRP receptor antagonists: a new frontier of anti-migraine medications", Drug Disc. Today: Therap. Strat., 3(4):593-597.

Olesen et al. (2004), "Calcitonin gene-related peptide receptor antagonist BIBN 4096 BS for the acute treatment of migraine", N. Engl. J. Med., 350:1104-1110.

Vulto and Jaquez (2017), "The process defines the product: what really matters in biosimilar design and production?", Rheumatology, 56:iv14-iv29.

Du et al., "Chromatographic analysis of the acidic and basic species of recombinant monoclonal antibodies", mAbs, vol. 4 (5), pp. 578-585 (2012).

Wang et al., "Antibody structure, instability, and formulation," J. Pharm. Sci., vol. 96 (1), pp. 1-26 (2007).

Ashina et al. (2018), "Efficacy and safety of erenumab (AMG334) in chronic migraine patients with prior preventive treatment failure: A subgroup analysis of a randomized, double-blind, placebo-controlled study", Cephalalgia, vol. 38(10): 1611-1621.

Barbanti et al. (2021), "Long-term (48 weeks) effectiveness, safety, and tolerability of erenumab in the prevention of high-frequency episodic and chronic migraine in a real world: Results of the Early 2 study", Headache, 1-13, doi: 10.1111/head.14194, EPub ahead of print.

Goadsby et al. (2019), "Efficacy and safety of erenumab (AMG334) in episodic migraine patients with prior preventive treatment failure: A subgroup analysis of a randomized, double-blind, placebo-controlled study", Cephalalgia, vol. 39(7): 817-826.

Katsarava et al. (2012), "Defining the differences between episodic migraine and chronic migraine", Curr. Pain Headache Rep., 16:86-92.

Schulman (2013), "Refractory Migraine—A Review", Headache, vol. 53: 599-613.

\* cited by examiner

Amino Acid Sequence of Erenumab Heavy Chain

```
1    QVQLVESGGG VVQPGRSLRL SCAASGFTFS SFGMHWVRQA PGKGLEWVAV
51   ISFDGSIKYS VDSVKGRFTI SRDNSKNTLF LQMNSLRAED TAVYYCARDR
101  LNYYDSSGYY HYKYYGMAVW GQGTTVTVSS ASTKGPSVFP LAPCSRSTSE
151  STAALGCLVK DYFPEPVTVS WNSGALTSGV HTFPAVLQSS GLYSLSSVVT
201  VPSSNFGTQT YTCNVDHKPS NTKVDKTVER KCCVECPPCP APPVAGPSVF
251  LFPPKPKDTL MISRTPEVTC VVVDVSHEDP EVQFNWYVDG VEVHNAKTKP
301  REEQFNSTFR VVSVLTVVHQ DWLNGKEYKC KVSNKGLPAP IEKTISKTKG
351  QPREPQVYTL PPSREEMTKN QVSLTCLVKG FYPSDIAVEW ESNGQPENNY
401  KTTPPMLDSD GSFFLYSKLT VDKSRWQQGN VFSCSVMHEA LHNHYTQKSL
451  SLSPGK (SEQ ID NO: 1)
```

FIG. 1A

Amino Acid Sequence of Erenumab Light Chain

```
1    QSVLTQPPSV SAAPGQKVTI SCSGSSSNIG NNYVSWYQQL PGTAPKLLIY
51   DNNKRPSGIP DRFSGSKSGT STTLGITGLQ TGDEADYYCG TWDSRLSAVV
101  FGGGTKLTVL GQPKANPTVT LFPPSSEELQ ANKATLVCLI SDFYPGAVTV
151  AWKADGSPVK AGVETTKPSK QSNNKYAASS YLSLTPEQWK SHRSYSCQVT
201  HEGSTVEKTV APTECS (SEQ ID NO: 2)
```

FIG. 1B

Erenumab Heavy Chain Sequence with Post-Translational Modifications

```
1    pEVQLVESGGG VVQPGRSLRL SCAASGFTFS SFGMHWVRQA PGKGLEWVAV
51   ISFDGSIKYS VDSVKGRFTI SRDNSKNTLF LQMNSLRAED TAVYYCARDR
101  LNYYDSSGYY HYKYYGMAVW GQGTTVTVSS ASTKGPSVFP LAPCSRSTSE
151  STAALGCLVK DYFPEPVTVS WNSGALTSGV HTFPAVLQSS GLYSLSSVVT
201  VPSSNFGTQT YTCNVDHKPS NTKVDKTVER KCCVECPPCP APPVAGPSVF
251  LFPPKPKDTL MISRTPEVTC VVVDVSHEDP EVQFNWYVDG VEVHNAKTKP
301  REEQFNSTFR VVSVLTVVHQ DWLNGKEYKC KVSNKGLPAP IEKTISKTKG
351  QPREPQVYTL PPSREEMTKN QVSLTCLVKG FYPSDIAVEW ESNGQPENNY
401  KTTPPMLDSD GSFFLYSKLT VDKSRWQQGN VFSCSVMHEA LHNHYTQKSL
451  SLSPG (SEQ ID NO: 3)
```

FIG. 1C

Erenumab Light Chain Sequence with Post-Translational Modifications

```
1    pESVLTQPPSV SAAPGQKVTI SCSGSSSNIG NNYVSWYQQL PGTAPKLLIY
51   DNNKRPSGIP DRFSGSKSGT STTLGITGLQ TGDEADYYCG TWDSRLSAVV
101  FGGGTKLTVL GQPKANPTVT LFPPSSEELQ ANKATLVCLI SDFYPGAVTV
151  AWKADGSPVK AGVETTKPSK QSNNKYAASS YLSLTPEQWK SHRSYSCQVT
201  HEGSTVEKTV APTECS (SEQ ID NO: 4)
```

FIG. 1D

Amino Acid Sequence of Erenumab Heavy Chain Variable Region

```
1    QVQLVESGGG VVQPGRSLRL SCAASGFTFS SFGMHWVRQA PGKGLEWVAV
51   ISFDGSIKYS VDSVKGRFTI SRDNSKNTLF LQMNSLRAED TAVYYCARDR
101  LNYYDSSGYY HYKYYGMAVW GQGTTVTVSS (SEQ ID NO: 5)
```

FIG. 1E

Amino Acid Sequence of Erenumab Light Chain Variable Region

```
1    QSVLTQPPSV SAAPGQKVTI SCSGSSSNIG NNYVSWYQQL PGTAPKLLIY
51   DNNKRPSGIP DRFSGSKSGT STTLGITGLQ TGDEADYYCG TWDSRLSAVV
101  FGGGTKLTVL (SEQ ID NO: 6)
```

FIG. 1F

SEQUENCE LISTING

```
<160> NUMBER OF SEQ ID NOS: 6

<210> SEQ ID NO 1
<211> LENGTH: 456
<212> TYPE: PRT
<213> ORGANISM: Artificial Sequence
<220> FEATURE:
<223> OTHER INFORMATION: Synthetic polypeptide

<400> SEQUENCE: 1

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Val Ile Ser Phe Asp Gly Ser Ile Lys Tyr Ser Val Asp Ser Val
    50                  55                  60
```

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
             85                  90                  95

Ala Arg Asp Arg Leu Asn Tyr Tyr Asp Ser Ser Gly Tyr Tyr His Tyr
            100                 105                 110

Lys Tyr Tyr Gly Met Ala Val Trp Gly Gln Gly Thr Thr Val Thr Val
        115                 120                 125

Ser Ser Ala Ser Thr Lys Gly Pro Ser Val Phe Pro Leu Ala Pro Cys
130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Asn Phe Gly Thr
        195                 200                 205

Gln Thr Tyr Thr Cys Asn Val Asp His Lys Pro Ser Asn Thr Lys Val
210                 215                 220

Asp Lys Thr Val Glu Arg Lys Cys Cys Val Glu Cys Pro Pro Cys Pro
225                 230                 235                 240

Ala Pro Pro Val Ala Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Gln Phe Asn Trp Tyr Val
        275                 280                 285

Asp Gly Val Glu Val His Asn Ala Lys Thr Lys Pro Arg Glu Glu Gln
290                 295                 300

Phe Asn Ser Thr Phe Arg Val Val Ser Val Leu Thr Val His Gln
305                 310                 315                 320

Asp Trp Leu Asn Gly Lys Glu Tyr Lys Cys Lys Val Ser Asn Lys Gly
                325                 330                 335

Leu Pro Ala Pro Ile Glu Lys Thr Ile Ser Lys Thr Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Met Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
450                 455

<210> SEQ ID NO 2
<211> LENGTH: 216
<212> TYPE: PRT

<213> ORGANISM: Artificial Sequence
<220> FEATURE:
<223> OTHER INFORMATION: Synthetic polypeptide

<400> SEQUENCE: 2

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
50                  55                  60

Gly Ser Lys Ser Gly Thr Ser Thr Thr Leu Gly Ile Thr Gly Leu Gln
65                  70                  75                  80

Thr Gly Asp Glu Ala Asp Tyr Tyr Cys Gly Thr Trp Asp Ser Arg Leu
                85                  90                  95

Ser Ala Val Val Phe Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
        210                 215
```

<210> SEQ ID NO 3
<211> LENGTH: 455
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: pyroglutamate residue

<400> SEQUENCE: 3

```
Xaa Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Val Ile Ser Phe Asp Gly Ser Ile Lys Tyr Ser Val Asp Ser Val
50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95
```

Ala Arg Asp Arg Leu Asn Tyr Tyr Asp Ser Ser Gly Tyr Tyr His Tyr
            100                 105                 110

Lys Tyr Tyr Gly Met Ala Val Trp Gly Gln Gly Thr Thr Val Thr Val
            115                 120                 125

Ser Ser Ala Ser Thr Lys Gly Pro Ser Val Phe Pro Leu Ala Pro Cys
        130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Asn Phe Gly Thr
        195                 200                 205

Gln Thr Tyr Thr Cys Asn Val Asp His Lys Pro Ser Asn Thr Lys Val
210                 215                 220

Asp Lys Thr Val Glu Arg Lys Cys Cys Val Glu Cys Pro Pro Cys Pro
225                 230                 235                 240

Ala Pro Pro Val Ala Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Gln Phe Asn Trp Tyr Val
        275                 280                 285

Asp Gly Val Glu Val His Asn Ala Lys Thr Lys Pro Arg Glu Glu Gln
290                 295                 300

Phe Asn Ser Thr Phe Arg Val Val Ser Val Leu Thr Val Val His Gln
305                 310                 315                 320

Asp Trp Leu Asn Gly Lys Glu Tyr Lys Cys Lys Val Ser Asn Lys Gly
                325                 330                 335

Leu Pro Ala Pro Ile Glu Lys Thr Ile Ser Lys Thr Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Met Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly
    450                 455

<210> SEQ ID NO 4
<211> LENGTH: 216
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES

```
<222> LOCATION: (1)..(1)
<223> OTHER INFORMATION: pyroglutamate residue

<400> SEQUENCE: 4

Xaa Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
    50                  55                  60

Gly Ser Lys Ser Gly Thr Ser Thr Leu Gly Ile Thr Gly Leu Gln
65                  70                  75                  80

Thr Gly Asp Glu Ala Asp Tyr Tyr Cys Gly Thr Trp Asp Ser Arg Leu
                85                  90                  95

Ser Ala Val Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
            210                 215

<210> SEQ ID NO 5
<211> LENGTH: 130
<212> TYPE: PRT
<213> ORGANISM: Artificial Sequence
<220> FEATURE:
<223> OTHER INFORMATION: Synthetic polypeptide

<400> SEQUENCE: 5

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
            35                  40                  45

Ala Val Ile Ser Phe Asp Gly Ser Ile Lys Tyr Ser Val Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Arg Leu Asn Tyr Tyr Asp Ser Ser Gly Tyr Tyr His Tyr
            100                 105                 110

Lys Tyr Tyr Gly Met Ala Val Trp Gly Gln Gly Thr Thr Val Thr Val
```

```
<210> SEQ ID NO 6
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 6

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Thr Thr Leu Gly Ile Thr Gly Leu Gln
65                  70                  75                  80

Thr Gly Asp Glu Ala Asp Tyr Tyr Cys Gly Thr Trp Asp Ser Arg Leu
                85                  90                  95

Ser Ala Val Val Phe Gly Gly Gly Thr Lys Leu Thr Val Leu
                100                 105                 110
```

ERENUMAB COMPOSITIONS AND USES THEREOF

CROSS-REFERENCE TO RELATED APPLICATIONS

This application claims the benefit of U.S. Provisional Application No. 62/651,651, filed Apr. 2, 2018, which is hereby incorporated by reference in its entirety.

DESCRIPTION OF THE TEXT FILE SUBMITTED ELECTRONICALLY

The present application contains a Sequence Listing, which has been submitted electronically in ASCII format and is hereby incorporated by reference in its entirety. The computer readable format copy of the Sequence Listing, which was created on Mar. 7, 2019, is named A-2190-US-NP_SeqList_ST25 and is 15 kilobytes in size.

FIELD OF THE INVENTION

The present invention relates to the field of biopharmaceuticals. In particular, the invention relates to the identification and characterization of variants of erenumab that impact the functional activity of erenumab. The invention also relates to compositions comprising erenumab and one or more erenumab variants, pharmaceutical formulations comprising the compositions, and methods of using and characterizing the compositions.

BACKGROUND OF THE INVENTION

Erenumab is a fully human monoclonal antibody that specifically binds to the human calcitonin gene-related peptide (CGRP) receptor and prevents the CGRP ligand from binding to and activating the receptor. CGRP has been implicated in migraine pathogenesis (Durham, New England Journal of Medicine, Vol. 350: 1073-1075, 2004; Edvinsson et al., Neurotherapeutics, Vol. 7: 164-175, 2010). In phase 2 and phase 3 clinical trials, patients with chronic or episodic migraine treated with erenumab experienced a reduction in the number of monthly migraine days as compared to patients receiving placebo (Tepper et al., Lancet Neurol., Vol. 16: 425-434, 2017; Goadsby et al., New England Journal of Medicine, Vol. 377: 2123-2132, 2017).

Complex therapeutic biologics, such as monoclonal antibodies, can have numerous product quality attributes that may impact the safety and/or efficacy of the biologic. A comprehensive structural and functional assessment of the molecule is typically required to identify such attributes and understand their impact on the properties of the molecule. An understanding of a molecule's attributes is important to ensure production of a consistent product.

Variants of the biologic can arise during the manufacturing process or under storage conditions. Such product variants can be categorized as product-related substances or product-related impurities. Product-related substances are those molecular variants of the desired product formed during manufacture or storage of the product which have properties comparable to those of the desired product, and are not considered impurities. Conversely, product-related impurities are molecular variants of the desired product, which do not have properties comparable to those of the desired product with respect to product efficacy and patient safety. Thus, identification and characterization of product-related impurities in particular is useful for the manufacture and quality control of the biologic drug product.

SUMMARY OF THE INVENTION

The present invention is based, in part, on the identification and characterization of product-related impurities of erenumab, particularly variants of erenumab that have reduced functional activity. Control and monitoring of the amounts of these variants in therapeutic erenumab compositions ensures that the erenumab compositions have the requisite potency to produce the desired clinical effects. Accordingly, in some embodiments, the present invention provides an erenumab composition comprising erenumab and one or more erenumab variants, wherein the erenumab variants comprise isomerization variants, deamidation variants, acidic variants, disulfide isoform variants, high molecular weight (HMW) species, or combinations thereof, wherein the amounts of the erenumab variants in the composition are controlled to within specific ranges.

In certain embodiments, the invention provides compositions comprising erenumab and one or more erenumab variants, wherein the one or more erenumab variants comprises an isomerization variant and a deamidation variant. In some embodiments, the isomerization variant has an isoaspartic acid residue or succinimide at amino acid position 105 in either or both heavy chains (SEQ ID NO: 1 or SEQ ID NO: 3) of erenumab. In these and other embodiments, the deamidation variant has the asparagine residue at amino acid position 102 in either or both heavy chains (SEQ ID NO: 1 or SEQ ID NO: 3) of erenumab converted to an aspartic acid residue, a succinimide, or an isoaspartic acid residue. The amount of the isomerization variant and deamidation variant in the composition can be less than about 30%, less than about 15%, less than about 8%, or less than about 4%, for example, as determined by hydrophobic interaction chromatography high performance liquid chromatography (HIC-HPLC).

The invention also provides compositions of erenumab and one or more acidic variants of erenumab. The amount of acidic variants in the composition can be less than about 40%, for example, from about 25% to about 38% or from about 26% to about 34%. In some embodiments, the amount of acidic variants in the erenumab compositions is determined by cation exchange high performance liquid chromatography (CEX-HPLC). Acidic variants of erenumab include disulfide isoform variants, deamidation variants, fragmentation variants, non-consensus glycosylation variants, HMW species, and combinations thereof. In certain embodiments, the acidic variants comprise disulfide isoform variants, fragmentation variants, or combinations thereof.

In some embodiments, the present invention provides compositions of erenumab and disulfide isoform variants of erenumab. The disulfide isoform variants of erenumab can comprise an IgG2-B isoform and/or an IgG2-AB isoform. The amount of the IgG2-B isoform in the composition can be less than about 20%, for example, less than about 10%, or less than about 8%, such as from about 4% to about 6%. The amount of the IgG2-AB isoform in the composition can be from about 20% to about 40%, from about 26% to about 38%, or from about 34% to about 37%. In certain embodiments, the amount of the disulfide isoforms is determined by non-reduced reversed phase high performance liquid chromatography (RP-HPLC).

The invention also includes compositions comprising erenumab and one or more size variants of erenumab, such as low molecular weight (LMW) species, middle molecular weight (MMW) species, and high molecular weight (HMW) species. In certain embodiments, the amount of HMW species in the composition is less than about 3.0%, for example, about 2.5% or less, about 2.1% or less, about 1.8% or less, about 1.4% or less, or about 1.2% or less. In one particular embodiment, the HMW species of erenumab is comprised predominantly of a covalently-linked dimer of erenumab. The amount of HMW species in the erenumab compositions can be determined by size exclusion ultra-high performance liquid chromatography (SE-UHPLC).

In some embodiments, the present invention also provides methods of evaluating or assessing the quality of erenumab compositions. In one embodiment, the methods comprise obtaining an erenumab composition that contains erenumab and one or more erenumab variants; measuring the amount of one or more erenumab variants in the composition; comparing the measured amount of the one or more erenumab variants to a pre-determined reference criterion; and preparing a pharmaceutical formulation or pharmaceutical product of the erenumab composition if the comparison indicates that the pre-determined reference criterion is met. The methods may comprise one, two, or three of the following: (1) measuring the amount of isomerization variants and deamidation variants in the composition (e.g. by peak area percentage of the pre-peaks in HIC-HPLC), (2) measuring the amount of acidic variants in the composition (e.g. by peak area percentage of the acidic peaks in CEX-HPLC), and/or (3) measuring the amount of HMW species in the composition (e.g. by peak area percentage of the pre-peaks in SE-UHPLC). In certain embodiments, all three measurements are performed on an erenumab composition.

Pharmaceutical formulations comprising the erenumab compositions described herein are also included in the invention. In some embodiments, the pharmaceutical formulations comprise an erenumab composition described herein and one or more pharmaceutically acceptable excipients, such as buffers, sugars, and surfactants. The pharmaceutical formulations can be incorporated into an injection device, such as a pre-filled syringe or autoinjector. In such embodiments, the injection volume for the pre-filled syringes or autoinjectors is less than about 2 mL, for example, about 1 mL.

The present invention also includes methods of treating, preventing, or reducing the occurrence of headache in a patient in need thereof using the erenumab compositions and pharmaceutical formulations of the invention. In one embodiment, the methods comprise administering to the patient a pharmaceutical formulation comprising an erenumab composition described herein. The headache can be a migraine headache, cluster headache, or other type of headache disorder, such as tension-type headache, hemiplegic migraine, menstrual migraine, and retinal migraine. In certain embodiments, the patient to be treated according to the methods or uses of the invention has or is diagnosed with migraine, such as episodic migraine or chronic migraine.

The use of the erenumab compositions in any of the methods disclosed herein or for preparation of medicaments for administration according to any of the methods disclosed herein is specifically contemplated. For instance, the present invention includes an erenumab composition or pharmaceutical formulation described herein for use in a method for treating, preventing, or reducing the occurrence of headache in a patient in need thereof. The present invention also encompasses the use of an erenumab composition or pharmaceutical formulation described herein in the preparation of a medicament for treating, preventing, or reducing the occurrence of headache in a patient in need thereof.

BRIEF DESCRIPTION OF THE DRAWINGS

FIGS. 1A and 1B show the amino acid sequences of the heavy chain (FIG. 1A; SEQ ID NO: 1) and light chain (FIG. 1B; SEQ ID NO: 2) for erenumab. Complementarity determining regions (CDRs) in each chain are bolded and underlined. The heavy chain contains an N-linked glycosylation site at the asparagine residue at position 306.

FIGS. 1C and 1D show the amino acid sequences of the heavy chain (FIG. 1C; SEQ ID NO: 3) and light chain (FIG. 1D; SEQ ID NO: 4) with common post-translational modifications at the N- and C-termini for erenumab. CDRs in each chain are bolded and underlined. pE represents pyroglutamate.

FIGS. 1E and 1F show the amino acid sequences of the heavy chain variable region (FIG. 1E; SEQ ID NO: 5) and light chain variable region (FIG. 1F; SEQ ID NO: 6) for erenumab. CDRs in each variable region are bolded and underlined.

FIGS. 3A-3G, respectively) were analyzed by HIC-HPLC using a sodium acetate pH 5.5 mobile phase with elution by a linear decreasing gradient of ammonium sulfate and detection at 280 nm absorbance. Each figure is a plot of absorbance at 280 nm versus elution time in minutes. An overlay of all seven HIC-HPLC fractions with erenumab drug substance is shown in FIG. 3H.

FIGS. 12A-12I, respectively) were analyzed by CEX-HPLC using a sodium phosphate pH 6.6 mobile phase with elution by a linear gradient of sodium chloride and detection at 280 nm absorbance. Each figure is a plot of absorbance at 280 nm versus elution time in minutes.

FIGS. 18A-18C, respectively) were analyzed by SE-UHPLC using a 100 mM sodium phosphate, 250 mM sodium chloride, pH 6.8 mobile phase and detection at 280 nm absorbance. Each figure is a plot of absorbance at 280 nm versus elution time in minutes for each fraction overlaid on the SE-UHPLC profile for erenumab drug substance. An overlay of all three SE-UHPLC fractions with erenumab drug substance is shown in FIG. 18D.

DETAILED DESCRIPTION

Figure 2A:
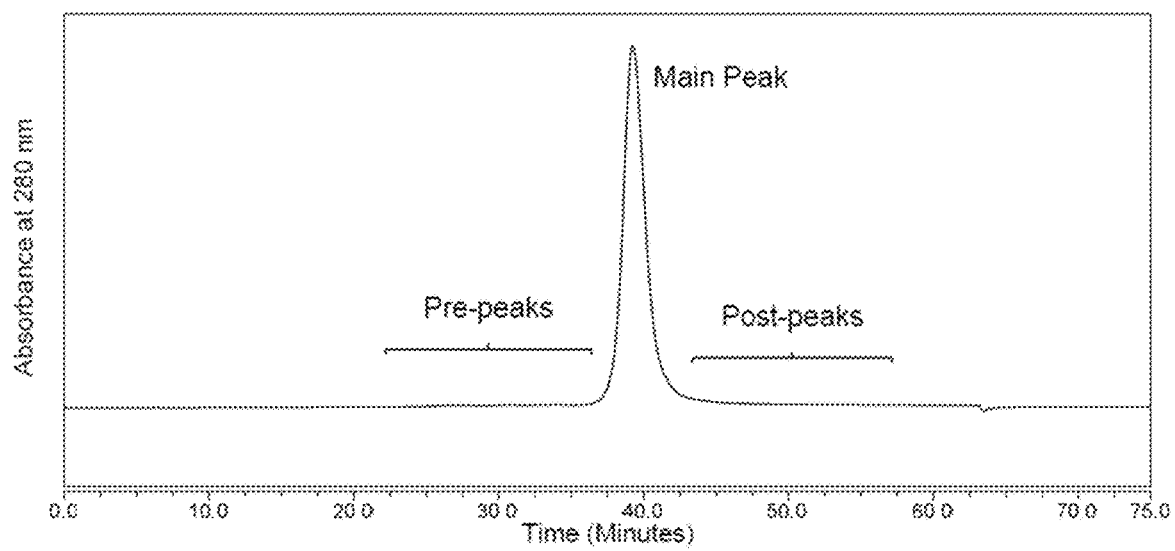
FIGS. 2A and 2B depict a representative HIC-HPLC profile of erenumab drug substance at full scale (FIG. 2A) and expanded scale (FIG. 2B). Erenumab drug substance was analyzed by HIC-HPLC using a sodium acetate pH 5.5 mobile phase with elution by a linear decreasing gradient of ammonium sulfate and detection at 280 nm absorbance.

The present invention relates to the identification and characterization of variants of erenumab that exhibit reduced functional activity. In particular, variants of erenumab having certain structural modifications are much less potent than erenumab in blocking CGRP receptor activation by the CGRP ligand. Such variants, each of which is described in more detail herein, include isomerization variants, deamidation variants, disulfide isoform variants, acidic variants, and HMW species. By limiting the amount of these variants in erenumab drug substance and erenumab drug product, the overall potency of erenumab compositions can be maintained or matched to the erenumab compositions employed during clinical trials and observed to have clinical efficacy. Accordingly, the present invention provides compositions comprising erenumab and one or more erenumab variants, wherein the amounts of the erenumab variants in the composition are controlled to within specific ranges or limits as described herein.

The term erenumab refers to an IgG2 antibody comprising the heavy chain variable region sequence of SEQ ID NO: 5 and the light chain variable region sequence of SEQ ID NO: 6. In one embodiment, erenumab comprises a heavy chain comprising the sequence of SEQ ID NO: 1 and a light chain comprising the sequence of SEQ ID NO: 2. In such embodiments, erenumab is an antibody comprising two heavy chains and two light chains, wherein each of the heavy chains comprises the sequence of SEQ ID NO: 1 and each of the light chains comprises the sequence of SEQ ID NO: 2. When produced recombinantly, erenumab can undergo common post-translational modifications at the termini of the heavy and light chains, such as removal of the C-terminal lysine residue at position 456 from the heavy chain and cyclization of the N-terminal glutamine residues in the light and heavy chains to pyroglutamate. Thus, the term erenumab can also refer to an IgG2 antibody that lacks the C-terminal lysine residue in one or both of the heavy chains and/or comprises a pyroglutamate residue as the N-terminal residue in place of the glutamine residue in one or both of the light chains and/or one or both of the heavy chains. For instance, in some embodiments, erenumab is an antibody comprising two heavy chains and two light chains, wherein each of the heavy chains comprises the sequence of SEQ ID NO: 3 and each of the light chains comprises the sequence of SEQ ID NO: 4. In other embodiments, erenumab is an antibody comprising two heavy chains and two light chains, wherein each of the heavy chains comprises the sequence of SEQ ID NO: 1 or SEQ ID NO: 3 and each of the light chains comprises the sequence of SEQ ID NO: 2 or SEQ ID NO: 4.

In certain embodiments, an erenumab variant present in the compositions of the invention is a charge variant. A charge variant refers to a variant of erenumab that has a different charge profile resulting from, inter alia, post-translational modifications that directly alter the net charge of the antibody, induce conformational changes, or affect local charge distribution. Such post translational modifications can include deamidation, isomerization, glycation, oxidation, and sialylated glycosylation. Charge variants can be separated from erenumab and detected using ion exchange chromatography, reversed phase chromatography, or hydrophobic interaction chromatography. Charge variants of erenumab can include, but are not limited to, isomerization variants, deamidation variants, disulfide isoform variants, acidic variants, and glycosylation variants.

In some embodiments, the charge variant of erenumab is an isomerization variant. An isomerization variant of erenumab refers to a variant of erenumab in which one or more aspartic acid residues in the heavy chain polypeptide or light chain polypeptide is converted to isoaspartic acid or succinimide. In one embodiment, an isomerization variant of erenumab has an isoaspartic acid residue or succinimide at amino acid position 105 in either or both heavy chains (SEQ ID NO: 1 or SEQ ID NO: 3) of erenumab. As described in Example 1, conversion of the aspartic acid residue at position 105 in CDR3 of the heavy chain variable region to isoaspartate significantly reduces the inhibitory potency of erenuamb.

In other embodiments, the charge variant of erenumab is a deamidation variant. A deamidation variant of erenumab refers to a variant of erenumab in which one or more asparagine residues in the heavy chain polypeptide or light chain polypeptide is converted to an aspartic acid, which in turn can be converted to succinimide or isoaspartic acid. In one embodiment, the deamidation variant has the asparagine residue at amino acid position 102 in either or both heavy chains (SEQ ID NO: 1 or SEQ ID NO: 3) of erenumab converted to aspartic acid, succinimide, or isoaspartic acid. As described in Example 1, deamidation of the asparagine residue at position 102 in CDR3 of the heavy chain variable region significantly reduces the inhibitory potency of erenumab. In another embodiment, the deamidation variant has the asparagine residue at amino acid position 393 and/or 398 in either or both heavy chains of erenumab converted to aspartic acid, succinimide, or isoaspartic acid.

Methods of detecting and quantitating the isomerization variants and deamidation variants of erenumab include hydrophobic interaction chromatography, such as the hydrophobic interaction chromatography high performance liquid chromatography (HIC-HPLC) method described in Example 1, peptide mapping, such as the ESI-MS/MS peptide mapping method described in Example 1, ion exchange chromatography, such as the cation exchange high performance liquid chromatography (CEX-HPLC) method described in Example 3, reversed phase high performance liquid chromatography (RP-HPLC), and other methods known to those of skill in the art, such as those described in Kameoka et al., Journal of Biochemistry, Vol. 134: 129-135, 2003; Zhang et al., Journal of Pharmaceutical and Biomedical Analysis, Vol. 30: 1479-1490, 2003; Yang et al., Electrophoresis, Vol. 31: 1764-1772, 2010; Faseri et al., Journal of Chromatography A, Vol. 1498: 215-223, 2017; and Leblanc et al., Journal of Chromatography B, Vol. 1048: 130-139, 2017.

The compositions of the invention comprise controlled amounts of isomerization variants and deamidation variants of erenumab such that the overall potency of the erenumab compositions is maintained at a level observed to have clinical efficacy. See Examples 1 and 2. For instance, in certain embodiments, the present invention provides a composition comprising erenumab and one or more erenumab variants, wherein the one or more erenumab variants comprises an isomerization variant and a deamidation variant, and wherein the amount of the isomerization variant and deamidation variant in the composition is less than about 30%. The amount of the isomerization variant and deamidation variant in the composition can be less than about 25%, less than about 20%, less than about 17%, less than about 15%, less than about 12%, less than about 10%, less than about 8%, less than about 6%, or less than about 4%. In one embodiment, the amount of the isomerization variant and deamidation variant in the composition is less than about 15%. In another embodiment, the amount of the isomerization variant and deamidation variant in the composition is less than about 8%. In yet another embodiment, the amount of the isomerization variant and deamidation variant in the composition is less than about 4%. In some embodiments, the amount of the isomerization variant and deamidation variant in the composition can be from about 0.5% to about 30%, from about 1% to about 20%, from about 1% to about 17%, from about 1% to about 15%, from about 1% to about 12%, from about 1% to about 10%, from about 0.5% to about 8%, from about 0.5% to about 6%, from about 1% to about 4%, from about 0.5% to about 3.5%, from about 1.5% to about 2.5%, or from about 1.7% to about 2.1%. In one embodiment, the amount of the isomerization variant and deamidation variant in the composition is from about 1% to about 10%. In another embodiment, the amount of the isomerization variant and deamidation variant in the composition is from about 1% to about 4%. In yet another embodiment, the amount of the isomerization variant and deamidation variant in the composition is from about 0.5% to about 3.5%.

The amount of erenumab isomerization and deamidation variants in the compositions of the invention can be determined by any of the methods described above for detecting and quantitating these variants. In certain embodiments, the amount of the isomerization variant and deamidation variant in the composition is determined by HIC-HPLC. The isomerization variants (e.g. isomerization of Asp105 in the heavy chain) and deamidation variants (e.g. deamidation of Asn102 in the heavy chain) are the predominant species in the pre-peak fractions of HIC-HPLC. See Examples 1 and 2. Thus, the amount of these variants in an erenumab composition can be determined from the peak area percentage of the pre-peaks in a HIC-HPLC chromatogram. The pre-peaks in a HIC-HPLC chromatogram refer to the peaks with a peak height above the limit of detection that have retention times shorter than the retention time for the main peak, which is typically the peak in the chromatogram with the greatest peak height. See FIGS. 2A, 2B, 5, 7, and 8. The main peak corresponds to erenumab (e.g. antibody comprising two heavy chains having the sequence of SEQ ID NO: 1 or 3 and two light chains having the sequence of SEQ ID NO: 2 or 4), which is the major form of the antibody molecule in the composition. The peak area percentage of the pre-peaks can be calculated according to the following formula:

$$\% \text{ Pre-Peaks} = \frac{\text{Pre-Peaks Area}}{\text{Total integrated peak area}} \times 100,$$

where the total integrated peak area is the combined area for all peaks in the chromatogram with a peak height above the limit of detection. Similarly, the peak area percentage of the main peak can be calculated according to the following formula:

$$\% \text{ Main peak} = \frac{\text{Main peak area}}{\text{Total integrated peak area}} \times 100,$$

where the total integrated peak area is the combined area for all peaks in the chromatogram with a peak height above the limit of detection. In some embodiments, the HIC-HPLC method is conducted as described in Example 1.

In certain embodiments, the amount of isomerization variants (e.g. isomerization of Asp105 in the heavy chain) and deamidation variants (e.g. deamidation of Asn102 in the heavy chain) in a composition of the invention is about 15% or less as measured by the pre-peaks in HIC-HPLC. In one embodiment, the amount of isomerization variants and deamidation variants in the composition is about 10% or less as measured by the pre-peaks in HIC-HPLC. In another embodiment, the amount of isomerization variants and deamidation variants in the composition is about 8% or less as measured by the pre-peaks in HIC-HPLC. In another embodiment, the amount of isomerization variants and deamidation variants in the composition is about 6% or less as measured by the pre-peaks in HIC-HPLC. In yet another embodiment, the amount of isomerization variants and deamidation variants in the composition is about 4% or less as measured by the pre-peaks in HIC-HPLC. In still another embodiment, the amount of isomerization variants and deamidation variants in the composition is about 3.2% or less as measured by the pre-peaks in HIC-HPLC. In another embodiment, the amount of isomerization variants and deamidation variants in the composition is about 2.7% or less as measured by the pre-peaks in HIC-HPLC. In some embodiments, the amount of isomerization variants and deamidation variants in the composition is from about 1% to about 10% as measured by the pre-peaks in HIC-HPLC. In other embodiments, the amount of isomerization variants and deamidation variants in the composition is from about 1% to about 4% as measured by the pre-peaks in HIC-HPLC. In still other embodiments, the amount of isomerization variants and deamidation variants in the composition is from about 0.5% to about 3.5% as measured by the pre-peaks in HIC-HPLC.

In some embodiments, a composition of the invention comprises erenumab and one or more erenumab variants, wherein the erenumab variants comprise isomerization variants and deamidation variants, and wherein:

(i) the amount of erenumab in the composition is about 90% or greater, about 92% or greater, about 93.9% or greater, about 94.4% or greater, about 96.2% or greater, about 96.8% or greater, or about 97.3% or greater as measured by the main peak in HIC-HPLC; and (ii) the amount of isomerization variants and deamidation variants in the composition is about 10% or less, about 8% or less, about 6.1% or less, about 5.6% or less, about 3.8% or less, about 3.2% or less, or about 2.7% or less as measured by the pre-peaks in HIC-HPLC.

In one embodiment, the amount of erenumab in the composition is about 92% or greater as measured by the main peak in HIC-HPLC, and the amount of isomerization variants and deamidation variants in the composition is about 8% or less as measured by the pre-peaks in HIC-HPLC. In another embodiment, the amount of erenumab in the composition is about 96.8% or greater as measured by the main peak in HIC-HPLC, and the amount of isomerization variants and deamidation variants in the composition is about 3.2% or less as measured by the pre-peaks in HIC-HPLC. In yet another embodiment, the amount of erenumab in the composition is about 97.3% or greater as measured by the main peak in HIC-HPLC, and the amount of isomerization variants and deamidation variants in the composition is about 2.7% or less as measured by the pre-peaks in HIC-HPLC. In these and other embodiments, the HIC-HPLC is conducted as described in Example 1 and the amounts are determined from the peak area percentage for the main peak and pre-peaks.

As described in Example 2, the isomerization of Asp105 in the heavy chain CDR3 was highly sensitive to forced thermal stress conditions, and deamidation in both the heavy chain CDR3 (Asn102) and Fc region (Asn393 and Asn398) increased when exposed to elevated pH (e.g. pH 7.4 or higher). Thus, generation of isomerization and deamidation variants of erenumab can be controlled during the manufacturing process and storage by limiting exposure times of erenumab compositions to temperatures above room temperature and to basic solutions, e.g. solutions with pH above 7.0. For instance, in some embodiments, in-process pool holds or storage of erenumab compositions are kept at room temperature for no more than 14 days. In other embodiments, long-term storage of erenumab compositions is conducted at temperatures below 15° C., for example between 2° C. to 8° C. Isomerization variants and deamidation variants of erenumab can also be removed from erenumab compositions through purification processes, such as hydrophobic interaction chromatography or ion exchange chromatography. Both isomerization and deamidation variants of erenumab elute earlier than erenumab in HIC, and thus these variants can be removed from an erenumab composition by collecting and discarding these earlier eluting fractions. Deamidation variants of erenumab generally have more of a negative charge than erenumab and therefore, will elute earlier than erenumab in cation exchange chromatography or will elute later than erenumab in anion exchange chromatography. Thus, the more acidic deamidation variants can be removed from erenumab compositions by appropriately timing the collection of fractions eluting from a cation exchange or anion exchange resin.

In certain embodiments, the charge variant of erenumab in the compositions of the invention is an acidic variant. An acidic variant refers to a variant of erenumab that has gained negative charge or lost positive charge, or has an altered surface charge profile due to conformational changes, and thus has more acidic character relative to erenumab. Acidic variants of erenumab exhibit reduced inhibitory potency as compared to erenumab. See Example 3 and Table 14. Acidic variants can be separated from erenumab, detected, and quantitated using any method that separates proteins based on charge characteristics, such as isoelectric focusing gel electrophoresis, capillary isoelectric focusing gel electrophoresis, cation exchange chromatography (CEX) and anion exchange chromatography (AEX). When analyzed by ion exchange chromatography, acidic variants can be identified by their retention times relative to the main peak, which corresponds to erenumab. For instance, acidic variants elute earlier than the main peak from CEX—that is, acidic variants have retention times shorter than the retention time for the main peak in CEX. When using AEX, acidic variants elute later then than the main peak and thus have retention times longer than the retention time for the main peak in AEX.

In some embodiments, the present invention provides compositions comprising controlled amounts of acidic variants of erenumab such that the overall potency of the erenumab compositions is maintained at a level observed to have clinical efficacy. See Example 3. Accordingly, in certain embodiments, the present invention provides a composition comprising erenumab and one or more erenumab acidic variants, wherein the amount of the acidic variants in the composition is less than about 40%. The amount of acidic variants in the composition can be less than about 38%, less than about 37%, less than about 36%, less than about 35%, less than about 34%, less than about 33%, less than about 32%, less than about 31%, less than about 30%, less than about 29%, less than about 28%, less than about 27%, or less than about 26%. In one embodiment, the amount of acidic variants in the composition is less than about 38%. In another embodiment, the amount of acidic variants in the composition is less than about 35%. In yet another embodiment, the amount of acidic variants in the composition is less than about 32%. In still another embodiment, the amount of acidic variants in the composition is less than about 30%. In some embodiments, the amount of acidic variants in the composition can be from about 20% to about 40%, from about 25% to about 38%, from about 24% to about 35%, from about 28.5% to about 37.5%, from about 26% to about 34%, from about 28% to about 32%, from about 32.5% to about 37.5%, from about 28.7% to about 31.3%, or from about 26.5% to about 33.6%. In one embodiment, the amount of acidic variants in the composition is from about 25% to about 38%. In another embodiment, the amount of acidic variants in the composition is from about 26% to about 34%. In yet another embodiment, the amount of acidic variants in the composition is from about 28% to about 32%.

The amount of acidic variants of erenumab in the compositions of the invention can be determined by any of the methods described above for detecting and quantitating these variants. In certain embodiments, the amount of acidic variants in the composition is determined by ion exchange chromatography. In one particular embodiment, the amount of acidic variants in the composition is determined by CEX-HPLC, such as the method described in Example 3. Acidic variants of erenumab elute earlier than erenumab (main peak) when separated by CEX, and basic variants of erenumab elute later than erenumab (main peak). See FIG. 11. The amount of acidic variants in an erenumab composition can be determined from the peak area percentage of the acidic peaks in a CEX-HPLC chromatogram. The acidic peaks are those peaks with a peak height above the limit of detection that have retention times shorter than the retention time for the main peak. The basic peaks are those peaks with a peak height above the limit of detection that have retention times longer than the retention time for the main peak. The peak area percentage for the desired component (e.g. acidic peaks, main peak, or basic peaks) can be calculated by dividing the peak area for the desired component (e.g. acidic peaks, main peak, or basic peaks) by the total integrated peak area and multiplying the result by 100. In certain embodiments, the CEX-HPLC method is conducted as described in Example 3.

In some embodiments, a composition of the invention comprises erenumab and one or more erenumab variants, wherein the erenumab variants comprise acidic variants, and the amount of acidic variants in the composition is about 40% or less, about 38% or less, about 36% or less, about 35% or less, about 34% or less, or about 32% or less as measured by the acidic peaks in CEX-HPLC. In one embodiment, the amount of acidic variants in the composition is from about 25% to about 38% as measured by the acidic peaks in CEX-HPLC. In another embodiment, the amount of acidic variants in the composition is from about 26% to about 34% as measured by the acidic peaks in CEX-HPLC. In yet another embodiment, the amount of acidic variants in the composition is from about 26.5% to about 33.6% as measured by the acidic peaks in CEX-HPLC. In still another embodiment, the amount of acidic variants in the composition is from about 28.7% to about 31.3% as measured by the acidic peaks in CEX-HPLC. In another embodiment, the amount of acidic variants in the composition is from about 32.5% to about 37.5% as measured by the acidic peaks in CEX-HPLC. In these and other embodiments, the CEX-HPLC is conducted as described in Example 3 and the amounts of acidic variants are determined from the peak area percentage for the acidic peaks.

The acidic variants can include disulfide isoform variants, deamidation variants, fragmentation variants, non-consensus glycosylation variants, high molecular weight (HMW) species, and combinations thereof. In certain embodiments, the acidic variants comprise disulfide isoform variants (described in more detail herein), fragmentation variants, or combinations thereof. As described in Example 3, acidic fractions enriched in fragmentation variants or disulfide isoform variants, particularly the IgG2-B disulfide isoform, exhibit reduced potency as compared to erenumab.

In some embodiments, the acidic variants comprise fragmentation variants. Fragmentation variants can be formed by hydrolysis of peptide bonds, resulting in cleavage of the light chain polypeptide and/or heavy chain polypeptide. Therefore, fragmentation variants of erenumab refer to fragments of erenumab light chain (SEQ ID NO: 2 or 4) or fragments of erenumab heavy chain (SEQ ID NO: 1 or 3) that consist of fewer amino acids than the full-length chains. Fragmentation variants can be measured using reduced capillary electrophoresis with sodium dodecyl sulfate (rCE-SDS), such as the rCE-SDS method described in Example 3, which resolves these fragmented variants as low molecular weight (LMW) and middle molecular weight (MMW) species. LMW species of erenumab are fragments that have a molecular weight less than that of intact erenumab light chain, which has a molecular weight of about 22,790 Da. MMW species of erenumab are fragments that have a molecular weight greater than that of intact erenumab light chain, but less than that of intact erenumab heavy chain, which has a molecular weight of about 50,165 Da (deglycosylated). Upon separation with rCE-SDS, LMW species of erenumab migrate prior to the erenumab light chain peak and MMW species of erenumab migrate between the erenumab light chain peak and the erenumab heavy chain peak. See, e.g., FIG. 19.

The amount of acidic variants in erenumab compositions can be reduced using chromatographic methods that separate proteins based on charge characteristics, such as ion exchange chromatography, hydrophobic interaction chromatography, or mixed mode chromatography. See, e.g., the methods described in U.S. Pat. Nos. 8,946,395; 9,067,990; 9,249,218; and 9,346,879. As described above, acidic variants of erenumab elute earlier than erenumab (main peak) upon separation by cation exchange chromatography. Thus, acidic variants can be collected and discarded prior to elution of the erenumab main peak or collection of erenumab fractions can be started following elution of the acidic variants. When separated by anion exchange chromatography, acidic variants of erenumab elute later than erenumab (main peak) and thus acidic variants can be reduced or removed from an erenumab composition by stopping collection of erenumab fractions before the elution of the acidic variants.

In certain embodiments, the acidic variants comprise disulfide isoform variants. IgG2 antibodies can exhibit different structural isoforms based on the arrangement of disulfide bonds in the hinge region. In the classical disulfide isoform, known as IgG2-A, the Fab arms are not linked via disulfide bonds to the hinge region and the four cysteine residues in the hinge region (e.g. C232, C233, C236, and C239 of SEQ ID NO: 1 or 3) of one heavy chain each form a disulfide bond with the corresponding cysteine residue in the hinge region of the other heavy chain. See FIG. 15A. A disulfide isoform variant refers to a variant of an IgG2 antibody that has a different disulfide bond connectivity than that found in the classical IgG2-A isoform. In some embodiments, the disulfide isoform variant is an IgG2-B isoform. In the IgG2-B isoform structure, both Fab arms are linked to the hinge region by one or more cysteine residues in the hinge region forming disulfide bonds with cysteine residues in the heavy chain constant CH1 region and/or the light chain constant CL region. See FIG. 15C. For instance, in one embodiment, the IgG2-B isoform comprises the following disulfide bond connectivity between a first heavy chain (HC1), a first light chain (LC1), a second heavy chain (HC2), and a second light chain (LC2) with amino acid positions relative to SEQ ID NO: 1 or 3 for the heavy chains and SEQ ID NO: 2 or 4 for the light chains:

C232 of HC1 to C157 of HC2

C233 of HC1 to C215 of LC1

C232 of HC2 to C157 of HC1

C233 of HC2 to C215 of LC2

C236 of HC1 to C236 of HC2

C239 of HC1 to C239 of HC2

In other embodiments, the disulfide isoform variant is an IgG2-AB isoform. In the IgG2-A/B isoform structure, only one Fab arm is linked to the hinge region by one or more cysteine residues in the hinge region forming disulfide bonds with cysteine residues in the heavy chain constant CH1 region and/or the light chain constant CL region. See FIG. 15B. In one embodiment, the IgG2-AB isoform comprises the following disulfide bond connectivity between HC1, LC1, HC2, and LC2 with amino acid positions relative to SEQ ID NO: 1 or 3 for the heavy chains and SEQ ID NO: 2 or 4 for the light chains:

C232 of HC1 to C157 of HC2

C232 of HC2 to C215 of LC2

C233 of HC1 to C233 of HC2

C236 of HC1 to C236 of HC2

C239 of HC1 to C239 of HC2

The present invention includes compositions comprising erenumab and one or more disulfide isoform variants thereof. The disulfide isoform variants may comprise IgG2-B isoforms, IgG2-AB isoforms, or combinations of the two. In some embodiments, the composition comprises erenumab and one or more disulfide isoform variants thereof, wherein the one or more disulfide isoform variants comprise an IgG2-B isoform, and wherein the amount of the IgG2-B isoform in the composition is less than about 20%. The amount of the IgG2-B isoform in the composition may be less than about 18%, less than about 16%, less than about 14%, less than about 12%, less than about 10%, less than about 9%, less than about 8%, less than about 7%, or less than about 6%. In one embodiment, the amount of the IgG2-B isoform in the composition is less than about 10%. In another embodiment, the amount of the IgG2-B isoform in the composition is less than about 8%. In certain embodiments, the amount of the IgG2-B isoform in the composition can be from about 0.5% to about 20%, from about 1% to about 16%, from about 3% to about 12%, from about 0.5% to about 8%, from about 1% to about 6%, from about 4% to about 6%, from about 4.4% to about 5.9%, or from about 4.6% to about 5.2%. In one embodiment, the amount of the IgG2-B isoform in the composition is from about 0.5% to about 8%. In another embodiment, the amount of the IgG2-B isoform in the composition is from about 4% to about 6%.

In certain embodiments, the compositions of the invention comprise erenumab and one or more disulfide isoform variants thereof, wherein the one or more disulfide isoform variants comprise an IgG2-AB isoform. The amount of the IgG2-AB isoform in the composition can be from about 10% to about 56%, from about 20% to about 40%, from about 26% to about 38%, from about 27% to about 32%, from about 32% to about 38%, from about 34% to about 37%, or from about 34.2% to about 35.5%. In one embodiment, the amount of the IgG2-AB isoform in the composition is from about 32% to about 38%. In another embodiment, the amount of the IgG2-AB isoform in the composition is from about 34% to about 37%.

In some embodiments, the compositions of the invention comprise an erenumab IgG2-A isoform, an erenumab IgG2-AB isoform, and an erenumab IgG2-B isoform, wherein:

(i) the amount of the IgG2-A isoform in the composition is from about 50% to about 70%, from about 52% to about 66%, from about 56% to about 60%, or from about 57.4% to about 59.3%

(ii) the amount of the IgG2-AB isoform in the composition is from about 26% to about 38%, from about 32% to about 38%, from about 34% to about 37%, or from about 34.2% to 35.5%; and (iii) the amount of the IgG2-B isoform in the composition is from about 3% to about 12%, from about 1% to about 10%, from about 4% to about 8%, or from about 4.6% to about 5.2%.

Methods of detecting and quantifying disulfide isoforms include non-reduced reversed phase high performance liquid chromatography (RP-HPLC), such as the RP-HPLC method described in Examples 3 and 4 and in Wypych et al., Journal of Biological Chemistry, Vol. 283(23):16194-16205, 2008; peptide mapping, such as the Lys-C peptide mapping method described in Example 4; and mass spectrometry-based methods, such as those described in Zhang et al., Anal Chem., Vol. 82(3):1090-1099, 2010 and Zhang et al., Biochemistry, Vol. 54: 1956-1962, 2015. In certain embodiments, the amount of disulfide isoforms (e.g. IgG2-A, IgG2-A/B, and IgG2-B) in the compositions of the invention are determined by non-reduced RP-HPLC, optionally by using the peak area percentages for each of the isoforms on a RP-HPLC profile (see, e.g., FIG. 16A).

The proportion of disulfide isoforms can be altered by exposing compositions comprising the different isoforms to reduction-oxidation (redox) agents alone or in combination with chaotropic agents using methods described in Dillon et al., Journal of Biological Chemistry, Vol. 283(23):16206-16215, 2008, PCT Publication No. WO 2006/047340, or PCT Publication No. WO 2006/060083, all of which are hereby incorporated by reference. For instance, the proportion of IgG2-A isoforms can be increased by exposing compositions comprising the different isoforms to redox agents (e.g. cysteine/cystine or glutathione/oxidized glutathione) and chaotropic agents (e.g. guanidine hydrochloride). Thus, in some embodiments, the amount of IgG2-B isoforms of erenumab, which are significantly less potent than the IgG2-AB and IgG2-A isoforms, can be reduced or eliminated from the compositions by exposing the compositions to redox agents in combination with chaotropic agents, optionally according to the methods described in Dillon et al., 2008; WO 2006/047340; or WO 2006/060083.

In certain embodiments, an erenumab variant present in the compositions of the invention is a size variant. A size variant of erenumab refers to a variant that has either a lower molecular weight than erenumab monomer or a higher molecular weight than erenumab monomer. As used herein, the term erenumab monomer refers to an intact antibody comprising two heavy chains and two light chains and the monomer has a molecular weight of about 146,194 Da when measuring deglycosylated heavy and light chains without N- or C-terminal modifications. Size variants include fragmentation variants, such as LMW species and MMW species described above, as well as high molecular weight (HMW) species. BMW species of erenumab refer to species that have a molecular weight that is greater than erenumab monomer. HMW species can include dimers, multimers, and other aggregate forms of erenumab that are formed through covalent and non-covalent self-association. In some embodiments, the HMW species of erenumab comprises a covalently-linked dimer of erenumab (i.e. two covalently-linked erenumab monomers). In certain embodiments, the covalently-linked erenumab dimer is a reducible dimer with the dimer reducing to individual heavy and light chains under reducing and denaturing conditions.

Methods of detecting and quantitating size variants of erenumab include size exclusion chromatography, such as the size exclusion ultra-high performance liquid chromatography (SE-UHPLC) method described in Example 5, capillary electrophoresis with sodium dodecyl sulfate (CE-SDS) performed under reducing or non-reducing conditions, such as the rCE-SDS and nrCE-SDS methods described in Example 3, sedimentation velocity ultracentrifugation, and SE-HPLC with static light scattering detection to determine molar mass.

Fractions enriched in HMW species are considerably less potent in inhibiting ligand-induced activation of the CGRP receptor as compared to erenumab. See Example 5 and Table 26. Thus, the present invention provides erenumab compositions containing controlled amounts of HMW species such that the overall potency of the erenumab compositions is maintained at a level observed to have clinical efficacy. In some embodiments, the compositions of the invention comprise erenumab and a BMW species of erenumab, wherein the amount of the HMW species in the composition is less than about 3.0%. The amount of HMW species in the composition can be about 2.5% or less, about 2.4% or less, about 2.3% or less, about 2.2% or less, about 2.1% or less, about 2.0% or less, about 1.8% or less, about 1.6% or less, about 1.4% or less, about 1.2% or less, about 1.0% or less, about 0.8% or less, about 0.6% or less, or about 0.4% or less. In one embodiment, the amount of HMW species in the composition is about 1.8% or less. In another embodiment, the amount of HMW species in the composition is about 1.4% or less. In yet another embodiment, the amount of HMW species in the composition is about 1.2% or less. In still another embodiment, the amount of HMW species in the composition is about 0.6% or less. In some embodiments, the amount of HMW species in the composition can be from about 0.3% to about 2.4%, from about 0.4% to about 1.2%, from about 0.6% to about 2.1%, from about 0.3% to about 1.8%, from about 1.0% to about 1.6%, or from about 0.6% to about 1.4%. In one embodiment, the amount of HMW species in the composition is from about 0.4% to about 1.2%. In another embodiment, the amount of HMW species in the composition is from about 0.6% to about 2.1%.

The amount of size variants in the compositions of the invention can be determined by any of the methods described above for detecting and quantitating these variants. In certain embodiments, the amount of size variants (e.g. HMW species) is determined by SE-UHPLC. HMW species of erenumab elute earlier than the erenumab monomer (main peak) in SE-UHPLC and thus correspond to pre-peaks in the SE-UHPLC chromatogram, whereas LMW and MMW species elute later than erenumab monomer and thus correspond to the post-peaks in the SE-UHPLC chromatogram. See Example 5 and FIGS. 17A and 17B. Accordingly, the amount of these size variants in an erenumab composition can be determined from the peak area percentage of the pre-peaks (HMW species) or post-peaks (LMW and MMW species) in a SE-UHPLC chromatogram. In some embodiments, the SE-UHPLC method is conducted as described in Example 5.

In certain embodiments, a composition of the invention comprises erenumab and one or more erenumab size variants, wherein the erenumab size variants comprise HMW species of erenumab, and wherein:
(i) the amount of erenumab in the composition is about 97.5% or greater, about 97.9% or greater, about 98.2% or greater, about 98.4% or greater, about 98.6% or greater, about 98.8% or greater, about 99.2% or greater, or about 99.4% or greater as measured by the main peak in SE-UHPLC; and
(ii) the amount of HMW species in the composition is about 2.5% or less, about 2.1% or less, about 1.8% or less, about 1.6% or less, about 1.4% or less, about 1.2% or less, about 0.8% or less, or about 0.6% or less as measured by the pre-peaks in SE-UHPLC.

In one embodiment, the amount of erenumab in the composition is about 97.9% or greater as measured by the main peak in SE-UHPLC, and the amount of HMW species in the composition is about 2.1% or less as measured by the pre-peaks in SE-UHPLC. In another embodiment, the amount of erenumab in the composition is about 98.2% or greater as measured by the main peak in SE-UHPLC, and the amount of HMW species in the composition is about 1.8% or less as measured by the pre-peaks in SE-UHPLC. In yet another embodiment, the amount of erenumab in the composition is about 98.8% or greater as measured by the main peak in SE-UHPLC, and the amount of HMW species in the composition is about 1.2% or less as measured by the pre-peaks in SE-UHPLC. In still another embodiment, the amount of erenumab in the composition is about 98.6% or greater as measured by the main peak in SE-UHPLC, and the amount of HMW species in the composition is about 1.4% or less as measured by the pre-peaks in SE-UHPLC. In these and other embodiments, the SE-UHPLC is conducted as described in Example 5 and the amounts are determined from the peak area percentage for the main peak and pre-peaks.

The amount of size variants (e.g. HMW species) in erenumab compositions can be reduced using methods that separate proteins based on size or hydrodynamic volume, such as size exclusion chromatography and filtration steps. In addition, affinity chromatography (e.g. protein A chromatography), cation exchange chromatography, hydrophobic interaction chromatography, and mixed mode chromatography can also effectively reduce HMW species. See, e.g., the methods described in Shukla et al., Journal of Chromatography B, Vol. 848: 28-39, 2007; Chen et al., Journal of Chromatography A, Vol. 1217: 216-224, 2010; U.S. Pat. Nos. 6,620,918; 9,505,803; and 9,783,570. As described above, HMW species of erenumab elute earlier than erenumab (main peak) upon separation by size exclusion chromatography. Thus, HMW species can be collected and discarded prior to elution of the erenumab main peak or collection of erenumab fractions can be started following elution of the HMW species.

The erenumab compositions of the invention may be analyzed for one or more of the erenumab variants described herein. For instance, in some embodiments, the present invention includes compositions comprising erenumab and one or more erenumab variants, wherein the erenumab variants comprise isomerization variants, deamidation variants, acidic variants, HMW species, or combinations thereof, and wherein the compositions have controlled amounts of each of these variants. In one embodiment, the composition comprises erenumab and one or more erenumab variants, wherein the erenumab variants comprise isomerization variants, deamidation variants, acidic variants, HMW species, or combinations thereof, and wherein the composition has one or more or all of the following characteristics: (a) the amount of acidic variants in the composition is from about 25% to about 38% as measured by CEX-HPLC; (b) the amount of HMW species in the composition is about 2.1% or less as measured by SE-UHPLC; and (c) the amount of isomerization variants and deamidation variants in the composition is about 8.0% or less as measured by the pre-peaks in HIC-HPLC. In another embodiment, the composition has one or more or all of the following characteristics: (a) the amount of acidic variants in the composition is less than about 38% as measured by CEX-HPLC; (b) the amount of HMW species in the composition is about 2.5% or less as measured by SE-UHPLC; and (c) the amount of isomerization variants and deamidation variants in the composition is about 10% or less as measured by the pre-peaks in HIC-HPLC. In another embodiment, the composition has one or more or all of the following characteristics: (a) the amount of acidic variants in the composition is from about 32.5% to about 37.5% as measured by CEX-HPLC; (b) the amount of HMW species in the composition is about 1.8% or less as measured by SE-UHPLC; and (c) the amount of isomerization variants and deamidation variants in the composition is about 6.1% or less as measured by the pre-peaks in HIC-HPLC. In yet another embodiment, the composition has one or more or all of the following characteristics: (a) the amount of acidic variants in the composition is from about 26.5% to about 33.6% as measured by CEX-HPLC; (b) the amount of HMW species in the composition is about 1.2% or less as measured by SE-UHPLC; and (c) the amount of isomerization variants and deamidation variants in the composition is about 3.2% or less as measured by the pre-peaks in HIC-HPLC. In still another embodiment, the composition has one or more or all of the following characteristics: (a) the amount of acidic variants in the composition is from about 26.5% to about 33.6% as measured by CEX-HPLC; (b) the amount of HMW species in the composition is about 1.2% or less as measured by SE-UHPLC; and (c) the amount of isomerization variants and deamidation variants in the composition is about 2.7% or less as measured by the pre-peaks in HIC-HPLC. In another embodiment, the composition has one or more or all of the following characteristics: (a) the amount of acidic variants in the composition is from about 26.5% to about 33.6% as measured by CEX-HPLC; (b) the amount of HMW species in the composition is about 1.4% or less as measured by SE-UHPLC; and (c) the amount of isomerization variants and deamidation variants in the composition is about 3.2% or less as measured by the pre-peaks in HIC-HPLC. In another embodiment, the composition has one or more or all of the following characteristics: (a) the amount of acidic variants in the composition is from about 28.7% to about 31.3% as measured by CEX-HPLC; (b) the amount of HMW species in the composition is about 0.6% or less as measured by SE-UHPLC; and (c) the amount of isomerization variants and deamidation variants in the composition is about 2.1% or less as measured by the pre-peaks in HIC-HPLC.

Erenumab compositions of the invention can be prepared by recombinantly expressing nucleic acids encoding the heavy chain and light chain in a host cell, partially purifying or purifying erenumab from host cell cultures or host cell lysates, and analyzing the resulting compositions for one or more of the erenuamb variants detailed herein according to the methods described in more detail below.

For recombinant production of erenumab, one or more nucleic acids encoding the heavy chain (e.g. heavy chain polypeptide comprising the amino acid sequence of SEQ ID NO: 1) and light chain (e.g. light chain polypeptide comprising the amino acid sequence of SEQ ID NO: 2) is inserted into one or more expression vectors. The nucleic acid encoding the heavy chain and the nucleic acid encoding the light chain can be inserted into a single expression vector or they can be inserted into separate expression vectors. The term "expression vector" or "expression construct" as used herein refers to a recombinant DNA molecule containing a desired coding sequence and appropriate nucleic acid control sequences necessary for the expression of the operably linked coding sequence in a particular host cell. An expression vector can include sequences that affect or control transcription, translation, and, if introns are present, affect RNA splicing of a coding region operably linked thereto. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. A secretory signal peptide sequence can also, optionally, be encoded by the expression vector, operably linked to the coding sequence of interest, so that the expressed polypeptide can be secreted by the recombinant host cell, for more facile isolation of the polypeptide of interest from the cell, if desired. Vectors may also include one or more selectable marker genes to facilitate selection of host cells into which the vectors have been introduced. Exemplary nucleic acids encoding the heavy and light chains of erenumab as well as suitable signal peptide sequences and other components for expression vectors for recombinantly expressing erenumab are described in PCT Publication No. WO 2010/075238, which is hereby incorporated by reference in its entirety.

After the expression vector has been constructed and the one or more nucleic acid molecules encoding the heavy and light chain components of erenumab has been inserted into the proper site(s) of the vector or vectors, the completed vector(s) may be inserted into a suitable host cell for amplification and/or polypeptide expression. The transformation of an expression vector for erenumab into a selected host cell may be accomplished by well-known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook, Fritsch and Maniatis (eds), Molecular Cloning; A Laboratory Manual, Second Edition, Cold Spring Harbor, N.Y., (1989), Ausubel et al. (eds.) Current Protocols in Molecular Biology, Greene Publishing Associates, (1989).

A host cell, when cultured under appropriate conditions, synthesizes erenumab that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Exemplary host cells include prokaryote, yeast, or higher eukaryote cells. Prokaryotic host cells include eubacteria, such as Gram-negative or Gram-positive organisms, for example, Enterobacteriaceae such as Escherichia, e.g., E. coli, Enterobacter, Envinia, Klebsiella, Proteus, Salmonella, e.g., Salmonella typhimurium, Serratia, e.g., Serratia marcescans, and Shigella, as well as Bacillus, such as B. subtilis and B. licheniformis, Pseudomonas, and Streptomyces.

Eukaryotic microbes such as filamentous fungi or yeast are suitable cloning or expression hosts for recombinant polypeptides. Saccharomyces cerevisiae, or common baker's yeast, is the most commonly used among lower eukaryotic host microorganisms. However, a number of other genera, species, and strains are commonly available and useful herein, such as Pichia, e.g. P. pastoris, Schizosaccharomyces pombe; Kluyveromyces, Yarrowia; Candida; Trichoderma reesia; Neurospora crassa; Schwanniomyces, such as Schwanniomyces occidentalis; and filamentous fungi, such as, e.g., Neurospora, Penicillium, Tolypocladium, and Aspergillus hosts such as A. nidulans and A. niger.

Host cells for the expression of glycosylated antibodies can be derived from multicellular organisms. Examples of invertebrate cells include plant and insect cells. Numerous baculoviral strains and variants and corresponding permissive insect host cells from hosts such as Spodoptera frugiperda (caterpillar), Aedes aegypti (mosquito), Aedes albopictus (mosquito), Drosophila melanogaster (fruitfly), and Bombyx mori have been identified. A variety of viral strains for transfection of such cells are publicly available, e.g., the L-1 variant of Autographa californica NPV and the Bm-5 strain of Bombyx mori NPV.

Vertebrate host cells are also suitable hosts, and recombinant production of antibodies from such cells has become routine procedure. Mammalian cell lines available as hosts for expression are well known in the art and include, but are not limited to, immortalized cell lines available from the American Type Culture Collection (ATCC), including but not limited to Chinese hamster ovary (CHO) cells, including CHOK1 cells (ATCC CCL61), DXB-11, DG-44, and Chinese hamster ovary cells/-DHFR (CHO, Urlaub et al., Proc. Natl. Acad. Sci. USA 77: 4216, 1980); monkey kidney CV1 line transformed by SV40 (COS-7, ATCC CRL 1651); human embryonic kidney line (293 or 293 cells subcloned for growth in suspension culture, (Graham et al., J. Gen Virol. 36: 59, 1977); baby hamster kidney cells (BHK, ATCC CCL 10); mouse sertoli cells (TM4, Mather, Biol. Reprod. 23: 243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G2, HB 8065); mouse mammary tumor (MMT 060562, ATCC CCL51); TRI cells (Mather et al., Annals N.Y Acad. Sci. 383: 44-68, 1982); MRC 5 cells or FS4 cells; mammalian myeloma cells, and a number of other cell lines. CHO cells are preferred host cells in some embodiments for expressing erenumab.

Host cells are transformed or transfected with the above-described expression vectors for production of erenumab and are cultured in conventional nutrient media modified as appropriate for inducing promoters, selecting transformants, or amplifying the genes encoding the desired sequences. The host cells used to produce erenumab may be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing the host cells. In addition, any of the media described in Ham et al., Meth. Enz. 58: 44, 1979; Barnes et al., Anal. Biochem. 102: 255, 1980; U.S. Pat. Nos. 4,767,704; 4,657,866; 4,927,762; 4,560,655; or 5,122,469; WO 90/03430; or WO 87/00195 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinary skilled artisan.

Upon culturing the host cells, the antibody can be produced intracellularly, in the periplasmic space, or directly secreted into the medium. If the antibody is produced intracellularly, as a first step, the host cells are lysed (e.g., by mechanical shear, osmotic shock, or enzymatic methods) and the particulate debris (e.g., host cells and lysed fragments), is removed, for example, by centrifugation, microfiltration, or ultrafiltration. If the antibody is secreted into the culture medium, the antibody can be separated from host cells through centrifugation or microfiltration, and optionally, subsequently concentrated through ultrafiltration. Erenumab can be further purified or partially purified using, for example, one or more chromatography steps, such as affinity chromatography (e.g. protein A or protein G affinity chromatography), cation exchange chromatography, anion exchange chromatography, hydroxyapatite chromatography, hydrophobic interaction chromatography, or mixed mode chromatography.

Once an erenumab composition is produced or obtained, the composition may be evaluated for the presence and amount of one or more erenumab variants described herein, including isomerization variants, deamidation variants, acidic variants, and size variants (e.g. HMW species). Accordingly, the present invention includes methods for assessing the quality of an erenumab composition, comprising obtaining an erenumab composition that contains erenumab and one or more erenumab variants; measuring the amount of one or more erenumab variants in the composition; comparing the measured amount of the one or more erenumab variants to a pre-determined reference criterion; and preparing a pharmaceutical formulation or pharmaceutical product of the erenumab composition if the comparison indicates that the pre-determined reference criterion is met. In some embodiments, the methods comprise one, two, or three of: (1) measuring the amount of isomerization variants and deamidation variants in the composition, (2) measuring the amount of acidic variants in the composition, and/or (3) measuring the amount of BMW species in the composition. In certain embodiments, all three measurements are performed on an erenumab composition.

The pre-determined reference criterion for each erenumab variant can be a threshold amount or range of amounts of the variant that do not significantly affect the potency of the erenumab composition for inhibiting ligand-induced activation of the CGRP receptor. For instance, the pre-determined reference criterion for each erenumab variant can be any of the limits or ranges disclosed herein for each of the variants as erenumab compositions with these limits/ranges of the variants had comparable potency to erenumab compositions evaluated in clinical trials and shown to have clinical efficacy.

In certain embodiments of the methods, if the measured amount of the erenumab variant in the composition meets the pre-determined reference criterion, then the erenumab composition can be classified as acceptable and progressed to the next step in the manufacturing or distribution process, such as for example, by preparing a pharmaceutical formulation of the composition (e.g. by combining with one or more excipients or diluents); by preparing a pharmaceutical product of the composition (e.g., by filling into vials, syringes, autoinjectors, or other containers or delivery devices); packaging the composition with instructions for use, diluents, and/or delivery devices; or releasing the composition for commercial sale or shipping to distributors. In some embodiments of the methods, a pharmaceutical formulation of the erenumab composition is prepared if the measured amount of the erenumab variant in the composition meets the pre-determined reference criterion. In other embodiments of the methods, a pharmaceutical product of the erenumab composition is prepared if the measured amount of the erenumab variant in the composition meets the pre-determined reference criterion. Methods of preparing pharmaceutical formulations and pharmaceutical products of erenumab compositions are described in more detail below. If the measured amount of the erenumab variant in the composition does not meet the pre-determined reference criterion, then, in some embodiments of the methods, the erenumab composition can be classified as unacceptable and discarded, destroyed, or subject to additional manufacturing steps, such as additional purification to remove or reduce the amount of the erenumab variant in the composition such that the pre-determined reference criterion is met.

In one embodiment, the methods for assessing the quality of an erenumab composition comprise obtaining an erenumab composition that contains erenumab and erenumab isomerization and deamidation variants; measuring the amount of the isomerization variants and deamidation variants in the composition; comparing the measured amount of the isomerization variants and deamidation variants to a pre-determined reference criterion; and preparing a pharmaceutical formulation or pharmaceutical product of the erenumab composition if the comparison indicates that the pre-determined reference criterion is met. The pre-determined reference criterion for the amount of isomerization and deamidation variants in an erenumab composition can be less than about 30%, for example about 25% or less, about 20% or less, about 17% or less, about 15% or less, about 12% or less, about 10% or less, about 8% or less, about 6% or less, or about 4% or less. In one embodiment, the pre-determined reference criterion for the amount of isomerization and deamidation variants in an erenumab composition is about 15% or less. In another embodiment, the pre-determined reference criterion for the amount of isomerization and deamidation variants in an erenumab composition is about 10% or less. In another embodiment, the pre-determined reference criterion for the amount of isomerization and deamidation variants in an erenumab composition is about 8% or less. In yet another embodiment, the pre-determined reference criterion for the amount of isomerization and deamidation variants in an erenumab composition is about 6% or less. In still another embodiment, the pre-determined reference criterion for the amount of isomerization and deamidation variants in an erenumab composition is about 4% or less. In certain embodiments, the pre-determined reference criterion for the amount of isomerization and deamidation variants in an erenumab composition is about 3.2% or less. In other embodiments, the pre-determined reference criterion for the amount of isomerization and deamidation variants in an erenumab composition is about 2.7% or less. In some embodiments, the pre-determined reference criterion for the amount of isomerization and deamidation variants in an erenumab composition can be a range of amounts, for example, from about 1% to about 10% of an erenumab composition, from about 1% to about 4% of an erenumab composition, or from about 0.5% to about 3.5% of an erenumab composition. In certain embodiments, the amount of isomerization variants and deamidation variants in an erenumab composition is measured by HIC-HPLC, e.g. by the peak area percentage of the pre-peaks in HIC-HPLC. In such embodiments the HIC-HPLC method can be performed as described in Example 1.

In another embodiment, the methods for assessing the quality of an erenumab composition comprise obtaining an erenumab composition that contains erenumab and erenumab acidic variants; measuring the amount of the acidic variants in the composition; comparing the measured amount of the acidic variants to a pre-determined reference criterion; and preparing a pharmaceutical formulation or pharmaceutical product of the erenumab composition if the comparison indicates that the pre-determined reference criterion is met. The pre-determined reference criterion for the amount of acidic variants in an erenumab composition can be less than about 40%, for example about 38% or less, about 37% or less, about 36% or less, about 35% or less, about 34% or less, about 33% or less, about 32% or less, about 31% or less, about 30% or less, about 29% or less, about 28% or less, about 27% or less, or about 26% or less. In one embodiment, the pre-determined reference criterion for the amount of acidic variants in an erenumab composition is about 38% or less. In another embodiment, the pre-determined reference criterion for the amount of acidic variants in an erenumab composition is about 35% or less. In yet another embodiment, the pre-determined reference criterion for the amount of acidic variants in an erenumab composition is about 32% or less. In still another embodiment, the pre-determined reference criterion for the amount of acidic variants in an erenumab composition is about 30% or less. In some embodiments, the pre-determined reference criterion for the amount of acidic variants in an erenumab composition is a range of amounts, such as about 25% to about 38% of an erenumab composition, about 32.5% to about 37.5% of an erenumab composition, about 26% to about 34% of an erenumab composition, or about 26.5% to about 33.6% of an erenumab composition. In one particular embodiment, the pre-determined reference criterion for the amount of acidic variants in an erenumab composition is about 25% to about 38%. In another particular embodiment, the pre-determined reference criterion for the amount of acidic variants in an erenumab composition is about 26.5% to about 33.6%. In certain embodiments, the amount of acidic variants in an erenumab composition is measured by CEX-HPLC, e.g. by the peak area percentage of the acidic peaks in CEX-HPLC. In such embodiments the CEX-HPLC method can be performed as described in Example 3.

In another embodiment, the methods for assessing the quality of an erenumab composition comprise obtaining an erenumab composition that contains erenumab and HMW species of erenumab; measuring the amount of the HMW species in the composition; comparing the measured amount of the BMW species to a pre-determined reference criterion; and preparing a pharmaceutical formulation or pharmaceutical product of the erenumab composition if the comparison indicates that the pre-determined reference criterion is met. The pre-determined reference criterion for the amount of HMW species in an erenumab composition can be less than about 3.0%, for example about 2.5% or less, about 2.4% or less, about 2.3% or less, about 2.2% or less, about 2.1% or less, about 2.0% or less, about 1.8% or less, about 1.6% or less, about 1.4% or less, about 1.2% or less, about 1.0% or less, about 0.8% or less, about 0.6% or less, or about 0.4% or less. In one embodiment, the pre-determined reference criterion for the amount of HMW species in an erenumab composition is about 2.5% or less. In another embodiment, the pre-determined reference criterion for the amount of HMW species in an erenumab composition is about 1.8% or less. In another embodiment, the pre-determined reference criterion for the amount of HMW species in an erenumab composition is about 1.4% or less. In yet another embodiment, the pre-determined reference criterion for the amount of HMW species in an erenumab composition is about 1.2% or less. In still another embodiment, the pre-determined reference criterion for the amount of HMW species in an erenumab composition is about 0.6% or less. The pre-determined reference criterion for the amount of HMW species in an erenumab composition can, in some embodiments, be a range of amounts, for example from about 0.3% to about 2.4% of an erenumab composition, from about 0.6% to about 2.1% of an erenumab composition, from about 0.4% to about 1.2% of an erenumab composition, or from about 0.6% to about 1.4% of an erenumab composition. In certain embodiments, the amount of HMW species in an erenumab composition is measured by SE-UHPLC, e.g. by the peak area percentage of the pre-peaks in SE-UHPLC. In such embodiments the SE-UHPLC method can be performed as described in Example 5.

In certain embodiments of the methods of the invention, the methods comprise:

(a) obtaining an erenumab composition that contains erenumab and one or more erenumab variants, wherein the erenumab variants comprise isomerization variants, deamidation variants, acidic variants, HMW species, or combinations thereof;

(b) evaluating the erenumab composition by performing one, two, or all three of the following:
  (i) measuring the amount of isomerization variants and deamidation variants in the composition by the pre-peaks in HIC-HPLC and comparing the measured amount to a pre-determined reference criterion of about 10% or less;
  (ii) measuring the amount of acidic variants in the composition by the acidic peaks in CEX-HPLC and comparing the measured amount to a pre-determined reference criterion of about 25% to about 38%; and/or
  (iii) measuring the amount of HMW species in the composition by the pre-peaks in SE-UHPLC and comparing the measured amount to a pre-determined reference criterion of about 2.5% or less; and (c) preparing a pharmaceutical formulation or pharmaceutical product of the erenumab composition if the comparison or comparisons in step (b) indicate that the pre-determined reference criterion/criteria are met. In some embodiments, all three steps (b)(i), (b)(ii), and (b)(iii) are performed. In other embodiments, only steps (b)(i) and (b)(ii) are performed. In still other embodiments, only steps (b)(ii) and (b)(iii) are performed. In certain embodiments, only steps (b)(i) and (b)(iii) are performed.

In certain other embodiments of the methods of the invention, the methods comprise:

(a) obtaining an erenumab composition that contains erenumab and one or more erenumab variants, wherein the erenumab variants comprise isomerization variants, deamidation variants, acidic variants, HMW species, or combinations thereof;

(b) evaluating the erenumab composition by performing one, two, or all three of the following:
   (i) measuring the amount of isomerization variants and deamidation variants in the composition by the pre-peaks in HIC-HPLC and comparing the measured amount to a pre-determined reference criterion of about 3.2% or less;
   (ii) measuring the amount of acidic variants in the composition by the acidic peaks in CEX-HPLC and comparing the measured amount to a pre-determined reference criterion of about 26.5% to about 33.6%; and/or
   (iii) measuring the amount of HMW species in the composition by the pre-peaks in SE-UHPLC and comparing the measured amount to a pre-determined reference criterion of about 1.2% or less; and
(c) preparing a pharmaceutical formulation or pharmaceutical product of the erenumab composition if the comparison or comparisons in step (b) indicate that the pre-determined reference criterion/criteria are met. In some embodiments, all three steps (b)(i), (b)(ii), and (b)(iii) are performed. In other embodiments, only steps (b)(i) and (b)(ii) are performed. In still other embodiments, only steps (b)(ii) and (b)(iii) are performed. In certain embodiments, only steps (b)(i) and (b)(iii) are performed.

In some embodiments of the methods of the invention, the methods comprise:
(a) obtaining an erenumab composition that contains erenumab and one or more erenumab variants, wherein the erenumab variants comprise isomerization variants, deamidation variants, acidic variants, HMW species, or combinations thereof;
(b) evaluating the erenumab composition by performing one, two, or all three of the following:
   (i) measuring the amount of isomerization variants and deamidation variants in the composition by the pre-peaks in HIC-HPLC and comparing the measured amount to a pre-determined reference criterion of about 2.7% or less;
   (ii) measuring the amount of acidic variants in the composition by the acidic peaks in CEX-HPLC and comparing the measured amount to a pre-determined reference criterion of about 26.5% to about 33.6%; and/or
   (iii) measuring the amount of HMW species in the composition by the pre-peaks in SE-UHPLC and comparing the measured amount to a pre-determined reference criterion of about 1.2% or less; and
(c) preparing a pharmaceutical formulation or pharmaceutical product of the erenumab composition if the comparison or comparisons in step (b) indicate that the pre-determined reference criterion/criteria are met. In some embodiments, all three steps (b)(i), (b)(ii), and (b)(iii) are performed. In other embodiments, only steps (b)(i) and (b)(ii) are performed. In still other embodiments, only steps (b)(ii) and (b)(iii) are performed. In certain embodiments, only steps (b)(i) and (b)(iii) are performed.

In other embodiments of the methods of the invention, the methods comprise:
(a) obtaining an erenumab composition that contains erenumab and one or more erenumab variants, wherein the erenumab variants comprise isomerization variants, deamidation variants, acidic variants, HMW species, or combinations thereof;
(b) evaluating the erenumab composition by performing one, two, or all three of the following:
   (i) measuring the amount of isomerization variants and deamidation variants in the composition by the pre-peaks in HIC-HPLC and comparing the measured amount to a pre-determined reference criterion of about 3.2% or less;
   (ii) measuring the amount of acidic variants in the composition by the acidic peaks in CEX-HPLC and comparing the measured amount to a pre-determined reference criterion of about 26.5% to about 33.6%; and/or
   (iii) measuring the amount of HMW species in the composition by the pre-peaks in SE-UHPLC and comparing the measured amount to a pre-determined reference criterion of about 1.4% or less; and
(c) preparing a pharmaceutical formulation or pharmaceutical product of the erenumab composition if the comparison or comparisons in step (b) indicate that the pre-determined reference criterion/criteria are met. In some embodiments, all three steps (b)(i), (b)(ii), and (b)(iii) are performed. In other embodiments, only steps (b)(i) and (b)(ii) are performed. In still other embodiments, only steps (b)(ii) and (b)(iii) are performed. In certain embodiments, only steps (b)(i) and (b)(iii) are performed.

The methods of the invention for assessing the quality or evaluating erenumab compositions described above can be employed in various contexts. For instance, the methods may be used as quality control methods at different steps of the manufacturing process for erenumab (e.g. as in-process control methods). In some embodiments, the methods can be used at the completion of most or all of the manufacturing process, e.g. as lot release methods for erenumab drug substance (e.g. an active pharmaceutical ingredient or API) or erenumab drug product (e.g. API formulated with one or more excipients for human use). The methods may also be used to evaluate erenumab compositions that have been stored for various periods of time to facilitate the determination of drug expiry dates. The methods can also be used to re-evaluate erenumab compositions for which the pre-determined reference criteria were not met initially and have been reprocessed (e.g. subject to additional purification operations).

Thus, the erenumab composition employed in the methods can be any composition that comprises erenumab and potentially one or more erenumab variants. In some embodiments, the erenumab composition is obtained from a Chinese Hamster Ovary (CHO) cell line that expresses a nucleic acid encoding a heavy chain of SEQ ID NO: 1 and a nucleic acid encoding a light chain of SEQ ID NO: 2. In such embodiments, the erenumab composition is a cell culture harvest (e.g. clarified cell culture supernatant or clarified cell lysate). In other such embodiments, the erenumab composition is a partially purified preparation of erenumab that has been subject to one or more purification operations (e.g. pool or fraction from one or more chromatography or filtration steps). In one embodiment, the erenumab composition is an elution pool from a cation exchange chromatography material. In another embodiment, the erenumab composition is erenumab drug substance (e.g. an active pharmaceutical ingredient or API). In yet another embodiment, the erenumab composition is erenumab drug product (e.g. erenumab drug substance or API formulated with one or more excipients for human use).

The biological activity of the erenumab compositions can be evaluated as part of the quality assessment methods described above. In some embodiments, the methods comprise assessing the ability of the erenumab compositions to inhibit CGRP ligand-induced activation of the human CGRP receptor. Various assays for assessing activation of CGRP receptors are known in the art and include cell-based assays measuring CGRP ligand-induced calcium mobilization and cAMP production. An exemplary cell-based cAMP assay is described in Example 1. Other suitable CGRP receptor activation assays are described in Aiyar et al., Molecular and Cellular Biochemistry, Vol. 197:179-185, 1999; Pin et al., European Journal of Pharmacology, Vol. 577: 7-16, 2007; U.S. Pat. No. 8,168,592, and WO 2010/075238, all of which are hereby incorporated by reference in their entireties.

The present invention includes pharmaceutical formulations comprising any one of the erenumab compositions described herein and one or more pharmaceutically acceptable excipients. "Pharmaceutically-acceptable" refers to molecules, compounds, and compositions that are non-toxic to human recipients at the dosages and concentrations employed and/or do not produce allergic or adverse reactions when administered to humans. In certain embodiments, the pharmaceutical formulation may contain materials for modifying, maintaining or preserving, for example, the pH, osmolarity, viscosity, clarity, color, isotonicity, odor, sterility, stability, rate of dissolution or release, adsorption or penetration of the erenumab composition. In such embodiments, suitable materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); diluents; excipients and/or pharmaceutical adjuvants. Methods and suitable materials for formulating molecules for therapeutic use are known in the pharmaceutical arts, and are described, for example, in REMINGTON'S PHARMACEUTICAL SCIENCES, 18th Edition, (A. R. Genrmo, ed.), 1990, Mack Publishing Company.

In some embodiments, the pharmaceutical formulations of the invention comprise an erenumab composition described herein, a buffer that maintains the pH of the solution within a range of about 4.5 to about 6.5, a stabilizing agent, and optionally a surfactant. Suitable buffers include, but are not limited to, glutamate, acetate, Tris, citrate, histidine, succinate, and phosphate buffers. In certain embodiments, the pharmaceutical formulation comprises an acetate buffer. The acetate buffer can be made from acetic acid or an acetate salt, for example, sodium acetate. Other salts can be used, for example such as potassium, ammonium, calcium or magnesium salts of acetate. Pharmaceutical formulations comprising an acetate buffer typically have a pH of about 4.5 to about 5.5 or a pH of about 4.8 to about 5.2, including a pH of about 4.5, about 4.6, about 4.7, about 4.8, about 4.9, about 5.0, about 5.1, about 5.2, about 5.3, about 5.4, and about 5.5.

A stabilizing agent refers to an excipient that stabilizes the native conformation of the antibody and/or prevents or reduces the physical or chemical degradation of the antibody. Suitable stabilizing agents include, but are not limited to, polyols (e.g. sorbitol, glycerol, mannitol, xylitol, maltitol, lactitol, erythritol and threitol), sugars (e.g., fructose, glucose, glyceraldehyde, lactose, arabinose, mannose, xylose, ribose, rhamnose, galactose maltose, sucrose, trehalose, sorbose, sucralose, melezitose and raffinose), and amino acids (e.g., glycine, methionine, proline, lysine, arginine, histidine, or glutamic acid). In some embodiments, the pharmaceutical formulation comprises a sugar as a stabilizing agent. In these and other embodiments, the sugar is sucrose.

In certain embodiments, the pharmaceutical formulation comprises a surfactant. A surfactant is a substance that functions to reduce the surface tension of a liquid in which it is dissolved. Surfactants can be included in pharmaceutical formulations for a variety of purposes including, for example, to prevent or control aggregation, particle formation and/or surface adsorption in liquid formulations or to prevent or control these phenomena during the lyophilization and/or reconstitution process in lyophilized formulations. Surfactants include, for example, amphipathic organic compounds that exhibit partial solubility in both organic solvents and aqueous solutions. General characteristics of surfactants include their ability to reduce the surface tension of water, reduce the interfacial tension between oil and water and also form micelles. Surfactants that may be incorporated into the pharmaceutical formulations of the invention include both non-ionic and ionic surfactants. Suitable non-ionic surfactants include, but are not limited to, alkyl poly (ethylene oxide), alkyl polyglucosides, such as octyl glucoside and decyl maltoside, fatty alcohols, such as cetyl alcohol and oleyl alcohol, cocamide MEA, cocamide DEA, and cocamide TEA. Specific examples of non-ionic surfactants include the polysorbates including, for example, polysorbate 20, polysorbate 28, polysorbate 40, polysorbate 60, polysorbate 65, polysorbate 80, polysorbate 81, polysorbate 85 and the like; the poloxamers including, for example, poloxamer 188, also known as poloxalkol or poly(ethylene oxide)-poly(propylene oxide), poloxamer 407 or polyethylene-polypropylene glycol and the like, and polyethylene glycol (PEG). Suitable ionic surfactants include, for example, anionic, cationic and zwitterionic surfactants. Anionic surfactants include, but are not limited to, sulfonate-based or carboxylate-based surfactants such as soaps, fatty acid salts, sodium dodecyl sulfate (SDS), ammonium lauryl sulfate and other alkyl sulfate salts. Cationic surfactants include, but are not limited to, quaternary ammonium-based surfactants such as cetyl trimethylammonium bromide (CTAB), other alkyltrimethylammonium salts, cetyl pyridinium chloride, polyethoxylated tallow amine (POEA) and benzalkonium chloride. Zwitterionic or amphoteric surfactants include, for example, dodecyl betaine, dodecyl dimethylamine oxide, cocamidopropyl betaine and coco ampho glycinate. In certain embodiments, the pharmaceutical formulation comprises a non-ionic surfactant. In one embodiment, the non-ionic surfactant is polysorbate 20. In another embodiment, the non-ionic surfactant is polysorbate 80.

In certain embodiments, the pharmaceutical formulations comprise any one of the erenumab compositions described herein (e.g. about 70 mg/mL to about 140 mg/mL of an erenumab composition), about 20 mM to about 40 mM acetate, about 6% to about 9% (w/v) sucrose, and about 0.008% to about 0.012% (w/v) polysorbate 80 or polysorbate 20. The pH of these formulations is in the range of about 4.9 to about 5.5 (e.g., pH of about 4.9, about 5.0, about 5.1, about 5.2, about 5.3, or about 5.4). In one particular embodiment, the pharmaceutical formulation comprises 70 mg/mL of an erenumab composition described herein, about 25 mM acetate, about 7.3% (w/v) sucrose, and about 0.010% (w/v) polysorbate 80, wherein the pharmaceutical formulation has a pH of about 5.2±0.2. In another particular embodiment, the pharmaceutical formulation comprises 140 mg/mL of an erenumab composition described herein, about 34 mM acetate, about 6.5% (w/v) sucrose, and about 0.010% (w/v) polysorbate 80, wherein the pharmaceutical formulation has a pH of about 5.2±0.2.

The pharmaceutical formulations are preferably suitable for parenteral injection (e.g. intravenous or subcutaneous injection). Illustrative pharmaceutical forms suitable for parenteral injection include sterile aqueous solutions or dispersions and sterile powders for the extemporaneous preparation of sterile injectable solutions or dispersions. Preferably, the pharmaceutical formulation is sterile and is sufficiently fluid to allow for delivery via a syringe or other injection device (i.e., the formulation is not excessively viscous so as to prevent passage through a syringe or other injection device). Sterilization can be accomplished by filtration through sterile filtration membranes. When the composition is lyophilized, sterilization using this filtration method may be conducted either prior to or following lyophilization and reconstitution. Pharmaceutical formulations for parenteral administration can be stored in lyophilized form or in a solution. Parenteral formulations can be placed into a container having a sterile access port, for example, an intravenous solution bag or vial having a stopper pierceable by a hypodermic injection needle. Parenteral formulations can also be stored in syringes, autoinjector devices, or pen injection devices or cartridges adapted for use with such injection devices.

The pharmaceutical formulations described above can be filled into vials, syringes, autoinjectors, or other containers or delivery devices and optionally packaged with instructions for use (e.g. prescribing information containing instructions for using the pharmaceutical formulations for treating, preventing, or reducing the occurrence of headache, e.g. migraine headache) to prepare pharmaceutical products. In certain embodiments, the pharmaceutical formulations described herein are incorporated into a self-administration injection device. Such devices are commercially available and include, but are not limited to, autoinjectors, dosing pens, microinfusion pumps, and pre-filled syringes. Exemplary devices in which the pharmaceutical formulations of the invention can be incorporated include autoinjectors (e.g., SureClick®, EverGentle®, Avanti®, DosePro®, Molly®, and Leva®), pen injection devices (e.g., Madie® pen injector, DCP™ pen injector, BD Vystra™ disposable pen, BD™ reusable pen), and pre-filled syringes (BD Sterifill™, BD Hypak™, prefilled syringes from Baxter). In some embodiments, the pharmaceutical formulation is incorporated into and stored in a syringe to produce a pre-filled syringe. In other embodiments, the pharmaceutical formulation is incorporated into an autoinjector. The injection volume of the pre-filled syringe or autoinjector can be about 2 mL or less, about 1.5 mL or less, or about 1 mL or less. In certain embodiments, the pharmaceutical formulations described herein are incorporated into a syringe or autoinjector with an injection volume of about 1 mL.

Thus, in some embodiments, the present invention provides a pre-filled syringe comprising about 70 mg/mL to about 140 mg/mL of an erenumab composition described herein, about 20 mM to about 40 mM acetate, about 6% to about 9% (w/v) sucrose, and about 0.008% to about 0.012% (w/v) polysorbate 80 or polysorbate 20 at a pH of about 4.5 to about 5.5. In one embodiment, the pre-filled syringe comprises 70 mg/mL of an erenumab composition described herein, about 25 mM acetate, about 7.3% (w/v) sucrose, and about 0.010% (w/v) polysorbate 80, at a pH of about 5.2±0.2. In another embodiment, the pre-filled syringe comprises 140 mg/mL of an erenumab composition described herein, about 34 mM acetate, about 6.5% (w/v) sucrose, and about 0.010% (w/v) polysorbate 80, at a pH of about 5.2±0.2. In any of these embodiments, the injection volume of the pre-filled syringe can be about 1 mL.

In other embodiments, the present invention provides an autoinjector comprising about 70 mg/mL to about 140 mg/mL of an erenumab composition described herein, about 20 mM to about 40 mM acetate, about 6% to about 9% (w/v) sucrose, and about 0.008% to about 0.012% (w/v) polysorbate 80 or polysorbate 20 at a pH of about 4.5 to about 5.5. In one embodiment, the autoinjector comprises 70 mg/mL of an erenumab composition described herein, about 25 mM acetate, about 7.3% (w/v) sucrose, and about 0.010% (w/v) polysorbate 80, at a pH of about 5.2±0.2. In another embodiment, the autoinjector comprises 140 mg/mL of an erenumab composition described herein, about 34 mM acetate, about 6.5% (w/v) sucrose, and about 0.010% (w/v) polysorbate 80, at a pH of about 5.2±0.2. In any of these embodiments, the injection volume of the autoinjector can be about 1 mL.

The erenumab compositions described herein and pharmaceutical formulations comprising such compositions can be used to treat, prevent, or reduce the occurrence of headache. Accordingly, the present invention includes methods for treating, preventing, or reducing the occurrence of headache in a patient in need thereof comprising administering to the patient any of the erenumab compositions or pharmaceutical formulations comprising the erenumab compositions described herein. In certain embodiments, the present invention provides erenumab compositions or pharmaceutical formulations comprising the erenumab compositions described herein for use in treating, preventing, or reducing the occurrence of headache in a patient in need thereof. In other embodiments, the present invention includes the use of erenumab compositions or pharmaceutical formulations comprising the erenumab compositions described herein in the preparation of a medicament for treating, preventing, or reducing the occurrence of headache in a patient in need thereof. "Preventing or reducing the occurrence of headache" refers to a reduction in the frequency, duration, or severity of the headache as compared to the frequency, duration, or severity of the headache prior to administration of the composition/formulation or as compared to the frequency, duration, or severity of the headache in a patient not administered the composition/formulation (i.e. a control subject).

In certain embodiments, the methods or uses of the invention treat, prevent, or reduce the occurrence of migraine headache in a patient in need thereof by administering to the patient any of the erenumab compositions or pharmaceutical formulations comprising the erenumab compositions described herein. A "migraine headache" is a headache associated with nausea or vomiting or sensitivity to light or sound and/or a headache characterized by at least two of the following pain features: unilateral pain, throbbing pain, moderate to severe pain intensity, or pain exacerbated by physical activity. According to some embodiments, a pharmaceutical formulation comprising 70 mg or 140 mg of an erenumab composition described herein is administered to a patient once a month to treat, prevent, or reduce the occurrence of migraine headache in the patient. In such embodiments, the pharmaceutical formulation may be delivered by subcutaneous injection, for example, using one of the injection devices (e.g. pre-filled syringe or autoinjector) described above.

In some embodiments, the patients to be treated according to the methods of the invention have, suffer from, or are diagnosed with episodic migraine. Episodic migraine is diagnosed when patients with a history of migraine (e.g. at least five lifetime attacks of migraine headache) have 14 or fewer migraine headache days per month. A "migraine headache day" includes any calendar day during which a patient experiences the onset, continuation, or recurrence of a "migraine headache" with or without aura lasting greater than 30 minutes. In some embodiments, patients having, suffering from, or diagnosed with episodic migraine have at least four, but less than 15 migraine headache days per month on average. In related embodiments, patients having, suffering from, or diagnosed with episodic migraine have fewer than 15 headache days per month on average. As used herein, a "headache day" is any calendar day in which the patient experiences a migraine headache or any headache that lasts greater than 30 minutes or requires acute headache treatment. In certain embodiments, the patient may be classified as having or suffering from high-frequency episodic migraine. High-frequency episodic migraine patients are patients that have 8 to 14 migraine headache days per month. In other embodiments, the patient may be classified as having or suffering from low-frequency episodic migraine. Low-frequency episodic migraine patients are patients that have less than 8 migraine headache days per month.

In some embodiments, the patients to be treated according to the methods of the invention have, suffer from, or are diagnosed with chronic migraine. Chronic migraine is diagnosed when migraine patients (i.e. patients with at least five lifetime attacks of migraine headache) have 15 or more headache days per month and at least 8 of the headache days are migraine headache days. In some embodiments, patients having, suffering from, or diagnosed with chronic migraine have 15 or more migraine headache days per month on average.

In certain embodiments, migraine patients to be treated according to the methods of the invention have not previously received any prophylactic migraine therapies. In other embodiments, migraine patients to be treated according to the methods of the invention have failed or are intolerant to one or more prophylactic migraine therapies. In one such embodiment, the patient has failed to respond to prior therapy with at least one migraine headache prophylactic agent. "Failure to respond" or "treatment failure" refers to the lack of efficacy of the prophylactic agent in reducing the frequency, duration, and/or severity of migraine headache in the patient following a standard therapeutic regimen of the agent. For instance, in one embodiment, a patient who has failed prior treatment with a migraine prophylactic agent is a patient who experienced the same or a greater number of monthly migraine headache days following administration of the migraine prophylactic agent as compared to the number of monthly migraine headache days prior to treatment with the agent. Failure to respond to prior treatment with a migraine prophylactic agent can also include inability to tolerate the migraine prophylactic agent. For example, in some embodiments, a patient who has failed prior treatment with a migraine prophylactic agent is a patient who cannot tolerate the side effects associated with the agent. In such embodiments, the side effects associated with the agent may exacerbate or may be incompatible with another medical condition which the patient has. In certain embodiments, a patient has failed or is intolerant to treatment with one or more agents selected from beta-blockers (e.g., propranolol, timolol, atenolol, metoprolol, and nadolol), antiepileptics (e.g. divalproex, sodium valproate, valproic acid, topiramate, and gabapentin), tricyclic antidepressants (e.g., amitriptyline, nortriptyline, doxepin, and fluoxetine), and onabotulinumtoxinA.

The erenumab compositions described herein and pharmaceutical formulations comprising such compositions can also be used to treat, prevent, or reduce the occurrence of other types of headache disorders such as tension-type headaches, cluster headaches, hemiplegic migraine, menstrual migraine, and retinal migraine. Other diseases or conditions associated with CGRP/CGRP receptor signaling can also be treated or ameliorated with the erenumab compositions and pharmaceutical formulations comprising such compositions described herein. Diseases or conditions associated with CGRP/CGRP receptor signaling include, but are not limited to, chronic pain (e.g. nociceptive pain, neuropathic pain, inflammatory pain, fibromyalgia, arthritic pain), allodynia, inflammation (e.g. neurogenic inflammation, psoriasis, osteoarthritis), type II diabetes, overactive bladder, and asthma.

The pharmaceutical formulations of the invention are preferably administered to patients parenterally. Parenteral administration includes intraperitoneal, intramuscular, intravenous, intraarterial, intradermal, subcutaneous, intracerebral, intracerebroventricular, and intrathecal administration. In certain embodiments, the pharmaceutical formulations are administered to patients intravenously. In other embodiments, the pharmaceutical formulations are administered to patients subcutaneously, for example, by subcutaneous injection. The injections may be delivered to the patients using one or more of the devices (e.g. pre-filled syringes and autoinjectors) described herein.

The following are additional embodiments of the invention for exemplary purposes, and are not intended to be limiting in any way:

Embodiment 1

A composition comprising erenumab and one or more erenumab variants, wherein the one or more erenumab variants comprises an isomerization variant and a deamidation variant, and wherein the amount of the isomerization variant and deamidation variant in the composition is less than about 30%.

Embodiment 2

The composition of Embodiment 1, wherein the amount of the isomerization variant and deamidation variant in the composition is less than about 15%.

Embodiment 3

The composition of Embodiment 1, wherein the amount of the isomerization variant and deamidation variant in the composition is less than about 8%.

Embodiment 4

The composition of Embodiment 1, wherein the amount of the isomerization variant and deamidation variant in the composition is less than about 4%.

Embodiment 5

The composition of Embodiment 1, wherein the amount of the isomerization variant and deamidation variant in the composition is from about 1% to about 10%.

Embodiment 6

The composition of Embodiment 1, wherein the amount of the isomerization variant and deamidation variant in the composition is from about 1% to about 4%.

Embodiment 7

The composition of any one of Embodiments 1 to 6, wherein the isomerization variant has an isoaspartic acid residue or a succinimide at amino acid position 105 in either or both heavy chains (SEQ ID NO: 1 or SEQ ID NO: 3) of erenumab.

Embodiment 8

The composition of any one of Embodiments 1 to 7, wherein the deamidation variant has the asparagine residue at amino acid position 102 in either or both heavy chains (SEQ ID NO: 1 or SEQ ID NO: 3) of erenumab converted to an aspartic acid residue, a succinimide, or an isoaspartic acid residue.

Embodiment 9

The composition of any one of Embodiments 1 to 8, wherein the amount of the isomerization variant and deamidation variant in the composition is determined by hydrophobic interaction chromatography high performance liquid chromatography (HIC-HPLC).

Embodiment 10

A composition comprising erenumab and one or more erenumab acidic variants, wherein the amount of acidic variants in the composition is less than about 40%.

Embodiment 11

The composition of Embodiment 10, wherein the amount of acidic variants in the composition is less than about 35%.

Embodiment 12

The composition of Embodiment 10, wherein the amount of acidic variants in the composition is from about 25% to about 38%.

Embodiment 13

The composition of Embodiment 10, wherein the amount of acidic variants in the composition is from about 26% to about 34%.

Embodiment 14

The composition of any one of Embodiments 10 to 13, wherein one or more acidic variants comprise disulfide isoform variants, fragmentation variants, or combinations thereof.

Embodiment 15

The composition of any one of Embodiments 10 to 14, wherein the amount of acidic variants in the composition is determined by cation exchange high performance liquid chromatography (CEX-HPLC).

Embodiment 16

A composition comprising erenumab and one or more disulfide isoform variants thereof, wherein the one or more disulfide isoform variants comprise an IgG2-B isoform, and wherein the amount of the IgG2-B isoform in the composition is less than about 20%.

Embodiment 17

The composition of Embodiment 16, wherein the amount of the IgG2-B isoform in the composition is less than about 10%.

Embodiment 18

The composition of Embodiment 16, wherein the amount of the IgG2-B isoform in the composition is from about 4% to about 6%.

Embodiment 19

The composition of any one of Embodiments 16 to 18, wherein the one or more disulfide isoform variants further comprise an IgG2-AB isoform.

Embodiment 20

The composition of Embodiment 19, wherein the amount of the IgG2-A/B isoform in the composition is from about 34% to about 37%.

Embodiment 21

The composition of any one of Embodiments 16 to 20, wherein the amount of disulfide isoform variants in the composition is determined by non-reduced reversed phase high performance liquid chromatography (RP-HPLC).

Embodiment 22

A composition comprising erenumab and a high molecular weight (HMW) species of erenumab, wherein the amount of the HMW species in the composition is less than about 2.5%.

Embodiment 23

The composition of Embodiment 22, wherein the amount of the HMW species in the composition is about 1.8% or less.

Embodiment 24

The composition of Embodiment 22, wherein the amount of the HMW species in the composition is about 1.2% or less.

Embodiment 25

The composition of any one of Embodiments 22 to 24, wherein the HMW species comprises a covalently-linked dimer of erenumab.

Embodiment 26

The composition of any one of Embodiments 22 to 25, wherein the amount of the HMW species in the composition is determined by size exclusion ultra-high performance liquid chromatography (SE-UHPLC).

Embodiment 27

A composition comprising erenumab and one or more erenumab variants, wherein the erenumab variants comprise isomerization variants, deamidation variants, acidic variants, HMW species, or combinations thereof, wherein the composition has one or more of the following characteristics:
 (a) the amount of acidic variants in the composition is from about 25% to about 38% as measured by CEX-HPLC;
 (b) the amount of HMW species in the composition is about 2.1% or less as measured by SE-UHPLC; and
 (c) the amount of isomerization variants and deamidation variants in the composition is about 8% or less as measured by the pre-peaks in HIC-HPLC.

Embodiment 28

The composition of Embodiment 27, wherein the composition has one or more of the following characteristics:
 (a) the amount of acidic variants in the composition is from about 26.5% to about 33.6% as measured by CEX-HPLC;
 (b) the amount of HMW species in the composition is about 1.2% or less as measured by SE-UHPLC; and
 (c) the amount of isomerization variants and deamidation variants in the composition is about 3.2% or less as measured by the pre-peaks in HIC-HPLC.

Embodiment 29

The composition of any one of Embodiments 1 to 28, wherein erenumab comprises a heavy chain of SEQ ID NO: 1 and a light chain of SEQ ID NO: 2.

Embodiment 30

The composition of any one of Embodiments 1 to 28, wherein erenumab comprises a heavy chain of SEQ ID NO: 3 and a light chain of SEQ ID NO: 4.

Embodiment 31

A pharmaceutical formulation comprising the composition of any one of Embodiments 1 to 30 and one or more pharmaceutically acceptable excipients.

Embodiment 32

A method for treating, preventing, or reducing the occurrence of headache in a patient in need thereof comprising administering to the patient the pharmaceutical formulation of Embodiment 31.

Embodiment 33

The method of Embodiment 32, wherein the headache is migraine.

Embodiment 34

The method of Embodiment 33, wherein the migraine is episodic migraine or chronic migraine.

Embodiment 35

An erenumab composition of any one of Embodiments 1 to 30 for use in a method for treating, preventing, or reducing the occurrence of headache in a patient in need thereof.

Embodiment 36

The erenumab composition of Embodiment 35, wherein the headache is migraine.

Embodiment 37

The erenumab composition of Embodiment 36, wherein the migraine is episodic migraine or chronic migraine.

Embodiment 38

Use of an erenumab composition of any one of Embodiments 1 to 30 in the preparation of a medicament for treating, preventing, or reducing the occurrence of headache in a patient in need thereof.

Embodiment 39

The use of Embodiment 38, wherein the headache is migraine.

Embodiment 40

The use of Embodiment 39, wherein the migraine is episodic migraine or chronic migraine.

Embodiment 41

A method for assessing the quality of an erenumab composition, comprising:
 obtaining an erenumab composition that contains erenumab and one or more erenumab variants;
 measuring the amount of one or more erenumab variants in the composition, wherein the erenumab variants comprise isomerization variants, deamidation variants, acidic variants, HMW species, or combinations thereof;
 comparing the measured amount of the one or more erenumab variants to a pre-determined reference criterion; and
 preparing a pharmaceutical formulation or pharmaceutical product of the erenumab composition if the comparison indicates that the pre-determined reference criterion is met.

Embodiment 42

The method of Embodiment 41, wherein the amount of isomerization variants and deamidation variants is measured and the pre-determined reference criterion is about 10% or less.

Embodiment 43

The method of Embodiment 42, wherein the amount of isomerization variants and deamidation variants in the erenumab composition is measured by HIC-HPLC.

Embodiment 44

The method of Embodiment 41, wherein the amount of acidic variants is measured and the pre-determined reference criterion is about 38% or less.

Embodiment 45

The method of Embodiment 44, wherein the amount of acidic variants in the erenumab composition is measured by CEX-HPLC.

Embodiment 46

The method of Embodiment 41, wherein the amount of HMW species is measured and the pre-determined reference criterion is about 2.5% or less.

Embodiment 47

The method of Embodiment 46, wherein the amount of HMW species is measured by SE-UHPLC.

Embodiment 48

The method of any one of Embodiments 41 to 47, wherein the erenumab composition is obtained from a Chinese Hamster Ovary (CHO) cell line that expresses a nucleic acid encoding a heavy chain of SEQ ID NO: 1 and a nucleic acid encoding a light chain of SEQ ID NO: 2.

The following examples, including the experiments conducted and the results achieved, are provided for illustrative purposes only and are not to be construed as limiting the scope of the appended claims.

EXAMPLES

Example 1. Identification and Characterization of Erenumab Charge Variants by HIC-HPLC Erenumab is a fully human monoclonal antibody of the IgG2 subclass. The antibody is produced recombinantly in Chinese hamster ovary (CHO) cells and consists of two heavy chains and two light chains of the lambda subclass. Each heavy chain contains 456 amino acids with four intrachain disulfides. Each light chain contains 216 amino acids with two intrachain disulfides. Erenumab contains six interchain disulfides for a total of 18 intrachain and interchain disulfide bonds. The amino acid sequences for the heavy chain and light chain of erenumab are shown in FIGS. 1A and 1B, respectively. Each heavy chain contains an N-linked glycan at a consensus glycosylation site on the asparagine residue at position 306 of SEQ ID NO: 1. As is frequently observed for antibodies produced by mammalian cells, the C-terminal lysine residue at position 456 in the heavy chain is mostly removed by carboxypeptidases present during production in cell culture. In addition, the N-terminal glutamine residues on both the heavy and light chains is frequently converted to pyroglutamate during production. The amino acid sequences for the heavy chain and light chain of erenumab with these N- and C-terminal modifications are shown in FIGS. 1C and 1D, respectively. The calculated mass of deglycosylated erenumab with the C-terminal lysine removed from both heavy chains and full heavy and light chain N-terminal pyroglutamate formation is 145,872 Daltons.

Erenumab specifically binds to the extracellular domain of the calcitonin gene-related peptide (CGRP) receptor and prevents CGRP from binding to and activating the receptor. CGRP is a neuropeptide that modulates nociceptive signaling and is a vasodilator that has been associated with migraine pathophysiology. Erenumab potently and specifically competes with the binding of CGRP to the CGRP receptor and inhibits CGRP-induced activation of the intracellular cyclic adenosine monophosphate (cAMP) signaling cascade. Erenumab does not exhibit any significant pharmacological activity at adrenomedullin, calcitonin, or amylin receptors and lacks agonist activity at the CGRP receptor.

Biochemical, biophysical, and biological characterization of erenumab drug substance produced by the commercial-scale manufacturing process was conducted to elucidate the structural and functional properties of the drug substance. This example describes the identification and characterization of charge variants of erenumab that exhibited reduced CGRP receptor inhibitory function. Charge heterogeneity of erenumab in this example was evaluated by hydrophobic interaction chromatography high performance liquid chromatography (HIC-HPLC).

HIC-HPLC separates proteins based primarily on the surface hydrophobicity of a molecule and may also be influenced by structural heterogeneity and other modifications that impact molecular interactions with the column matrix. Peak elution in HIC-HPLC is a function of net surface hydrophobicity with molecules with higher surface hydrophobicity eluting later than molecules with lower surface hydrophobicity.

Samples of erenumab drug substance were loaded onto a hydrophobic interaction chromatography column (ProPac HIC-10, 5 μm particle size, 4.6 mm×250 mm, ThermoFisher Scientific). Mobile phase A contained 10 mM sodium acetate, 1 M ammonium sulfate at pH 5.5 and mobile phase B consisted of 10 mM sodium acetate at pH 5.5. Proteins were separated in a decreasing salt gradient generated with 25% to 100% mobile phase B from 0 min to 52 min, and back to 25% mobile phase B at 55.5 min to 75 min. The eluent was monitored by UV absorbance at 280 nm. The column was operated at 35° C. and the mobile phase was applied to the column at a flow rate of 0.5 mL/min.

Figure 2B:
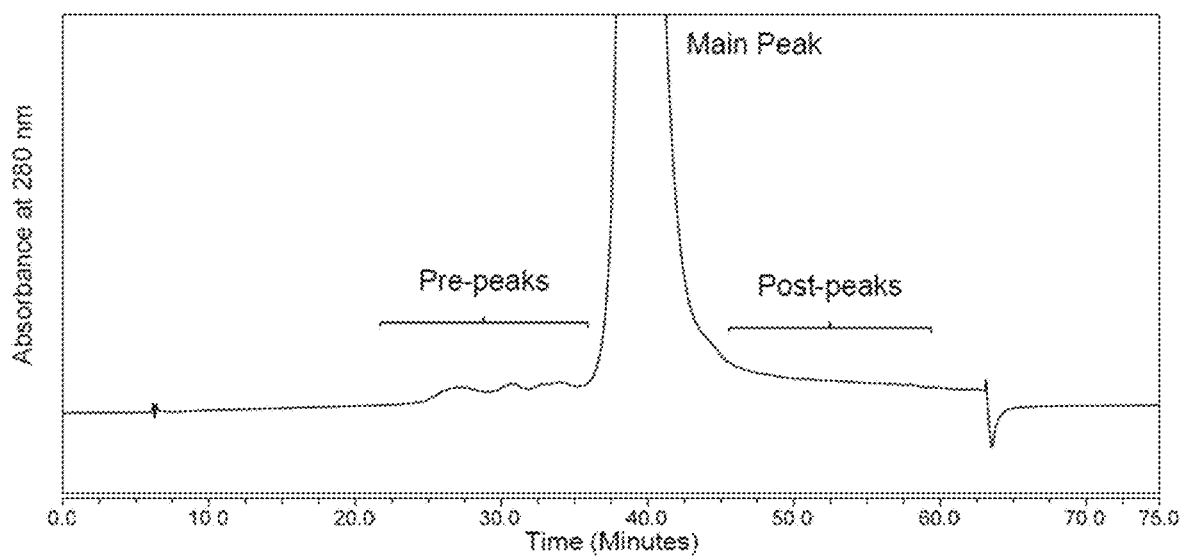
Figure 3A:
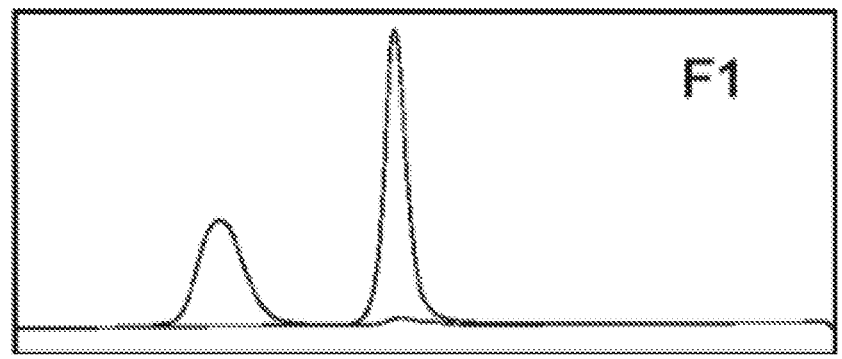
FIGS. 3A-3H show overlays of HIC-HPLC collected fractions and erenumab drug substance analyzed by HIC-HPLC. Erenumab drug substance and fractions collected from semi-preparative HIC-HPLC (F1-F7.
Figure 3B:
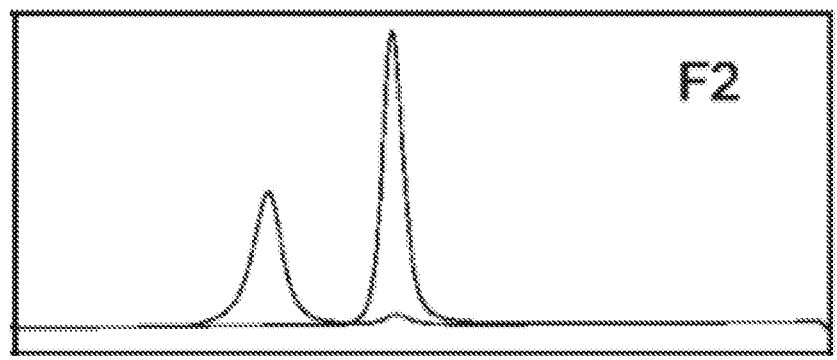
Figure 3C:
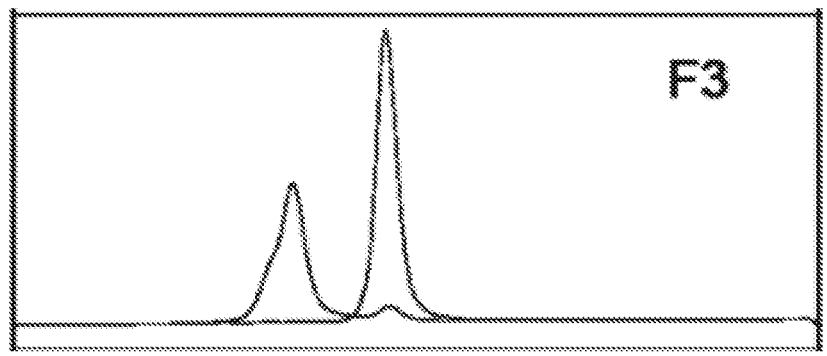
Figure 3D:
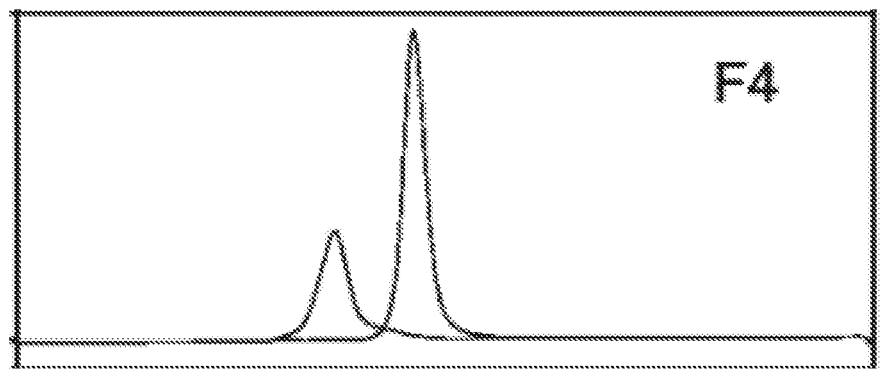
Figure 3E:
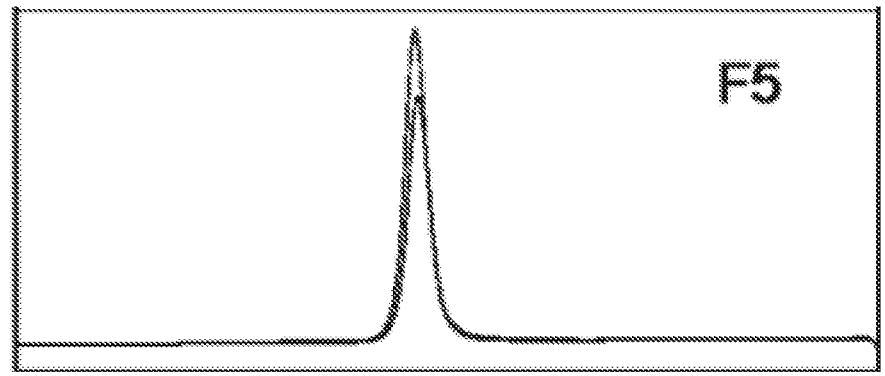
Figure 3F:
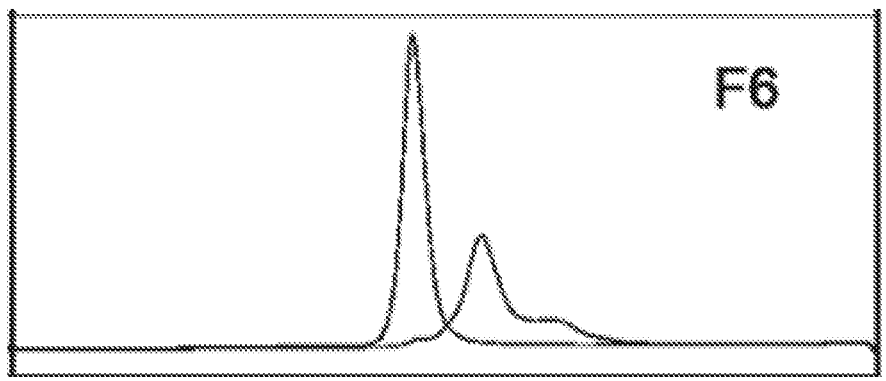
Figure 3G:
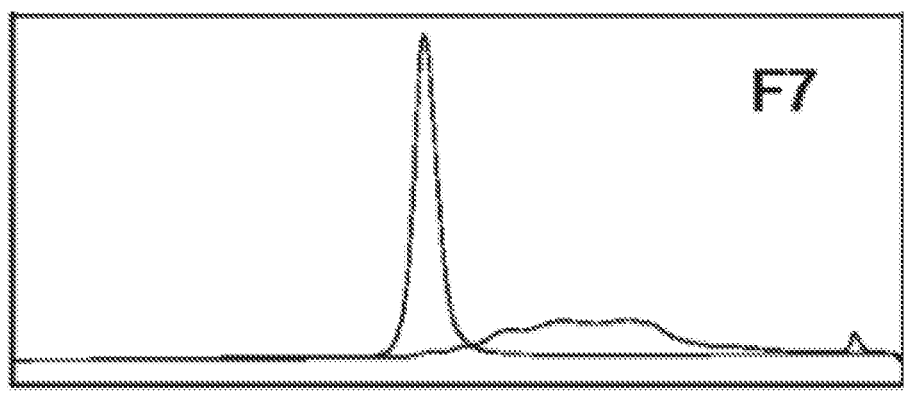
Figure 3H:
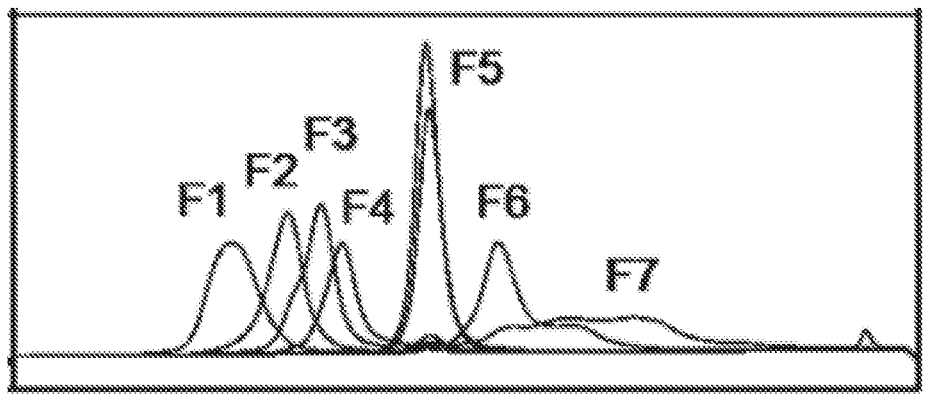

The HIC-HPLC profile contained three distinct regions, including pre-peaks, main peak, and post-peaks (FIGS. 2A and 2B). Seven fractions across the pre-peak, main peak, and post-peak regions were isolated. The collected fractions were re-analyzed by HIC-HPLC to demonstrate that the fractions were of sufficient purity for characterization. HIC-HPLC profiles and purities of the isolated fractions are shown in FIGS. 3A-3H and Table 1, respectively.

TABLE 1

HIC-HPLC Peak Area Percentage of Enriched Fractions[1]

| Sample Description | Pre-peaks | | | | Main Peak | Post-peaks | |
|---|---|---|---|---|---|---|---|
| | % F1 | % F2 | % F3 | % F4 | % F5 | % F6 | % F7 |
| Drug Substance | 0.7 | 0.5 | 0.3 | 0.4 | 94.0 | 1.5 | 2.4 |
| Pre-peak Fraction F1 | 94.3 | — | — | — | 5.7 | — | — |
| Pre-peak Fraction F2 | — | 93.5 | — | — | 6.5 | — | — |
| Pre-peak Fraction F3 | — | 17.8 | 72.9 | — | 9.3 | — | — |
| Pre-peak Fraction F4 | — | — | — | 88.1 | 11.9 | — | — |
| Main Fraction F5 | — | — | — | — | 100.0 | — | — |
| Post-peak Fraction F6 | — | — | — | — | 9.8 | 69.8 | 20.4 |
| Post-peak Fraction F7 | — | — | — | — | 5.6 | 15.3 | 79.1 |

[1]All HIC-HPLC fractions were collected from the same drug substance lot. Fraction of interest based on the collection time window and relative purity emphasized and underlined. Peaks not detected are denoted with a dash.

The pre-peak, main peak, and post-peak fractions in FIGS. 3A-3H and Table 1 were characterized by various analytical techniques, including size exclusion ultra-high performance liquid chromatography (SE-UHPLC), reduced tryptic peptide mapping with LC-MS/MS, and a cell-based bioassay.

Unfractionated drug substance and the seven HIC-HPLC fractions were analyzed by SE-UHPLC using a BEH200 analytical UHPLC column (1.7 µm particle size, 4.6 mm×150 mm, Waters Corporation) and a mobile phase comprising 100 mM sodium phosphate, 250 mM sodium chloride, pH 6.8. The SE-UHPLC analysis revealed that all pre-peak and post-peak fractions were enriched in high molecular weight (HMW) species, whereas only the earliest pre-peak fraction (F1) and latest post-peak fraction (F7) were enriched in low molecular weight (LMW) species relative to the unfractionated drug substance (Table 2).

TABLE 2

SE-UHPLC Peak Area Percentage of Enriched HIC-HPLC Fractions

| Sample Description | % HMW | % Main | % LMW |
|---|---|---|---|
| Drug Substance | 0.4 | 99.4 | <0.3[1] |
| Pre-peak Fraction F1 | 5.1 | 93.3 | 1.6 |
| Pre-peak Fraction F2 | 2.8 | 96.7 | 0.5 |
| Pre-peak Fraction F3 | 2.8 | 96.7 | 0.5 |
| Pre-peak Fraction F4 | 5.0 | 94.7 | 0.3 |
| Main Fraction F5 | 0.6 | 99.3 | <0.3[1] |
| Post-peak Fraction F6 | 12.7 | 87.0 | 0.3 |
| Post-peak Fraction F7 | 16.8 | 80.8 | 2.4 |

[1]Limit of Quantitation = 0.3%

Biochemical modifications of erenumab present in the enriched pre-peak, main peak, and post-peak fractions, as well as the non-fractionated drug substance were assessed by reduced tryptic peptide mapping with detection by electrospray ionization tandem mass spectrometry (ESI-MS/MS). Drug substance and the seven HIC-HPLC fractions were denatured in a 7.5 M guanidine hydrochloride solution and treated with 0.5 M of the reducing agent dithiothreitol (DTT), and all cysteine residues were alkylated by the addition of 0.5 M sodium iodoacetate (IAA). The reduced and alkylated samples were desalted by gel filtration followed by digestion at 37° C. with trypsin for 35 minutes. The digested samples were separated by reversed phase high performance liquid chromatography (RP-HPLC) using a C18 column (1.8 µm particle size, 2.1 mm×150 mm) and a 0.1% TFA mobile phase with an acetonitrile gradient at a flow rate of 0.3 mL/min. Detection of peptides was by ultraviolet (UV) light absorbance at 215 nm with identification of peaks by online ESI-MS/MS. The fragmentation pattern of each peptide ion was then examined against its expected MS/MS spectrum.

Figure 4:
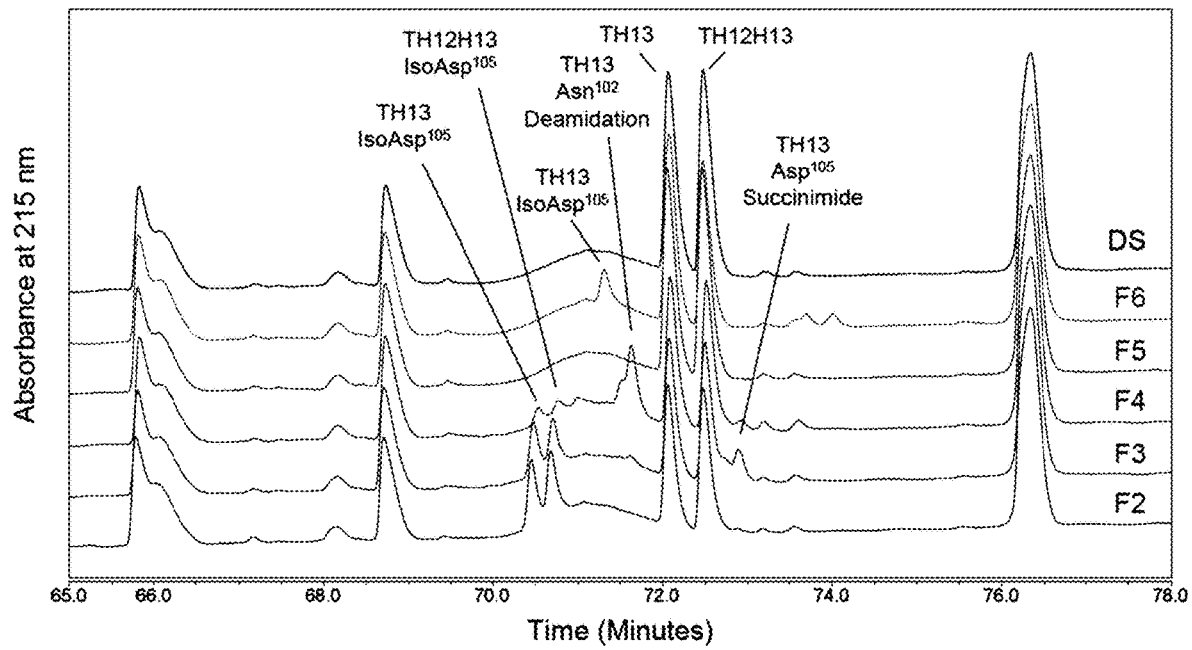
FIG. 4 is a reduced tryptic peptide map overlay of the elution region for peptides within the erenumab heavy chain CDR3 for enriched HIC-HPLC fractions (F2-F6) and unfractionated erenumab drug substance (DS). TH12H13 peptide corresponds to amino acid residues 99 to 113 of SEQ ID NO: 1 and TH13 corresponds to amino acid residues 101 to 113 of SEQ ID NO: 1.

An overlay of the drug substance and enriched fractions is presented in FIG. 4 displaying the elution region for two peptides within the heavy chain CDR3: TH12H13 (amino acid residues 99 to 113 of SEQ ID NO: 1) and TH13 (amino acids residues 101 to 113 of SEQ ID NO: 1). Pre-peak fractions F2, F3 and F4 and post-peak fraction F6 all showed variations in the CDR3 peptide (TH13) relative to the drug substance. No differences in the TH13 peptide were observed for fractions F1 and F7. Pre-peak fractions F2, F3, and F4 and post-peak fraction F6 were enriched in both deamidation and isomerization variants (isoaspartate (IsoAsp) and a succinimide intermediate) within the heavy chain CDR3 peptide TH13. Deamidation of the asparagine residue at position 102 and isomerization of the aspartic acid residue at position 105 (both positions with respect to SEQ ID NO: 1) were observed. Two separate peptides identified as IsoAsp105 were observed eluting at different retention times. These peptides are likely structural enantiomers generated during aspartic acid isomerization. An additional TH13 peptide variant was also observed corresponding to the succinimide intermediate at position 105 eluting after the native peptide. Modification levels were approximated by comparing the extracted ion chromatogram (EIC) peak areas of the modified peptides to those generated from the unmodified peptides. Mass analysis confirmed the presence of elevated deamidation and IsoAsp variants within the pre-peak and post-peak regions (Table 3).

TABLE 3

Summary of Observed Modifications of Enriched HIC-HPLC Fractions by Reduced Tryptic Peptide Map

| Sample Description | % $Asp^{105}$ Isomerization[1] | % $Asp^{105}$ Succinimide | % $Asn^{102}$ Deamidation | % $Leu^{195}/Ser^{196}$ Cleavage |
|---|---|---|---|---|
| Drug Substance | ND | 0.2 | ND | 0.4 |
| Pre-peak Fraction F1 | 0.6 | 0.2 | ND | 10.9 |
| Pre-peak Fraction F2 | 26.4 | 1.4 | 0.1 | 1.0 |
| Pre-peak Fraction F3 | 19.6 | 12.6 | 1.2 | 0.5 |
| Pre-peak Fraction F4 | 5.5 | 4.3 | 11.6 | 0.4 |
| Main Fraction F5 | ND | 0.1 | ND | 0.3 |

TABLE 3-continued

Summary of Observed Modifications of Enriched HIC-HPLC Fractions by Reduced Tryptic Peptide Map

| Sample Description | % $Asp^{105}$ Isomerization[1] | % $Asp^{105}$ Succinimide | % $Asn^{102}$ Deamidation | % $Leu^{195}/Ser^{196}$ Cleavage |
|---|---|---|---|---|
| Post-peak Fraction F6 | 13.2 | 0.1 | ND | 0.6 |
| Post-peak Fraction F7 | 2.4 | 0.1 | ND | 1.1 |

ND = not detected
[1]Sum of both $IsoAsp^{105}$ TH13 variants eluting at approximately 70.5 min and 71.5 min in FIG. 4.

Pre-peak fraction F1 was reduced and analyzed by ESI-TOF mass spectrometry as analysis of this fraction by rCE-SDS had previously shown significant levels of LMW and middle molecular weight (MMW) species. A total of six cleavage fragments were identified in pre-peak fraction F1, of which four cleavage sites ($Leu^{315}/Thr^{316}$; $Ser^{197}/Val^{198}$; $Leu^{195}/Ser^{196}$; and $Leu^{192}/Tyr^{193}$) were within the heavy chain CH1 and CH2 domains. Two cleavage sites ($Gly^{108}/Tyr^{109}$ and $Asp^{105}/Ser^{106}$) were also identified in the CDR3 of the heavy chain. For all species, only the C-terminal fragment was detected. Elevated levels of the $Leu^{195}/Ser^{196}$ cleavage fragment were observed within the pre-peak fraction F1 relative to drug substance (Table 3).

The biological activity of the enriched HIC-HPLC fractions compared to erenumab drug substance was evaluated by a cell-based bioassay. The cell-based bioassay assesses the potency of erenumab by measuring the ability of erenumab to inhibit ligand-induced activation of the human CGRP receptor. The CGRP receptor is a G-protein coupled receptor and this family of receptors has been shown to produce cAMP intracellularly as part of its signal transduction mechanism. A stable Chinese Hamster Ovary K1 (CHO-K1) cell line expressing the human CGRP receptor (CHO-K1 huCGRP) was incubated with CGRP ligand and varying concentrations of an erenumab Reference Standard and test samples. The amount of cAMP generated by the cells following incubation with CGRP in the presence or absence of erenumab Reference Standard and test samples was measured using a competitive homogenous time-resolved fluorescence energy transfer (TR-FRET) assay, in which a detectable signal is generated when the labeled assay components (cAMP labeled with Alexa Fluor® 647 dye and an anti-cAMP monoclonal antibody-cryptate) bind to each other. When cAMP is produced intracellularly by activation of the CGRP receptor by CGRP, the native cAMP produced by the cells competes with the Alexa Fluor® 647 dye-labeled cAMP for binding to the cryptate-labeled anti-cAMP monoclonal antibody and the detectable signal is reduced. Thus, due to the competitive nature of the TR-FRET cAMP assay, the signal generated is inversely proportional to the concentration of cAMP in the cells. The TR-FRET signal was measured by a plate reader. The activity of the test samples was determined by comparing the signal generated with the test samples to the signal generated with the erenumab Reference Standard and is reported as a relative potency.

As shown in Table 4 below, all pre-peak fractions showed significant reductions in potency. These reductions are due to either high levels of fragmentation (for F1 fraction) or deamidation and isomerization in the heavy chain CDR3 region (for fractions F2-F4), which are the predominant variants in the pre-peak fractions as described above. The post-peak fractions also showed a reduction in potency, likely as a result of elevated HMW species and low levels of heavy chain CDR3 aspartic acid ($Asp^{105}$) isomerization, which are the predominant variants in the post-peak fractions as described above.

TABLE 4

Potency of Enriched HIC-HPLC Fractions

| Sample Description | % Relative Potency by Cell-Based Bioassay[1] | % CV |
|---|---|---|
| Drug Substance | 100 | 6 |
| Pre-peak Fraction F1 | 33 | 8 |
| Pre-peak Fraction F2 | 24 | 4 |
| Pre-peak Fraction F3 | 35 | 1 |
| Pre-peak Fraction F4 | 34 | 3 |
| Main Fraction F5 | 107 | 2 |
| Post-peak Fraction F6 | 77 | 4 |
| Post-peak Fraction F7 | 68 | 3 |

[1]Average of 3 replicates

The results of the analyses described in this example demonstrated that the HIC-HPLC profile of erenumab drug substance contained three distinct regions, including pre-peaks, main peak and post-peaks. The primary erenumab variants detected by HIC-HPLC include heavy chain CDR3 aspartic acid isomerization (e.g. isomerization of $Asp^{105}$ of SEQ ID NO: 1) and deamidation (e.g. deamidation of $Asn^{102}$ of SEQ ID NO: 1) variants in both the pre-peak and post-peak regions. Fragmented species were observed in the pre-peak group and elevated levels of HMW species were observed in the post-peak group. The potencies of all erenumab HIC-HPLC pre-peak and post-peak fractions were lower than the drug substance, as evaluated by the cell-based bioassay. The pre-peaks showed a significant reduction in potency as a result of aspartic acid isomerization and deamidation in the heavy chain CDR3 region as well as high levels of fragmentation variants. The post-peaks also showed reduced potency as a result of elevated levels of HMW species and heavy chain CDR3 isomerization variants.

Because the presence of heavy chain CDR3 aspartic acid isomerization and asparagine deamidation variants of erenumab impacted the inhibitory potency of the composition, several lots of erenumab drug substance (140 mg/mL) manufactured at commercial scale were analyzed by HIC-HPLC to assess the presence and quantity of the isomerization and deamidation variants as measured by the peak area percentage of the pre-peaks in the HIC-HPLC chromatogram. Potency of the drug substance lots was also evaluated by the cell-based potency assay described above and compared to the potency of Lot No. 78137, which is representative of the erenumab drug substance employed in Phase II/Phase III clinical trials. A summary of the data is provided in Table 5 below.

TABLE 5

HIC-HPLC and Potency Data for Erenumab Drug Substance Lots

| Lot Number | HIC-HPLC % Main Peak | HIC-HPLC % Pre-Peaks | Cell-Based Bioassay % Relative Potency |
|---|---|---|---|
| 78137 (clinical trial material) | — | — | 101 |
| 63130 | 98.3 | 1.7 | 98 |
| 63131 | 98.2 | 1.8 | 124 |
| 63132 | 98.0 | 2.0 | 92 |
| 63133 | 98.2 | 1.8 | 96 |
| 63134 | 97.9 | 2.1 | 101 |

As shown by the data in Table 5, erenumab drug substance manufactured at commercial scale contained a consistent level of isomerization and deamidation variants ranging from 1.7% to 2.1% as measured by HIC-HPLC pre-peaks. Drug substance that contained levels of deamidated/isomerized variants in this range exhibited a potency that was comparable to the potency of the erenumab drug substance employed in clinical trials.

Example 2. Evaluation of Erenumab Isomerization and Deamidation Variants Under Various Storage Conditions Deamidation of $Asn^{102}$ and conversion of $Asp^{105}$ to isoaspartate was observed in the CDR3 of the erenumab heavy chain during manufacture of the drug substance (Example 1). Erenumab variants having these modifications exhibited reduced potency as compared to the unmodified forms of erenumab (Example 1). To further evaluate the impact of the $Asn^{102}$ deamidation and $Asp^{105}$ isomerization variants on potency of the erenumab drug substance, erenumab drug substance was subject to stress conditions to increase the formation of the deamidation and isomerization variants and the potency of the stressed drug substance was assessed. Specifically, erenumab drug substance was subject to the following three stress conditions to facilitate the generation of the deamidation and isomerization variants:

Thermal exposure (50° C. for 14 days)

Physiological pH and temperature (pH 7.4 at 37° C. for 14 days)

High pH exposure (pH 8.0 at 25° C. for 14 days)

The formation of the deamidation and isomerization variants induced by each stress condition over time was monitored by the HIC-HPLC and reduced tryptic peptide mapping methods described in Example 1. For each stress condition, samples were removed at various time points over the duration of the study and frozen. After the final time point, all samples were analyzed side-by-side to minimize analytical variability.

Thermal Exposure

Figure 5:
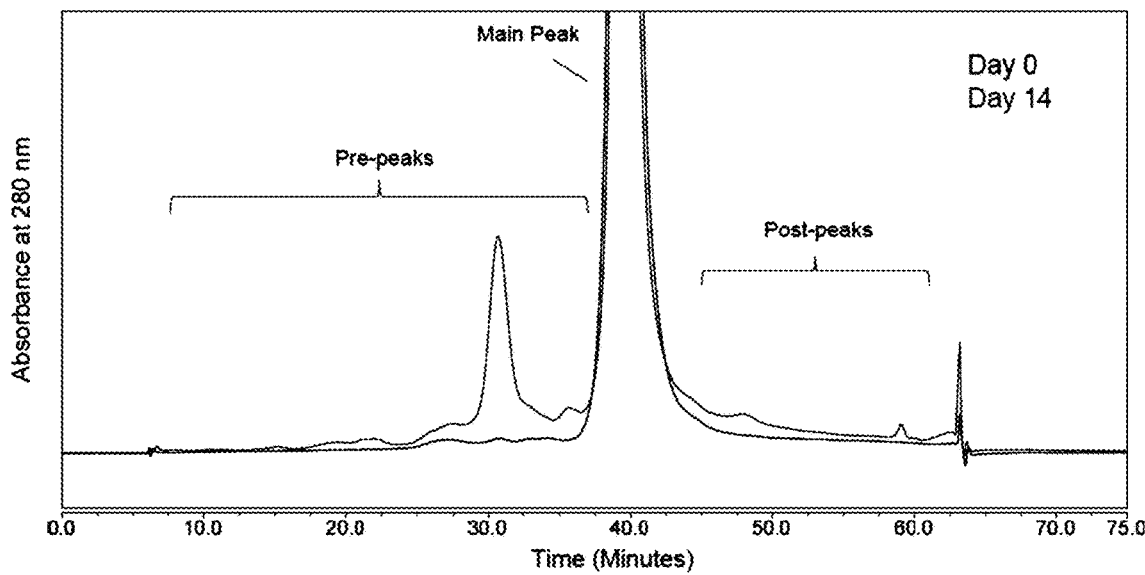
FIG. 5 is a HIC-HPLC profile of erenumab drug substance exposed to thermal stress. Erenumab drug substance incubated at 50° C. for 14 days was analyzed by HIC-HPLC using a sodium acetate, pH 5.5 mobile phase with elution by a linear gradient of ammonium sulfate and detection at 280 nm absorbance. The top trace corresponds to the Day 14 time point.

The results of the HIC-HPLC analysis of erenumab drug substance stressed at 50° C. showed a significant increase in pre-peaks (FIG. 5 and Table 6). This increase in pre-peaks is due primarily to an increase in aspartic acid isomerization after 14 days of exposure to thermal stress as revealed by the reduced tryptic peptide mapping analysis explained in detail below. An increase in post-peaks was also observed likely due to increased levels of HMW species as these elute as part of the later-eluting post-peaks as shown in Table 2 in Example 1.

TABLE 6

HIC-HPLC Peak Area % of Erenumab Stressed at 50° C.

| Time Point (Days) | % Pre-peaks | % Main Peak | % Post-peaks |
|---|---|---|---|
| 0 | 1.9 | 98.1 | 0.0 |
| 14 | 16.8 | 79.1 | 4.2 |

Figure 6:
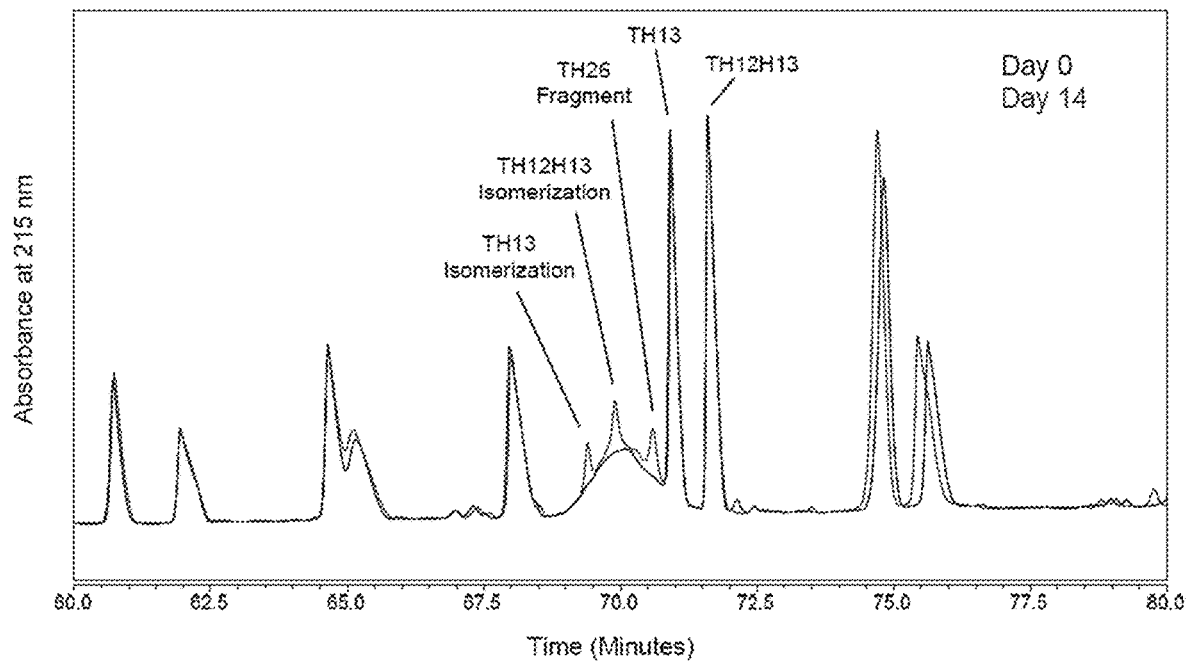
FIG. 6 depicts a reduced tryptic peptide map profile at expanded scale for erenumab drug substance stressed at 50° C. for 14 days. TH12H13 peptide corresponds to amino acid residues 99 to 113 of SEQ ID NO: 1 and TH13 corresponds to amino acid residues 101 to 113 of SEQ ID NO: 1. TH26 peptide corresponds to amino acid residues 311 to 326 of SEQ ID NO: 1 and the fragment detected is due to non-specific cleavage between $L^{315}$ and $T^{316}$.

The peptide map chromatograms were evaluated for the presence of new peaks or significant changes in the peak areas of existing peaks over the time of exposure. An expanded scale overlay of the day 0 and the day 14 samples highlighting the regions where differences were observed is shown in FIG. 6. Aspartic acid isomerization at $Asp^{105}$ in the heavy chain CDR3 (peptides TH12H13 and TH13) was the predominant degradant observed in the peptide map overlays. The hydrolysis fragment of peptide TH26 (corresponding to amino acid residues 311 to 326 of SEQ ID NO: 1) between $Leu^{315}$ and $Thr^{316}$ in the Fc region was also observed in the day 14 sample chromatogram.

The biological activity of erenumab drug substance exposed to thermal stress conditions was evaluated by the cell-based bioassay described in Example 1. As shown in Table 7, thermal stress had a negative impact on the relative potency of erenumab drug substance after exposure to 50° C. for 14 days. The reduction in potency after thermal stress is due to the increase in $Asp^{105}$ isomerization variants and high molecular weight species, both of which have been shown to impact potency (see Example 1 and Example 5).

TABLE 7

Relative Potency of Erenumab Exposed to Thermal Stress

| Time Point (Days) | % Relative Potency by Cell-Based Bioassay[1] | % CV |
|---|---|---|
| 0 | 93 | 4 |
| 14 | 71 | 7 |

[1]Average of 3 replicates

Physiological pH and Temperature

Erenumab drug substance was exposed to physiological pH by dilution to approximately 10 mg/mL with a phosphate buffered saline (PBS) solution at pH 7.4 and incubated at 37° C. (physiological temperature) for 14 days. A pH control, which was drug substance diluted in formulation buffer (15 mM sodium acetate, 8.2% (w/v) sucrose, 0.010% (w/v) polysorbate 80), pH 5.2, was incubated at 37° C. over the 14 days. Thus, the "physiological pH stressed sample" was exposed to both a pH and thermal stress, whereas the "pH control sample" was exposed only to a thermal stress.

Figure 7:
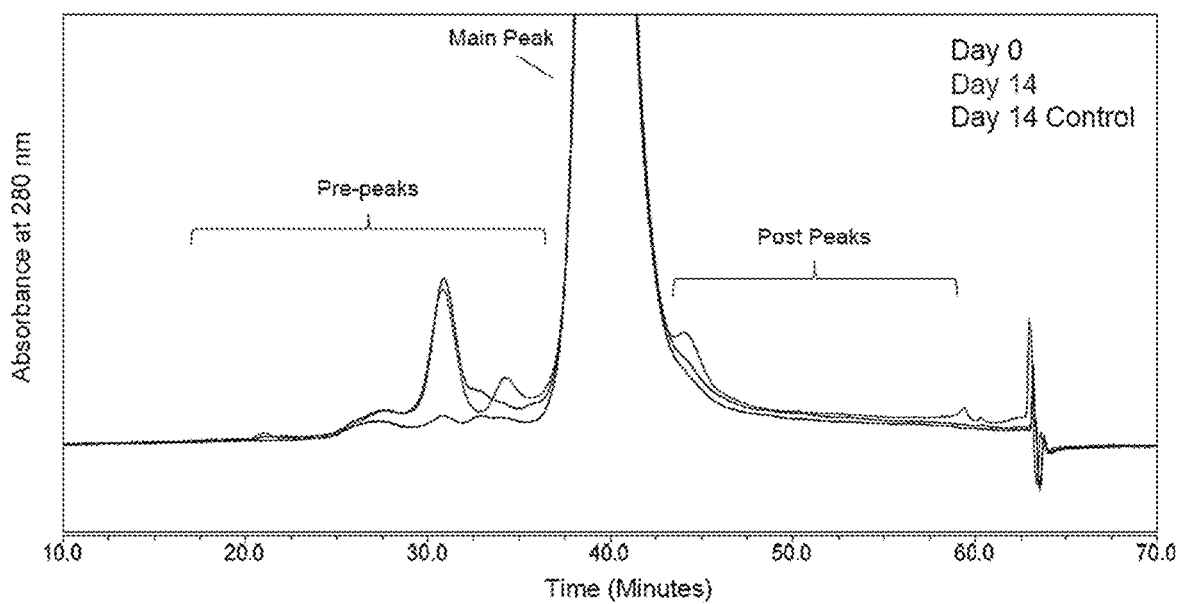
FIG. 7 is a HIC-HPLC profile of erenumab drug substance stressed at pH 7.4 and 37° C. Erenumab drug substance diluted to 10 mg/mL with PBS, pH 7.4 and incubated at 37° C. for 14 days was analyzed by HIC-HPLC using a sodium acetate, pH 5.5 mobile phase with elution by a linear gradient of ammonium sulfate and detection at 280 nm absorbance. Control sample was diluted in formulation buffer, pH 5.2, and incubated at 37° C. for 14 days along with the physiological pH stress condition sample.

Comparison of the HIC-HPLC profiles for the day 14 physiological pH stressed sample to the day 0 sample showed an increase in both pre-peaks and post-peaks (FIG. 7 and Table 8). The day 14 traces from the physiological pH stressed sample and the pH control sample showed similar levels of the pre-peak eluting at approximately 30 minutes, which corresponds to the $Asp^{105}$ isomerization variant, suggesting this isoaspartate variant is driven primarily by thermal stress rather than pH stress. The pre-peak eluting at approximately 34 minutes, which corresponds to the $Asn^{102}$ deamidated variant, increased in the day 14 physiological pH stressed sample and not in the pH control, indicating deamidation of $Asn^{102}$ is primarily driven by pH stress rather than thermal stress. An increase in post-peaks was also observed in the day 14 physiological pH stressed sample relative to both the day 0 sample and the day 14 pH control sample, indicating the change is driven primarily by pH stress.

TABLE 8

HIC-HPLC Peak Area % of Erenumab Stressed at pH 7.4 and 37° C.

| Time Point (Days) | % Pre-peaks | % Main Peak | % Post-peaks |
|---|---|---|---|
| 0 | 1.6 | 98.4 | 0.0 |
| 14 | 6.0 | 89.7 | 4.3 |
| 14 (Control) | 5.3 | 94.7 | 0.0 |

Biochemical modifications of the erenumab drug substance stressed at physiological pH and temperature were monitored by reduced peptide mapping with mass spectrometry (MS) after digestion with trypsin. Analysis of the MS data showed an increase in deamidation in both the heavy chain CDR3 (Asn$^{102}$) and Fc region (Asn$^{393}$ and Asn$^{398}$) as well as increased amounts of heavy chain CDR3 Asp$^{105}$ isomerization (data not shown). The increased level of heavy chain CDR3 Asp$^{105}$ isomerization and Asn$^{102}$ deamidation are consistent with the observed increase in pre-peaks and post-peaks by HIC-HPLC shown in FIG. 7 and Table 8.

The biological activity of the erenumab drug substance stressed at physiological pH and temperature was evaluated by the cell-based bioassay. As shown in Table 9, the physiological pH and temperature stress produced a reduction in potency of erenumab drug substance after 14 days of exposure. Although an increase in the levels of Asn$^{102}$ deamidation and Asp$^{105}$ isomerization variants was observed under these stress conditions, only a modest potency reduction was observed. This result is likely due to the overall levels of these deamidation and isomerization variants, which accounted for about 6% of the drug substance, being too low to significantly impact the potency as measured by the cell-based bioassay.

TABLE 9

Relative Potency of Erenumab Stressed at pH 7.4 and 37° C.

| Time Point (Days) | % Relative Potency by Cell-Based Bioassay[1] | % CV |
|---|---|---|
| 0 | 94 | 3 |
| 14 | 86 | 1 |

[1]Average of 3 replicates

High pH Exposure

Erenumab drug substance was exposed to high pH by dilution to approximately 10 mg/mL with a Tris base solution, pH 8.0 and incubation at 25° C. for 14 days. A pH control, which was drug substance diluted in formulation buffer (15 mM sodium acetate, 8.2% (w/v) sucrose, 0.010% (w/v) polysorbate 80), pH 5.2, was incubated at 25° C. over the 14 days.

Figure 8:
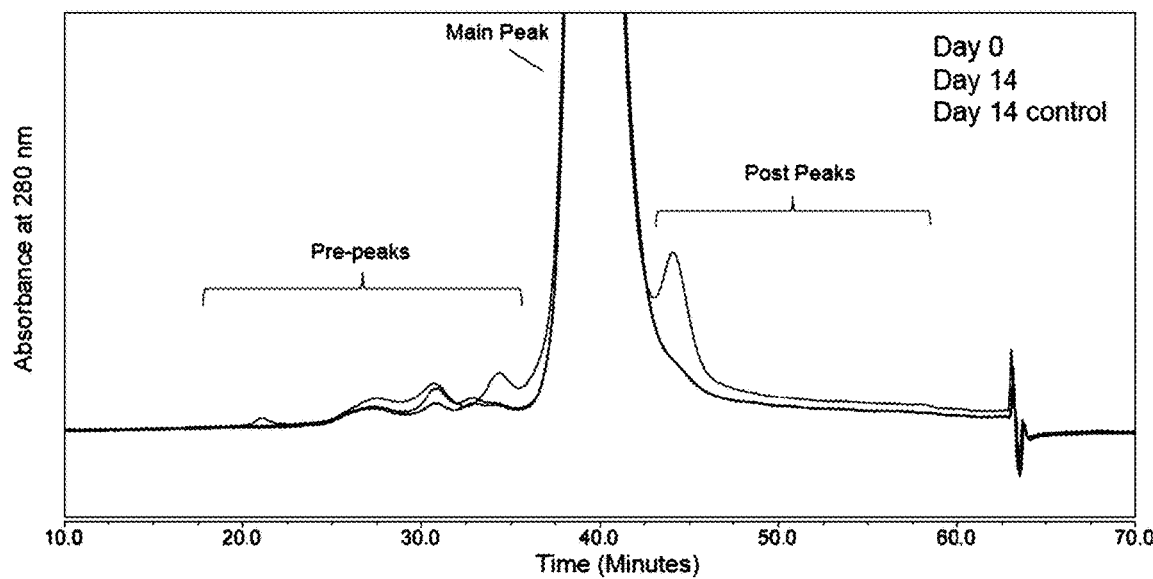
FIG. 8 is a HIC-HPLC profile of erenumab drug substance stressed at pH 8.0 and 25° C. Erenumab drug substance diluted to 10 mg/mL with Tris base, pH 8.0 and incubated at 25° C. for 14 days was analyzed by HIC-HPLC using a sodium acetate, pH 5.5 mobile phase with elution by a linear gradient of ammonium sulfate and detection at 280 nm absorbance. Control sample was diluted in formulation buffer, pH 5.2, and incubated at 25° C. for 14 days along with the high pH stress condition sample.

The results of the HIC-HPLC analysis showed an increase in pre-peaks due to Asn$^{102}$ deamidation as well as an increase in post-peaks in the day 14 high pH-stressed sample relative to the day 0 sample and the pH control sample (FIG. 8 and Table 10).

TABLE 10

HIC-HPLC Peak Area % of Erenumab Stressed at pH 8.0 and 25° C.

| Time Point (Days) | % Pre-peaks | % Main Peak | % Post-peaks |
|---|---|---|---|
| 0 | 2.1 | 97.9 | 0.0 |
| 14 | 3.6 | 89.8 | 6.5 |
| 14 (Control) | 2.6 | 97.4 | 0.0 |

Biochemical modifications of the erenumab drug substance stressed at high pH were monitored by reduced peptide mapping with MS after digestion with trypsin. As with the physiological pH stress conditions, an increase in deamidation in the heavy chain CDR3 at Asn$^{102}$ as well as within the Fc region at Asn$^{393}$ and Asn$^{398}$ was observed for the day 14 stress sample relative to the day 0 and pH control samples. The biological activity of the erenumab drug substance stressed at high pH was evaluated by the cell-based bioassay. As shown in Table 11, the high pH stress had a modest impact on potency of erenumab drug substance after 14 days of exposure. Similar to the results obtained with the physiological pH and temperature stress conditions, the overall level of Asn$^{102}$ deamidation variant present in the stressed drug substance was too low to have a significant impact on the potency as measured by the cell-based bioassay.

TABLE 11

Relative Potency of Erenumab Stressed at pH 8.0 and 25° C.

| Time Point (Days) | % Relative Potency by Cell-Based Bioassay[1] | % CV |
|---|---|---|
| 0 | 89 | 5 |
| 14 | 79 | 3 |

[1]Average of 3 replicates

To better ascertain the levels of Asn$^{102}$ deamidation and Asp$^{105}$ isomerization variants required to significantly reduce potency of the erenumab drug substance, a statistical analysis modeling the relationship between potency and HIC-HPLC pre-peak area percentage was conducted with data available from different erenumab lots stored at different temperatures. Erenumab lots were stored at 5° C. (13 lots), 25° C. (4 lots), 30° C. (4 lots), or 40° C. (5 lots). For the data from the 5° C. storage condition, there were 6 lots with only one time point, and 9 lots with only two time points. All other storage conditions had data from at least three different time points.

Figure 9:
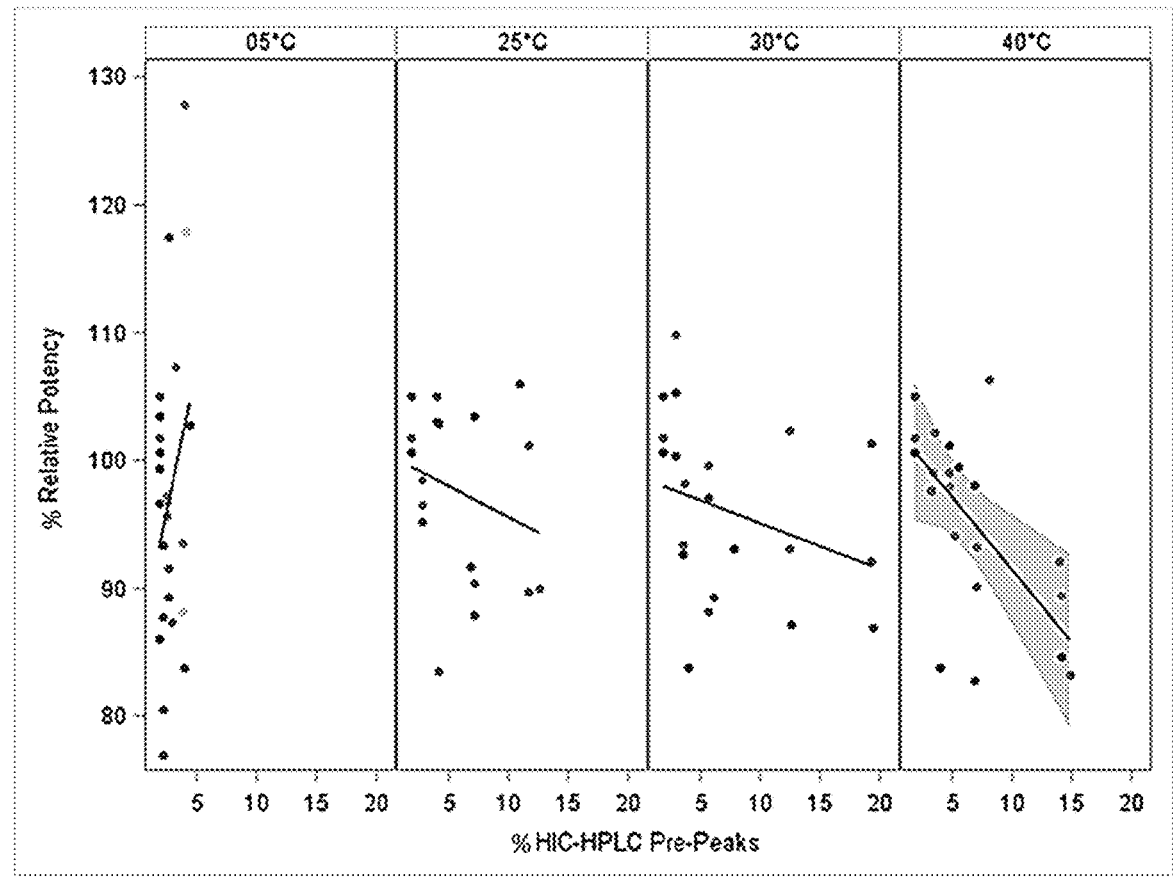
FIG. 9 is a plot of percent relative potency of erenumab lots as a function of percent peak area of pre-peaks in a HIC-HPLC analysis of the same lots for four different storage conditions. Fitted regression lines from a linear regression analysis of the data are shown for each temperature. For the 40° C. condition, the slope of the regression line is statistically different from zero and shows how percent relative potency decreases with an increase in HIC-HPLC pre-peak percent area.

The % relative potency as measured by the cell-based bioassay was plotted as a function of the % peak area for the pre-peaks in the HIC-HPLC chromatogram for the four different storage conditions and a regression analysis was performed (FIG. 9). Slope estimates of the fitted regression lines were determined for each temperature along with the adjusted p-values for the tests to determine whether the slopes differed from zero (Table 12). The slope of the regression line for the data from the 40° C. storage condition was statistically significant from zero at the 0.05 significance level. Based on the regression analysis of the data from the 40° C. storage condition, a 1% increase in HIC-HPLC pre-peak area resulted in a 1.14% decrease in relative potency.

TABLE 12

Linear Regression Parameter Estimates for Relative
Potency vs. HIC-HPLC Pre-Peak Area Percentage

| Temperature | Slope | Standard Error | DF | t Value | Pr > \|t\| | Adj P |
|---|---|---|---|---|---|---|
| 5° C. | 4.3275 | 2.3278 | 45.45 | 1.86 | 0.0695 | 0.2804 |
| 25° C. | −0.4828 | 0.431 | 25.42 | −1.12 | 0.2731 | 1 |
| 30° C. | −0.3574 | 0.2657 | 17.54 | −1.35 | 0.1957 | 0.7436 |
| 40° C. | −1.1373 | 0.3032 | 20.93 | −3.75 | 0.0012 | 0.0022 |

Figure 10:
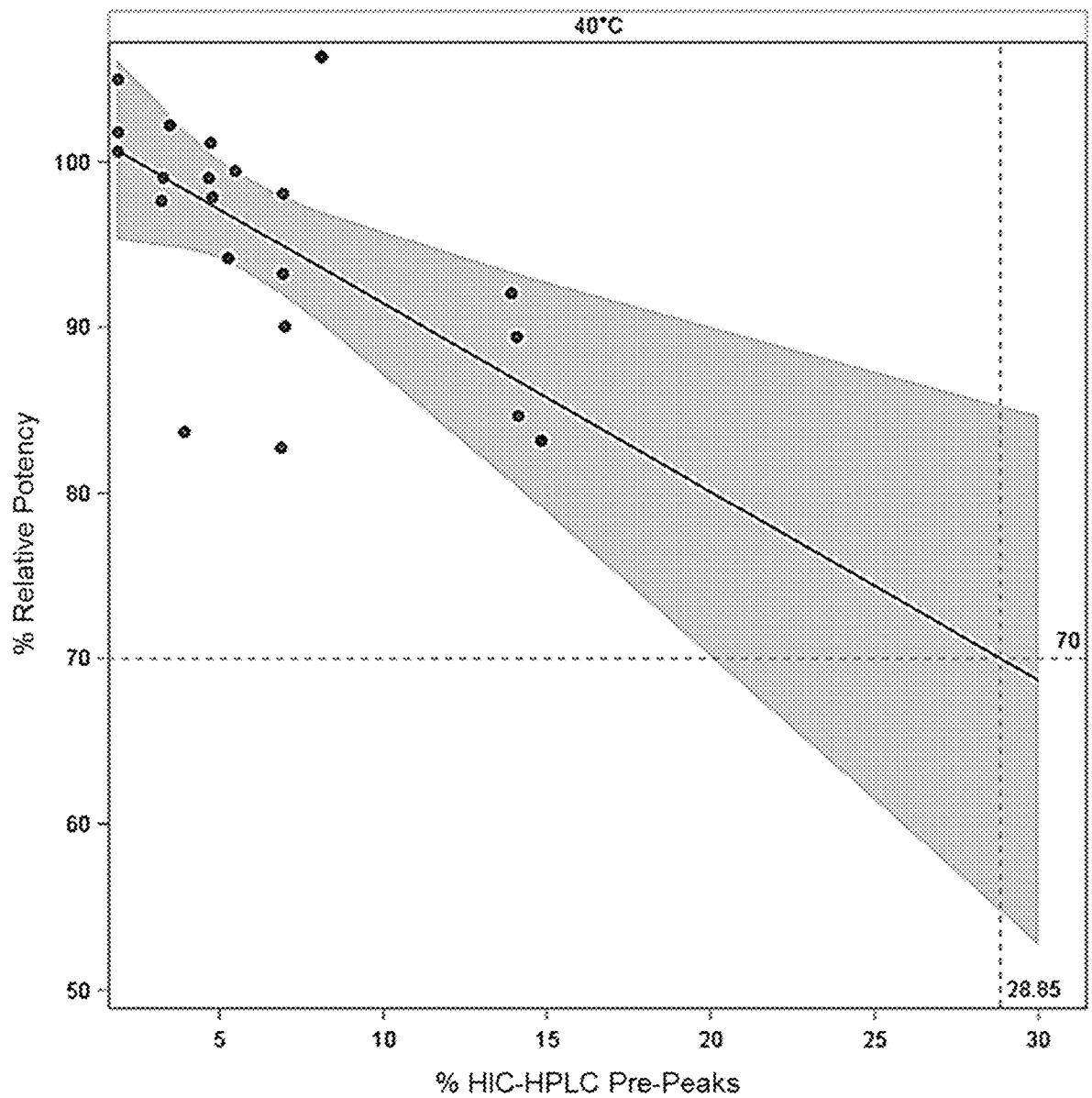
FIG. 10 shows the plot and fitted regression line for the data from the 40° C. storage condition in FIG. 9 with the fitted line extended to cross the 70% relative potency threshold. The 70% relative potency threshold line crosses the regression line around 28.85% HIC-HPLC pre-peak area.

The relative potency of erenumab drug substance employed in clinical trials was greater than 70% as measured by the cell-based bioassay. To estimate the levels of $Asn^{102}$ deamidation and $Asp^{105}$ isomerization variants (represented by the HIC-HPLC pre-peaks) that would reduce the potency of the erenumab drug substance below the level that was acceptable for clinical trials (70%), the fitted regression line for the 40° C. storage condition shown in FIG. 9 was extrapolated to show the % area of HIC-HPLC pre-peaks for a 70% relative potency. As shown in FIG. 10, the predicted value of the % HIC-HPLC pre-peak area for 70% relative potency based on the fitted regression line is about 28.85%.

The results of the experiments described in this example demonstrate that increases in the levels of the $Asn^{102}$ deamidation variant and/or the levels of the $Asp^{105}$ isomerization variant in the erenumab drug substance result in loss of potency of erenumab to inhibit CGRP-induced activation of the CGRP receptor. The levels of the deamidation and isomerization variants should be monitored and controlled to below about 30% in the drug substance to maintain potency of the drug substance to a level similar to the erenumab drug substance employed in clinical trials. In some embodiments, lower levels (e.g. below about 15%) of the $Asn^{102}$ deamidation and/or $Asp^{105}$ isomerization variants in the drug substance are desired as about 17% of these variants in drug substance resulted in a significant reduction in potency of the erenumab drug substance (see Tables 6 and 7).

Example 3. Identification and Characterization of Erenumab Charge Variants by CEX-HPLC This example describes the identification and characterization of additional charge variants of erenumab that exhibited reduced CGRP receptor inhibitory function. Charge heterogeneity of erenumab in this example was evaluated by cation exchange high performance liquid chromatography (CEX-HPLC).

CEX-HPLC separates proteins based primarily on the heterogeneity of surface charge; however, it may also be influenced by structural heterogeneity and other modifications that impact molecular interactions with the ion exchange resin. Peak elution in this method is a function of net surface charge with negatively charged species eluting earlier and positively charged species eluting later.

Samples of erenumab drug substance were loaded onto an analytical CEX-HPLC column (BioPro SP-F, 5 μm particle size, 4.6 mm×100 mm, YMC America, Inc.). Mobile phase A contained 20 mM sodium phosphate at pH 6.6 and mobile phase B consisted of 20 mM sodium phosphate, 500 mM sodium chloride, at pH 6.6. Proteins were separated using a linear salt gradient generated with 5% to 12% mobile phase B from 0 min to 4 min, to 23% mobile phase B at 18 min, to 100% mobile phase B at 18.5 min to 20.5 min, and back to 5% mobile phase B at 21 min to 25 min. The eluent was monitored by UV absorbance at 280 nm. The column was operated at 28° C. and the mobile phase was applied to the column at a flow rate of 0.6 mL/min.

Figure 11:
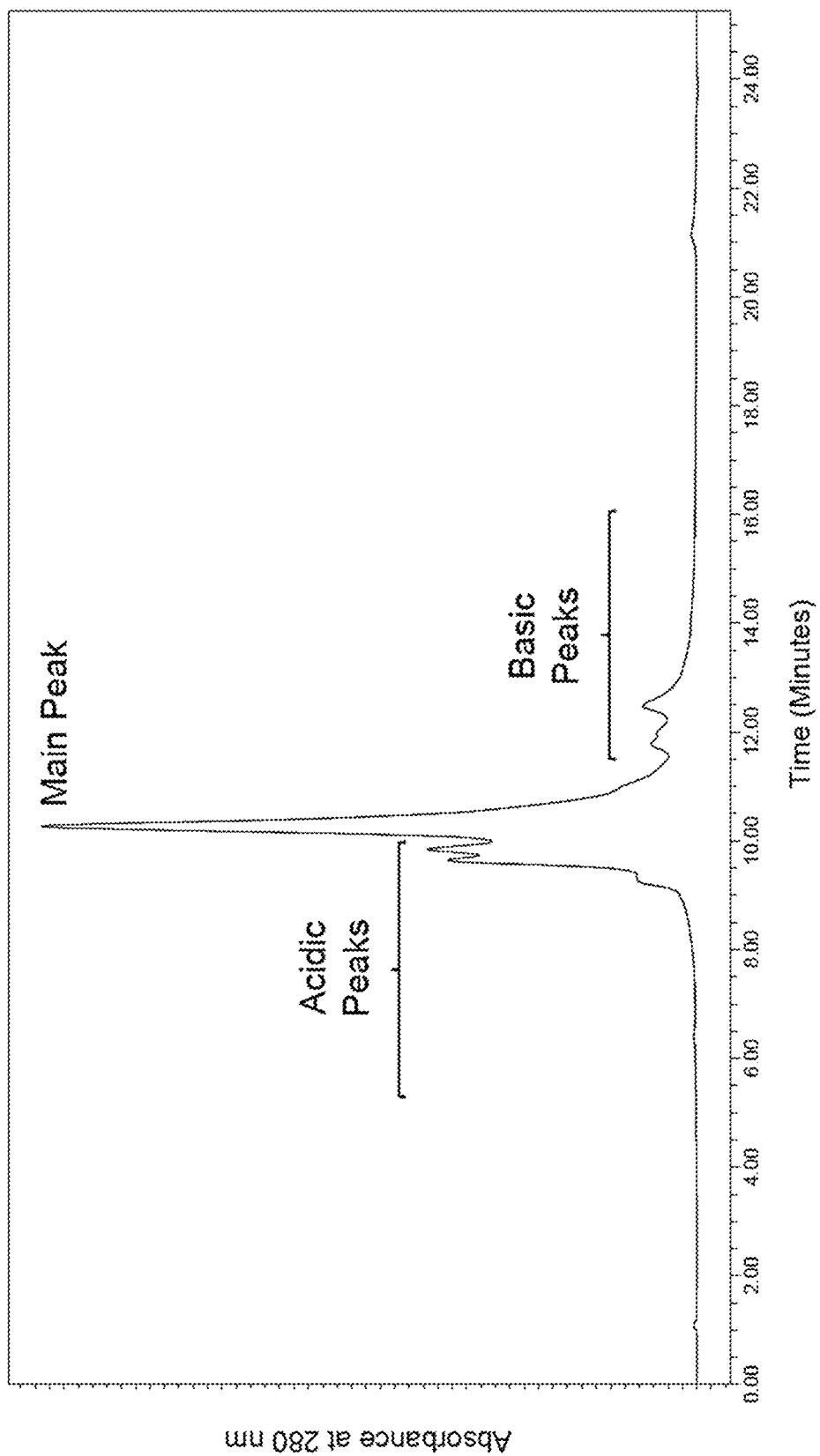
FIG. 11 depicts a representative CEX-HPLC profile of erenumab drug substance. Erenumab drug substance was analyzed by CEX-HPLC using a sodium phosphate pH 6.6 mobile phase with elution by a linear gradient of sodium chloride and detection at 280 nm absorbance.
Figure 12A:
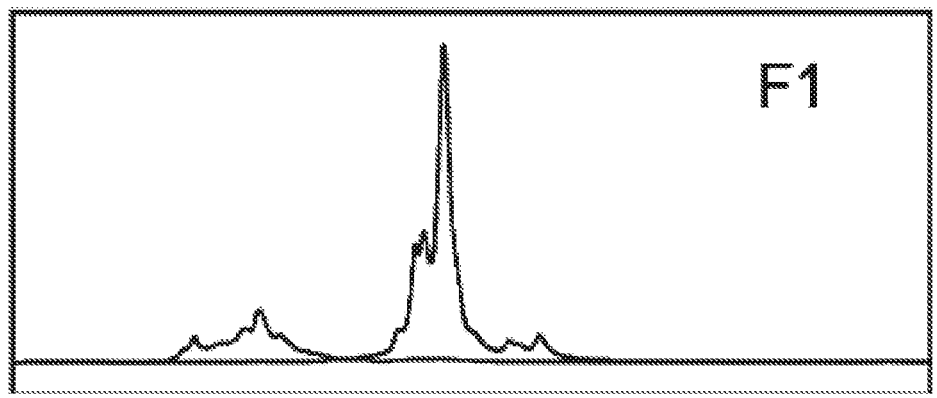
FIGS. 12A-12I show overlays of CEX-HPLC collected fractions and erenumab drug substance analyzed by CEX-HPLC. Erenumab drug substance and fractions collected from semi-preparative CEX-HPLC (F1-F9.
Figure 12B:
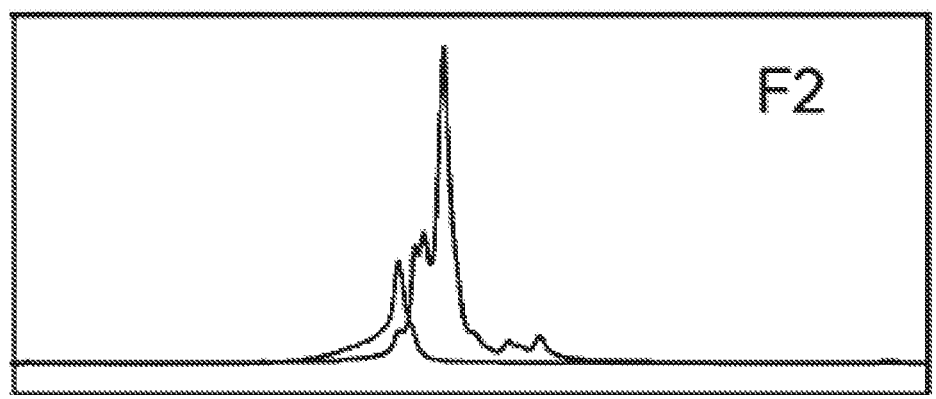
Figure 12C:
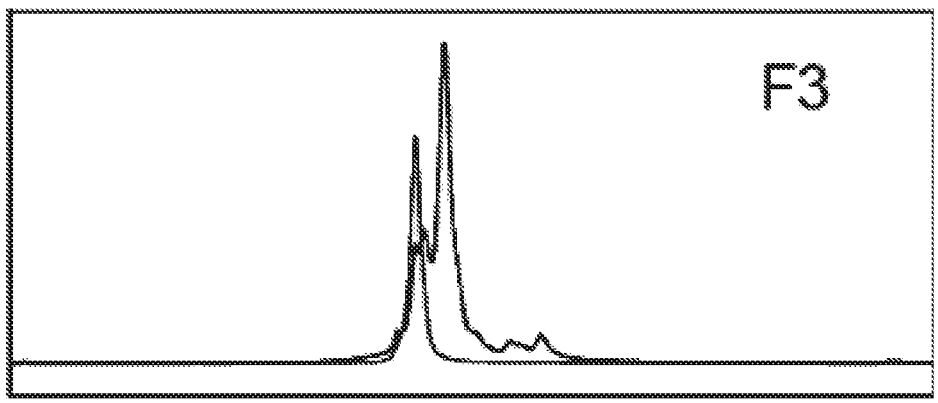
Figure 12D:
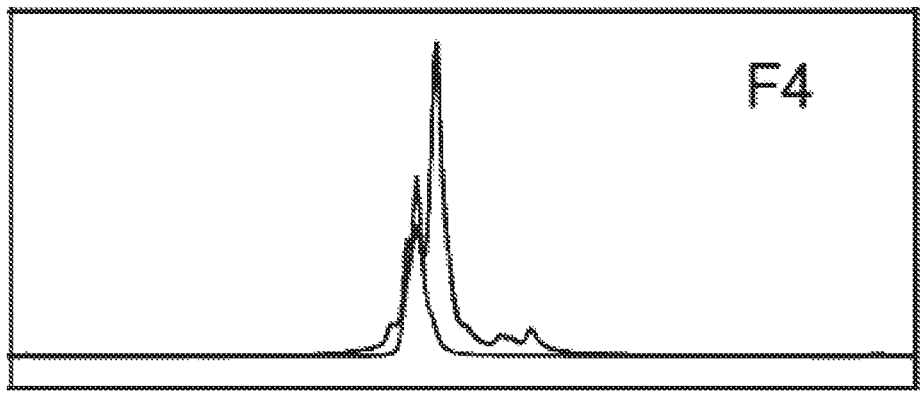
Figure 12E:
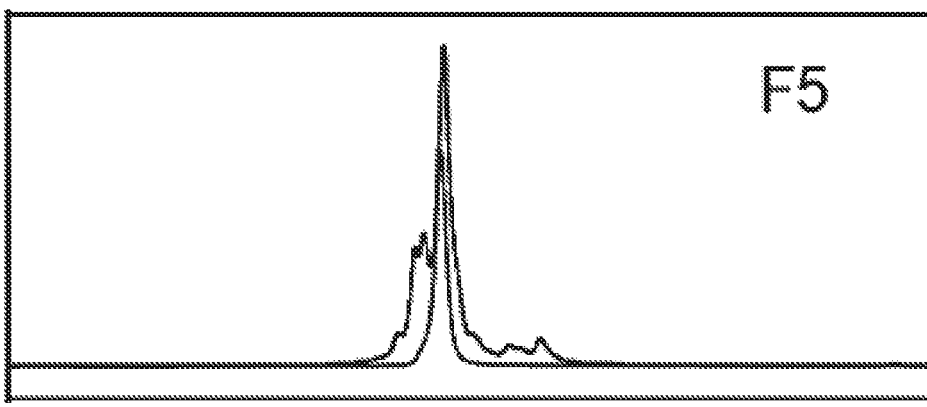
Figure 12F:
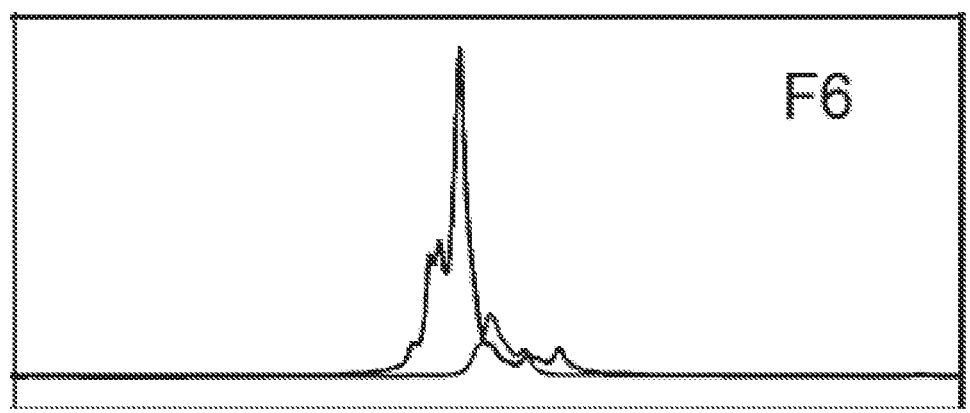
Figure 12G:
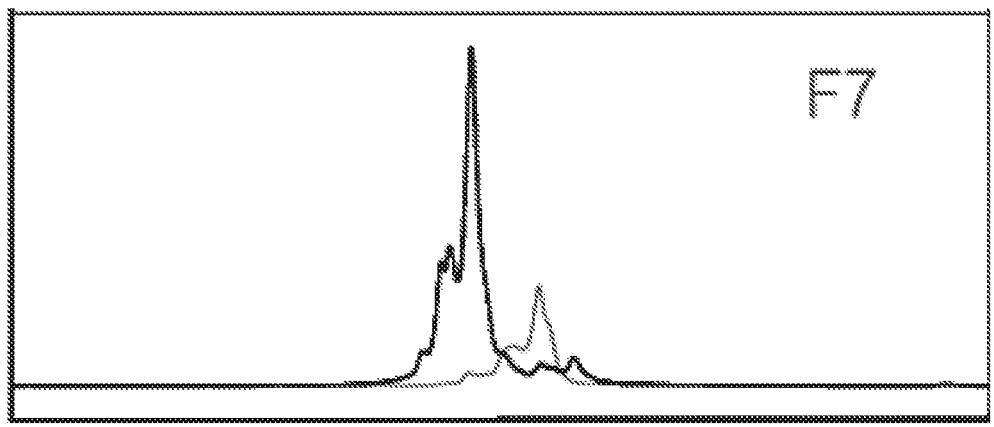
Figure 12H:
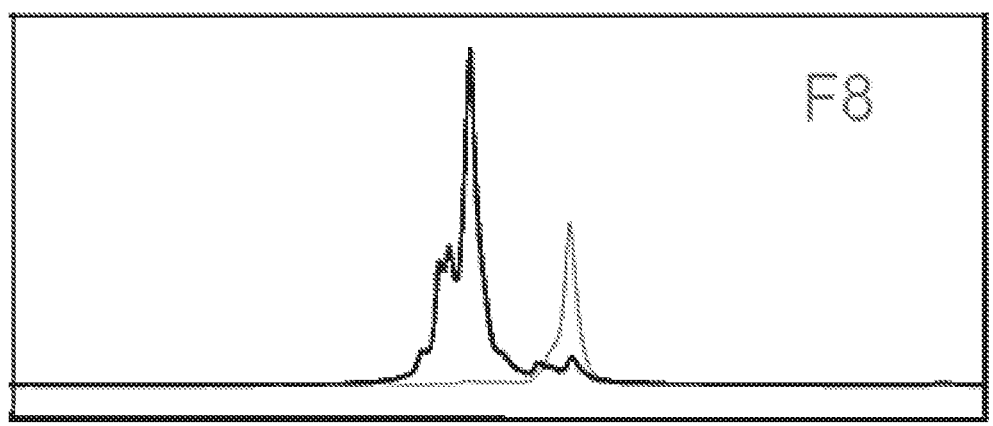
Figure 12I:
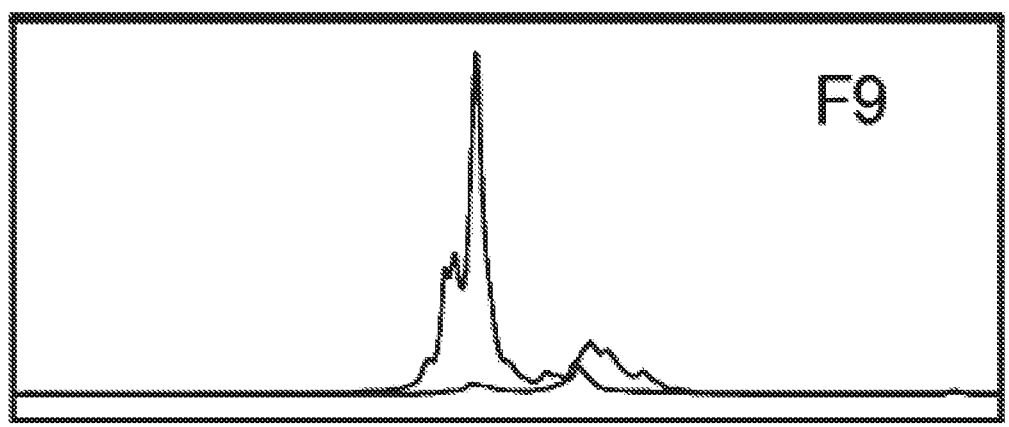

The CEX-HPLC profile contained three distinct regions, including acidic peaks, main peak, and basic peaks (FIG. 11). Nine fractions across the acidic peak, main peak, and basic peak regions were isolated. The collected fractions were re-analyzed by CEX-HPLC to demonstrate that the fractions were of sufficient purity for characterization. CEX-HPLC profiles and purities of the isolated fractions are shown in FIGS. 12A-12I and Table 13, respectively.

TABLE 13

CEX-HPLC Peak Area Percentage of Enriched Fractions[1]

| Sample Description | Acidic Peaks | | | | Main Peak | | Basic Peaks | | |
|---|---|---|---|---|---|---|---|---|---|
| | % F1 | % F2 | % F3 | % F4 | % F5 | % F6 | % F7 | % F8 | % F9 |
| Drug Substance | 0.7 | 6.2 | 10.7 | 13.4 | 52.1 | 5.3 | 4.8 | 4.7 | 2.0 |
| Acidic Fraction F1 | 90.7 | 9.3 | — | — | — | — | — | — | — |
| Acidic Fraction F2 | 3.7 | 80.0 | 16.4 | — | — | — | — | — | — |
| Acidic Fraction F3 | — | 7.5 | 84.0 | 8.6 | — | — | — | — | — |
| Acidic Fraction F4 | — | — | 17.7 | 67.6 | 14.7 | — | — | — | — |
| Main Fraction F5 | — | — | — | 7.3 | 92.7 | — | — | — | — |
| Main Fraction F6 | — | — | — | — | 14.5 | 65.2 | 20.3 | — | — |
| Basic Fraction F7 | — | — | — | — | 11.1 | 27.4 | 57.3 | 4.2 | — |
| Basic Fraction F8 | — | — | — | — | — | 4.6 | 13.0 | 77.8 | 4.6 |
| Basic Fraction F9 | — | — | — | — | 10.2 | 2.6 | 6.4 | 36.6 | 44.1 |

[1]All CEX-HPLC fractions were collected from the same drug substance lot. Fraction of interest based on the collection time window and relative purity emphasized and underlined. Peaks not detected are denoted with a dash.

The biological activity of each of the enriched CEX-HPLC fractions compared to erenumab drug substance was evaluated by the cell-based bioassay described in Example 1. As shown in Table 14, both acidic peak fraction F1 and F2 showed reduced potency relative to the drug substance, whereas the rest of the acidic, main, and basic peak fractions showed no significant differences.

TABLE 14

Potency of Enriched CEX-HPLC Fractions

| Sample Description | % Relative Potency by Cell-Based Bioassay[1] | % CV |
|---|---|---|
| Drug Substance | 91 | 13 |
| Acidic Fraction F1 | 28[2] | 3 |
| Acidic Fraction F2 | 58 | 14 |
| Acidic Fraction F3 | 71 | 20 |
| Acidic Fraction F4 | 82 | 18 |
| Main Fraction F5 | 101 | 16 |
| Main Fraction F6 | 92 | 16 |
| Basic Fraction F7 | 96 | 7 |

TABLE 14-continued

Potency of Enriched CEX-HPLC Fractions

| Sample Description | % Relative Potency by Cell-Based Bioassay[1] | % CV |
|---|---|---|
| Basic Fraction F8 | 102 | 8 |
| Basic Fraction F9 | 98 | 4 |

[1]Average of 3 replicates
[2]One of the 3 replicates failed assay parallelism criterion To more completely understand which variants in the acidic fractions were having an impact on potency, the enriched CEX-HPLC fractions were characterized by various analytical techniques, including non-reduced sodium dodecyl sulfate capillary electrophoresis (nrCE-SDS), reduced sodium dodecyl sulfate capillary electrophoresis (rCE-SDS), and non-reduced reversed phase high performance liquid chromatography (RP-HPLC).

Unfractionated drug substance and the nine CEX-HPLC fractions were analyzed by nrCE-SDS. Samples were denatured by heating in the presence of sodium dodecyl sulfate (SDS) and N-ethylmaleimide at pH 6.5 prior to electrokinetic injection into a bare-fused silica capillary filled with SDS gel buffer at 25° C. Absorbance was monitored at 220 nm. As shown in Table 15 below, the acidic fraction F1 was enriched in both pre-peak and post-peak species relative to the drug substance. The pre-peak species include species that are of a lower molecular weight than intact erenumab (main peak), either resulting from peptide hydrolysis or partial molecule assemblies, whereas the post-peak species are larger in size relative to the main peak. Overall, the relative amounts of pre-peak species were consistent among the rest of the acidic, main and basic peak fractions (i.e. F2 through F9) and the drug substance, though small differences in the distribution within the pre-peak group were observed.

TABLE 15 nrCE-SDS Peak Area Percentage of Enriched CEX-HPLC Fractions

| Sample Description | % Pre-peaks | % Main Peak | % Post-peaks |
|---|---|---|---|
| Drug Substance | 2.9 | 97.1 | 0.0 |
| Acidic Fraction F1 | 78.3 | 20.3 | 1.4 |
| Acidic Fraction F2 | 3.5 | 96.5 | 0.0 |
| Acidic Fraction F3 | 3.7 | 96.3 | 0.0 |
| Acidic Fraction F4 | 3.4 | 96.6 | 0.0 |
| Main Fraction F5 | 1.4 | 98.6 | 0.0 |
| Main Fraction F6 | 4.1 | 95.9 | 0.0 |
| Basic Fraction F7 | 3.3 | 96.7 | 0.0 |
| Basic Fraction F8 | 1.7 | 98.3 | 0.0 |
| Basic Fraction F9 | 2.6 | 96.7 | 0.7 |

The erenumab drug substance and nine CEX-HPLC fractions were also analyzed by rCE-SDS. The method for rCE-SDS was similar to that for nrCE-SDS except that the samples were reduced and denatured by heating in the presence of SDS and β-mercaptoethanol prior to injection into the capillary. The results of the rCE-SDS analysis showed that all fractions with the exception of acidic peak fraction F1 were similar to the unfractionated drug substance control. Acidic peak fraction F1 was significantly enriched in LMW and MMW species corresponding most likely to peptide hydrolysis fragments (data not shown). The acidic peak fraction F1, and to a lesser amount fraction F2, were enriched for post heavy chain corresponding to non-consensus glycosylation variants.

Figure 13A:
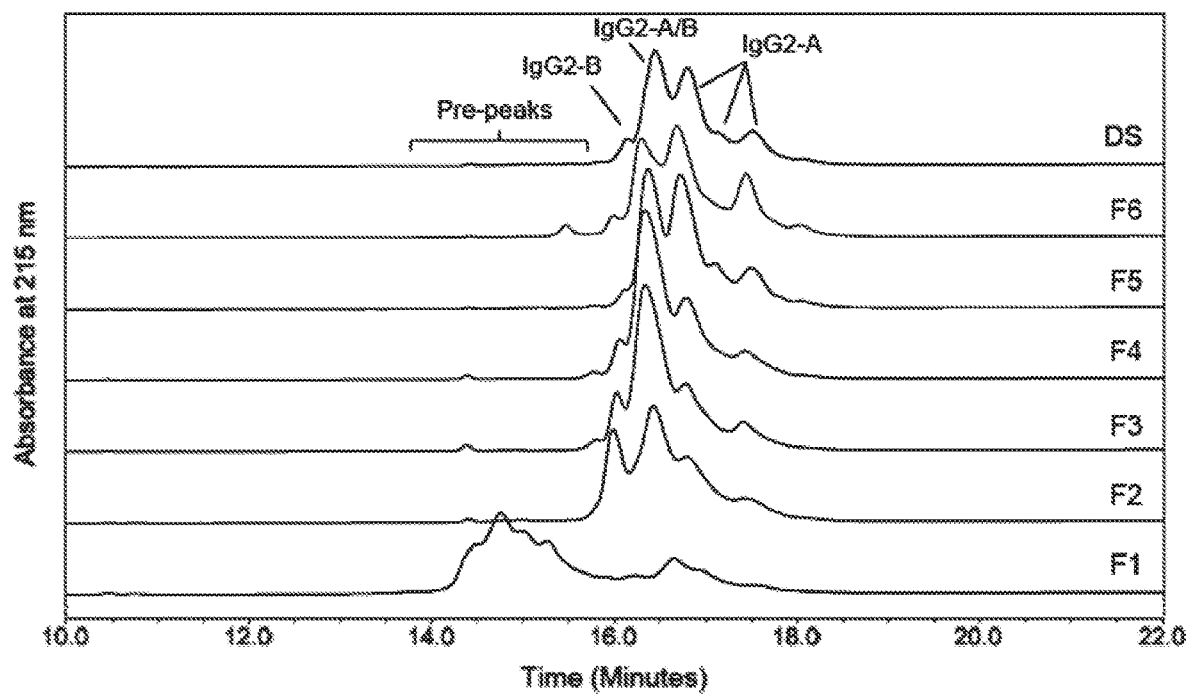
FIGS. 13A and 13B show RP-HPLC profiles of CEX-HPLC acidic and main peak fractions (FIG. 13A) and CEX-HPLC basic peak fractions (FIG. 13B). Erenumab drug substance (DS) and CEX-HPLC fractions (F1-F9) were analyzed by RP-HPLC using a Waters BEH300 C4 column (1.7 μm particle size, 2.1 mm×50 mm) and eluted using a 0.1% TFA-containing mobile phase and a gradient of 1-propanol at 75° C. with detection at 215 nm. IgG2-A, IgG2-AB, and IgG2-B correspond to different disulfide isoforms of erenumab. The structures of the different disulfide isoforms are schematically shown in FIGS. 15A-15C.
Figure 13B:
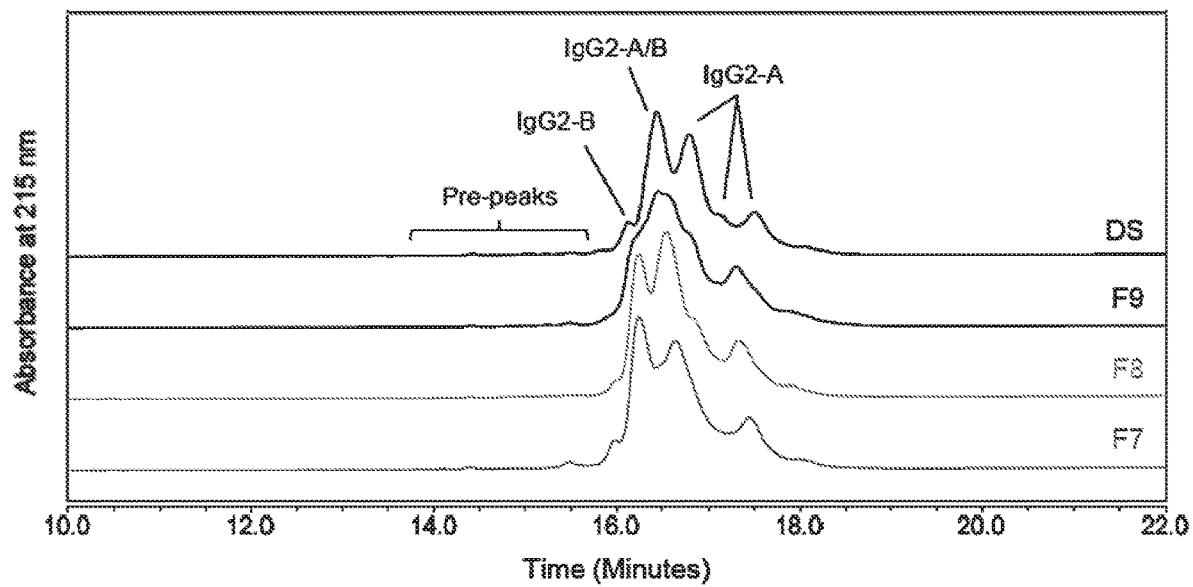

Next, the drug substance and CEX-HPLC fractions were analyzed by RP-HPLC using a Waters BEH300 C4 column (1.7 μm particle size, 2.1 mm×50 mm) and eluted using a 0.1% TFA-containing mobile phase and a gradient of 1-propanol at 75° C. Absorbance at 215 nm was monitored. Across the CEX-HPLC profile, there was an observed trend of disulfide isoform enrichment with IgG2-B and IgG2-AB isoforms enriched in acidic fractions, whereas IgG2-A disulfide isoforms are enriched in the main and basic peak fractions (FIGS. 13A and 13B and Table 16). As described in more detail in Example 4, the IgG2-B disulfide isoform was significantly less potent than the erenumab drug substance or the IgG2-A and IgG2-AB disulfide isoforms. The RP-HPLC profile of acidic peak fraction F1 was not consistent with the drug substance chromatogram, which most likely was a result of the significant levels of reducible and covalent fragmentation observed by rCE-SDS and nrCE-SDS, respectively, as described above.

TABLE 16

RP-HPLC Peak Area Percentage of Enriched CEX-HPLC Fractions

| Sample Description | % Pre-peaks | % IgG2-B | % IgG2-A/B | % IgG2-A |
|---|---|---|---|---|
| Drug Substance | 1.5 | 5.9 | 36.6 | 56.0 |
| Acidic Fraction F1 | 69.1 | 8.1 | 11.3 | 11.5 |
| Acidic Fraction F2 | 2.3 | 21.4 | 40.4 | 35.8 |
| Acidic Fraction F3 | 1.2 | 11.2 | 55.1 | 32.4 |
| Acidic Fraction F4 | 1.1 | 7.0 | 52.5 | 39.4 |
| Main Fraction F5 | 0.8 | 2.9 | 33.9 | 62.4 |
| Main Fraction F6 | 2.8 | 3.9 | 27.8 | 65.5 |
| Basic Fraction F7 | 2.1 | 3.9 | 28.6 | 65.4 |
| Basic Fraction F8 | 1.4 | 2.0 | 23.3 | 73.3 |
| Basic Fraction F9 | 1.8 | 11.0 | 31.3 | 55.9 |

The results of the analyses described in this example show that certain acidic variants of erenumab, such as fragmentation variants and disulfide isoform variants, corresponding to the acidic peaks in the CEX-HPLC chromatogram are less potent than erenumab drug substance. Specifically, acidic fraction F1 showed a significant decrease in potency as a result of the high levels of fragmentation detected by rCE-SDS and nrCE-SDS. Acidic fraction F2 also showed a decrease in potency due to the elevated levels of the IgG2-B disulfide isoform enriched in this fraction relative to the non-fractionated drug substance. Overall, the primary erenumab variants detected by CEX-HPLC include disulfide isoform variants, with IgG2-B and IgG2-AB isoforms enriched in the acidic peaks. Deamidation, fragmentation (LMW and MMW), HMW species and non-consensus glycosylation variants were also detected in the acidic peak fractions.

Several lots of erenumab drug substance (140 mg/mL) manufactured at commercial scale were analyzed by CEX-HPLC to assess the presence and quantity of acidic variants (e.g. IgG2-B disulfide isoform) as measured by the peak area percentage of the acidic peaks in the CEX-HPLC chromatogram. Potency of the drug substance lots was also evaluated by the cell-based potency assay and compared to the potency of Lot No. 78137, which is representative of the erenumab drug substance employed in Phase II/Phase III clinical trials. A summary of the data is provided in Table 17 below.

TABLE 17

CEX-HPLC and Potency Data for Erenumab Drug Substance Lots

| | CEX-HPLC | | | Cell-Based Bioassay |
|---|---|---|---|---|
| Lot Number | % Main Peak | % Acidic Peaks | % Basic Peaks | % Relative Potency |
| 78137 (clinical trial material) | — | — | — | 101 |
| 63130 | 57.8 | 31.3 | 10.9 | 98 |
| 63131 | 58.6 | 29.7 | 11.7 | 124 |
| 63132 | 58.2 | 28.7 | 13.1 | 92 |
| 63133 | 58.1 | 30.1 | 11.8 | 96 |
| 63134 | 57.6 | 30.5 | 11.9 | 101 |

As shown by the data in Table 17, erenumab drug substance manufactured at commercial scale contained a consistent level of acidic variants ranging from 28.7% to 31.3% as measured by CEX-HPLC acidic peaks. Drug substance that contained levels of acidic variants in this range exhibited a potency that was comparable to the potency of the erenumab drug substance employed in clinical trials.

Example 4. Disulfide Isoform Variants of Erenumab

Erenumab is an antibody of the IgG2 subclass and therefore may exhibit the disulfide isoform variants that have been described for IgG2 molecules (Dillon et al., J Chromatogr A., Vol. 1120(1-2):112-120, 2006; Wypych et al., Journal of Biological Chemistry, Vol. 283(23):16194-16205, 2008; Dillon et al., Journal of Biological Chemistry, Vol. 283(23):16206-16215, 2008). The connectivity of disulfide bonds detected in erenumab was elucidated using non-reduced and reduced Lys-C peptide maps coupled with electrospray ionization tandem mass spectrometry (ESI-MS/MS) for identification. Through this approach, the expected disulfide bonds of the classical IgG2-A structure were elucidated, as well as disulfide bonds corresponding to the IgG2-AB and IgG2-B structures.

Figure 14:
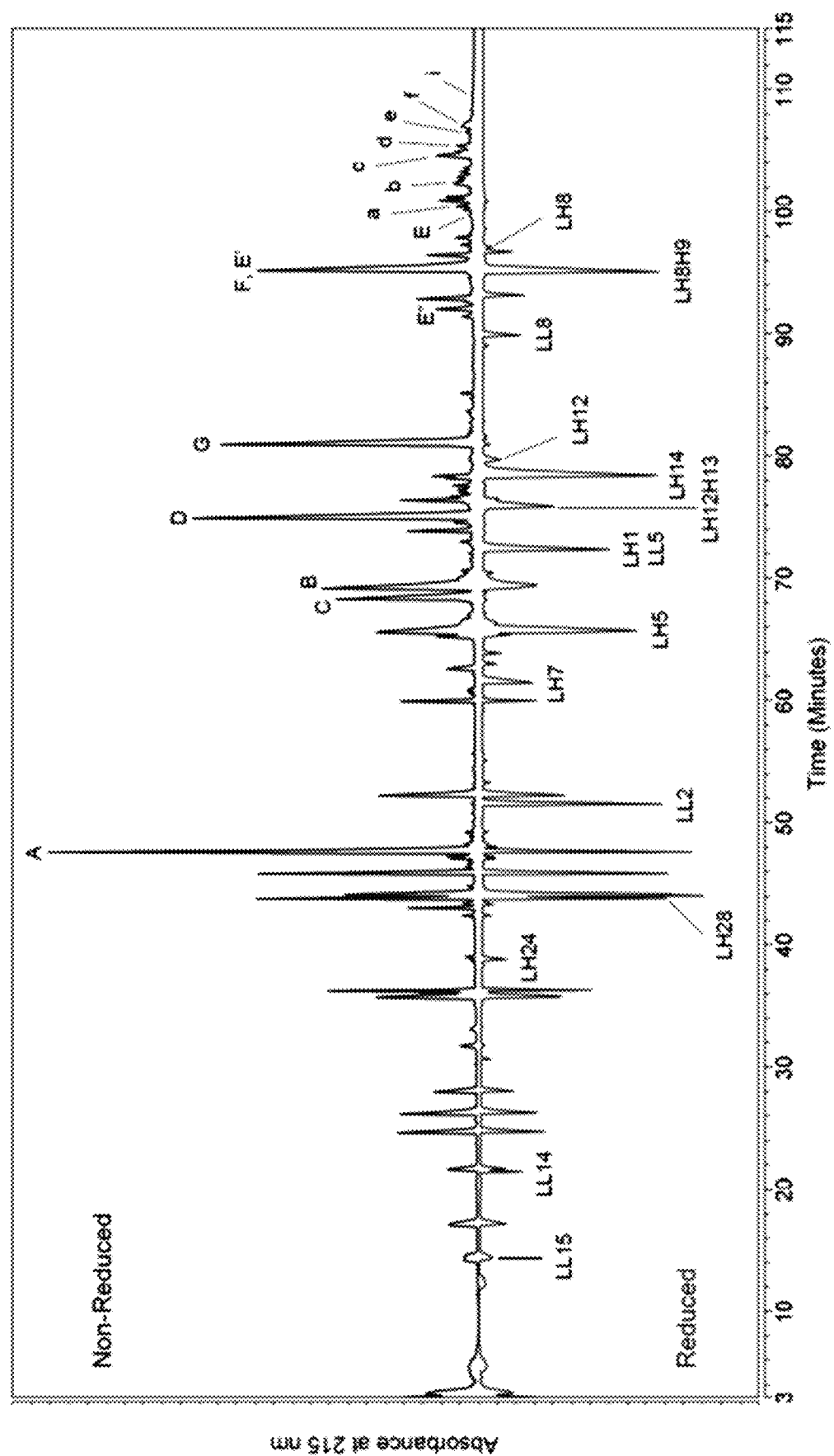
FIG. 14 illustrates the Lys-C peptide maps of non-reduced (top trace) and reduced (bottom trace) erenumab. Erenumab drug substance was denatured and digested with endoprotease Lys-C. Labeled peaks in the reduced map identify peptides present in the reduced Lys-C peptide map but absent in non-reduced Lys-C peptide map. Description for each of the labeled peptides is listed in Tables 18 and 19.

Disulfide-linked peptides were identified in drug substance by peptide mapping using endoprotease Lys-C under non-reducing and reducing conditions as shown in FIG. 14. The outlet of the reversed-phase high performance liquid chromatography (RP-HPLC) separation was coupled to an electrospray ionization tandem mass spectrometer (ESI-MS/MS) for orthogonal mass analysis in addition to absorbance detection. A portion of the non-reduced digest was treated with the reducing agent tris(2-carboxyethyl) phosphine hydrochloride (TCEP), and analyzed using the same RP-HPLC conditions.

Figure 15B:
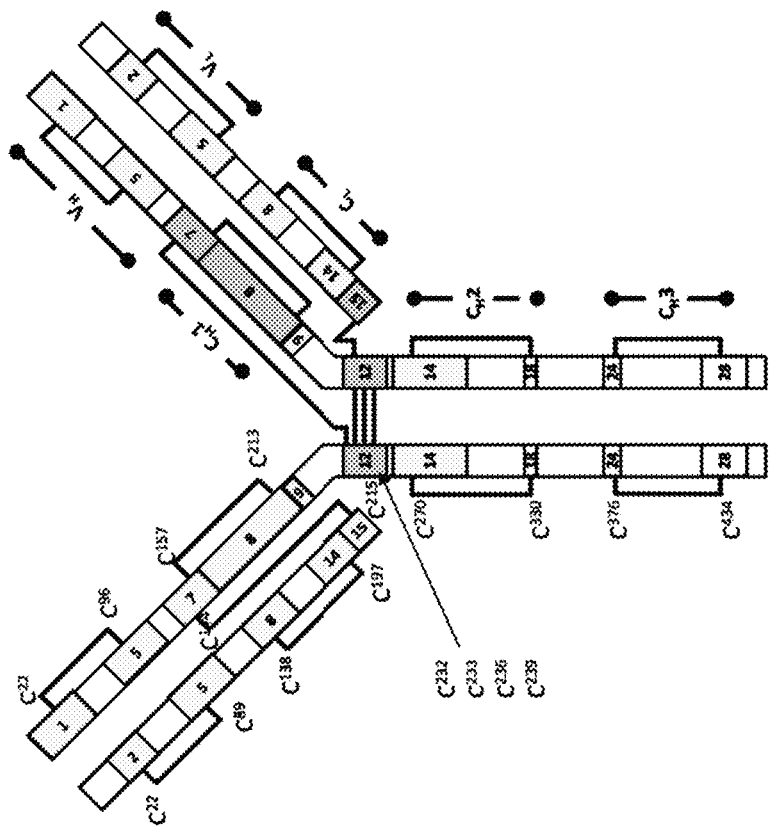
FIG. 15B is a schematic of erenumab disulfide isoform IgG2-AB structure identified by non-reduced and reduced Lys-C peptide map.
Figure 15A:
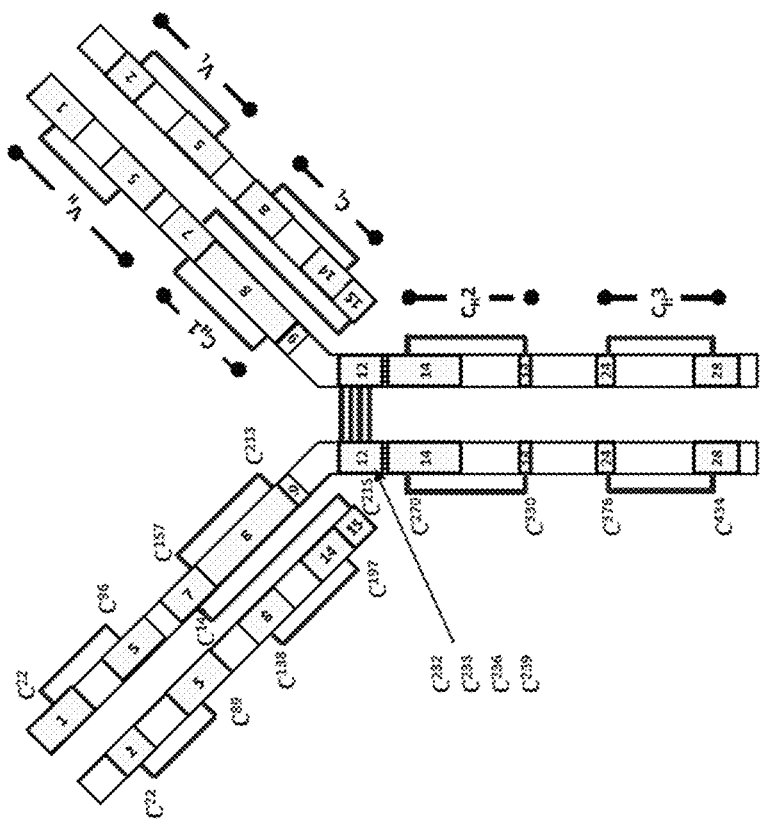
FIG. 15A is a schematic of erenumab disulfide isoform IgG2-A structure identified by non-reduced and reduced Lys-C peptide map.

The non-reduced Lys-C map (FIG. 14, top trace) is labeled with peaks "A" through "G" and "a" through "i," which disappear under reducing conditions. Disappearance of these peptides after reduction indicates that they are involved in disulfide linkages in the native protein. Peptides that contain disulfide bonds in the non-reduced Lys-C digest and the corresponding reduced peptides in the reduced Lys-C digest were determined by their presence or absence in the absorbance chromatograms and confirmed by intact peptide mass accuracy and the presence of diagnostic MS/MS product ions. The theoretical and observed masses for all of the peptide ions used to verify disulfide-linked peptides are shown in Table 18 and Table 19 for the non-reduced and reduced peptide maps, respectively. The identified non-reduced and reduced peptides account for the expected IgG2-A disulfide isoform structure, which is schematically shown in FIG. 15A.

TABLE 18

Peptides Containing IgG2 Disulfide Linkages Identified in the Non-reduced Lys-C Peptide Map of Erenumab

| Peak ID | Disulfide Bonded Peptide | Cys-Cys Connection | Element | Theoretical Mass$^a$ (Da) | Observed Mass$^a$ (Da) | Mass Accuracy (ppm) |
|---|---|---|---|---|---|---|
| A | LH24/LH28 | $C^{376}(H)$-$C^{434}(H)$ | $C_H3$ | 4087.9567 | 4087.9621 | 1.3 |
| B | LL8/LL14 | $C^{138}(L)$-$C^{197}(L)$ | $C_L$ | 4185.0300 | 4185.0394 | 2.3 |
| C | LH14/LH18 | $C^{270}(H)$-$C^{330}(H)$ | $C_H2$ | 4803.2619 | 4803.2853 | 4.9 |
| D | LL2/LL5 | $C^{22}(L)$-$C^{89}(L)$ | $V_L$ | 7026.2876 | 7026.3205 | 4.7 |
| E | LH12/LH12 | $C^{232}(H)$-$C^{232}(H^{\wedge})$ | Hinge of IgG2-A | 4900.2590 | 4900.2585 | 0.1 |
| E' | LH12/LH12LH13 | $C^{233}(H)$-$C^{233}(H^{\wedge})$ | Hinge of IgG2-A | 5125.4068 | 5125.4065 | 0.1 |
| E" | LH12LH13/LH12LH13 | $C^{236}(H)$-$C^{236}(H^{\wedge})$ $C^{239}(H)$-$C^{239}(H^{\wedge})$ | Hinge of IgG2-A | 5350.5545 | 5350.5741 | 3.7 |
| F | LH7/LH8LH9/LL15 | $C^{144}(H)$-$C^{215}(L)$ $C^{157}(4)$-$C^{213}(H)$ | Inter HC-LC and $C_H1$ | 10084.8384 | 10084.8556 | 1.7 |
| G | LH1/LH5 (pE) | $C^{22}(H)$-$C^{96}(H)$ | $V_H$ | 9002.3068 | 9002.3306 | 2.6 |
| a | LH7/LH8LH9/LH12LH13/LL15 | $C^{144}(H)$-$C^{233}(H^{\wedge})$ $C^{157}(H)$-$C^{213}(H)$ | IgG2-B | 12768.3$^b$ | 12768.2$^b$ | 13.0 |
| b | H7/H8H9/H11H12H13/H12H13/L15 | $C^{232}(H^{\wedge})$-$C^{215}(L^{\wedge})$ $C^{236}(H^{\wedge})$-$C^{239}(H^{\wedge})$ | IgG2-B | 16061.3$^b$ | 16060.8$^b$ | 28.1 |
| c | LH7/LH8LH9/(LH12LH13)$_2$/LL15 | $C^{144}(H)$-$C^{232}(H^{\wedge})$ $C^{157}(H)$-$C^{213}(H)$ | IgG2-A/B | 15445.6$^b$ | 15445.5$^b$ | 6.8 |
| f | LH7/LH8H9/LH12/LH12LH13/LL15 | $C^{232}(H)$-$C^{215}(L)$ $C^{233}(H)$-$C^{233}(H^{\wedge})$ | IgG2-A/B | 15220.3$^b$ | 15220.3$^b$ | 1.9 |
| i | LH7/LH8H9/(LH12)$_2$/LL15 | $C^{236}(H)$-$C^{236}(H^{\wedge})$ $C^{239}(H)$-$C^{239}(H^{\wedge})$ | IgG2-A/B | 14995.0$^b$ | 14995.1$^b$ | 10.2 |
| d | (LH7)$_2$/(LH8H9)$_2$/(LH11H12H13)$_2$/(LL15)$_2$ | $C^{144}(H)$-$C^{233}(H^{\wedge})$ $C^{157}(H)$-$C^{213}(H)$ $C^{232}(H)$-$C^{215}(L)$ $C^{236}(H)$-$C^{236}(H^{\wedge})$ | IgG2-B | 267641$^b$ | 26 764 .4$^b$ | 11.5 |

TABLE 18-continued

Peptides Containing IgG2 Disulfide Linkages Identified in the Non-reduced Lys-C Peptide Map of Erenumab

| Peak ID | Disulfide Bonded Peptide | Cys-Cys Connection | Element | Theoretical Mass$^a$ (Da) | Observed Mass$^a$ (Da) | Mass Accuracy (ppm) |
|---|---|---|---|---|---|---|
| e | (LH7)$_2$/(LH8H9)$_2$/ LH11H12H13/ LH12H13/(LL15)$_2$ | $C^{239}$(H)-$C^{239}$(H^) $C^{157}$(H^)-$C^{213}$(H^) $C^{144}$(H^)-$C^{233}$(H) $C^{232}$(H^)-$C^{215}$(L^) | IgG2-B | 26150.4$^b$ | 26150.9$^b$ | 18.7 |

$^a$Masses are monoisotopic unless otherwise noted.
$^b$Average Mass
H = heavy chain;
L = light chain;
^ = other heavy or light chain;
/ = single disulfide bond;
LL = Lys-C digested light chain peptide;
LH = Lys-C digested heavy chain peptide;
pE = pyroglutamate for N-terminal Gln residue on LH1;
Cys residue numbering relative to SEQ ID NO: 1 for heavy chain and SEQ ID NO: 2 for light chain

TABLE 19

Peptides Containing Cysteines Identified in the Reduced Lys-C Peptide Map of Erenumab

| Lys-C Peptide | Amino Acid Residues$^a$ | Cysteine Position$^a$ | Theoretical Mass$^b$ (Da) | Observed Mass$^b$ (Da) | Mass Accuracy (ppm) |
|---|---|---|---|---|---|
| LH1 | pE$^1$-K$^{43}$ | C$^{22}$ | 4501.2536 | 4501.2679 | 3.2 |
| LH5 | N$^{77}$-K$^{113}$ | C$^{96}$ | 4503.0689 | 4503.0763 | 1.6 |
| LH7 | G$^{135}$-K$^{160}$ | C$^{144}$, C$^{157}$ | 2577.2931 | 2577.2976 | 1.8 |
| LH8 | D$^{161}$-K$^{218}$ | C$^{213}$ | 6177.9582 | 6177.9606 | 0.4 |
| LH8H9 | D$^{161}$-K$^{223}$ | | 6705.2286 | 6705.2571 | 4.3 |
| LH12 | C$^{232}$-K$^{255}$ | C$^{232}$, C$^{233}$, C$^{236}$, C$^{239}$ | 2454.1608 | 2454.1696 | 3.6 |
| LH12H13 | C$^{232}$-K$^{257}$ | | 2679.3086 | 2679.3132 | 1.8 |
| LH14 | D$^{258}$-K$^{297}$ | C$^{270}$ | 4556.1628 | 4556.1625 | 0.1 |
| LH18 | C$^{330}$-K$^{331}$ | C$^{330}$ | 249.1147 | ND | — |
| LH24 | N$^{370}$-K$^{379}$ | C$^{376}$ | 1103.6009 | 1103.6013 | 0.4 |
| LH28 | S$^{424}$-K$^{448}$ | C$^{434}$ | 2986.3715 | 2986.3764 | 1.7 |
| LL2 | V$^{18}$-K$^{46}$ | C$^{22}$ | 3057.4502 | 3057.4568 | 2.2 |
| LL5 | S$^{68}$-K$^{106}$ | C$^{89}$ | 3970.8531 | 3970.8529 | 0.0 |
| LL8 | A$^{134}$-K$^{153}$ | C$^{138}$ | 2153.1231 | 2153.1324 | 4.3 |
| LL14 | S$^{191}$-K$^{208}$ | C$^{197}$ | 2033.9225 | 2033.9266 | 2.0 |
| LL15 | T$^{209}$-S$^{216}$ | C$^{215}$ | 806.3480 | 806.3484 | 0.5 |

$^a$Amino acid residue numbering relative to SEQ ID NO: 1 for heavy chain peptides and SEQ ID NO: 2 for light chain peptides
$^b$Masses are monoisotopic
— Not applicable;
LL = Lys-C digested light chain peptide;
LH = Lys-C digested heavy chain peptide;
ND = not detected;
pE = pyroglutamate for N-terminal Gln residue on LH1

Figure 15C:
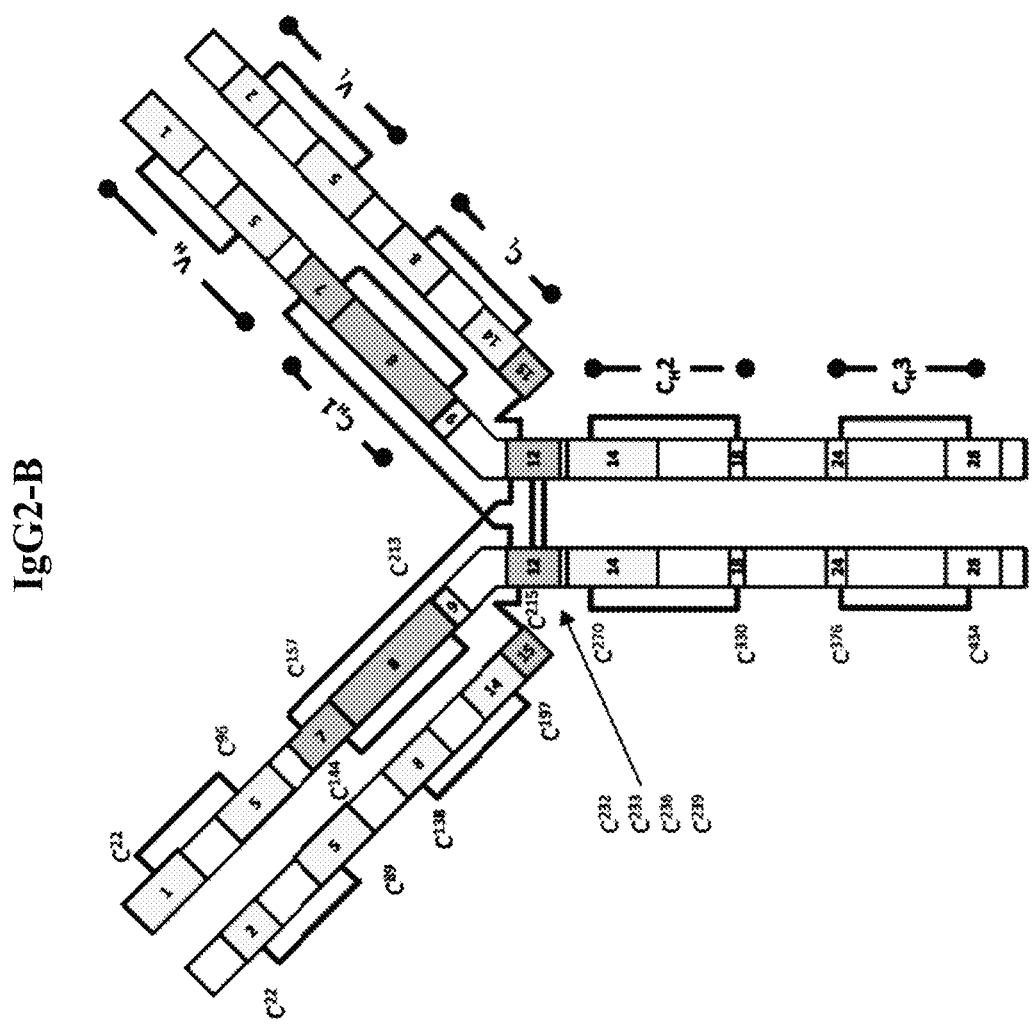
FIG. 15C is a schematic of erenumab disulfide isoform IgG2-B structure identified by non-reduced and reduced Lys-C peptide map.

Lys-C peptide mapping revealed minor disulfide-linked peptide peaks corresponding to heterogeneity of the disulfide pairings between hinge peptides and other regions of the molecule. In addition to the major disulfide-linked peptide peaks labeled in FIG. 14, there are minor late-eluting peaks ("a" through "i") in the non-reduced map that are absent in the reduced map, indicating that they are involved in disulfide linkages in the native protein. These late eluting peptides were identified by mass spectrometry as interchain disulfide bonded peptides for the known structural isoforms of IgG2 (Wypych et al., Journal of Biological Chemistry, Vol. 283(23):16194-16205, 2008; Dillon et al., Journal of Biological Chemistry, Vol. 283(23):16206-16215, 2008; and Zhang et al., Anal Chem., Vol. 82(3):1090-1099, 2010). Peptides "a," "b," "d," and "e" correspond to structural isoform IgG2-B, whereas peptides "c," "f," and "i" correspond to structural isoform IgG2-AB. Schematic representations of the IgG2-AB and IgG2-B disulfide isoform structures are depicted in FIGS. 15B and 15C, respectively. The theoretical and observed masses for all of the peptide ions used to verify the IgG2-AB and IgG2-B disulfide-linked peptides are shown in Table 18. The analyses suggest that the disulfide linkages of erenumab are consistent with those observed previously for IgG2 antibodies (Wypych et al., 2008; Dillon et al., 2008; and Zhang et al., 2010).

Figure 16A:
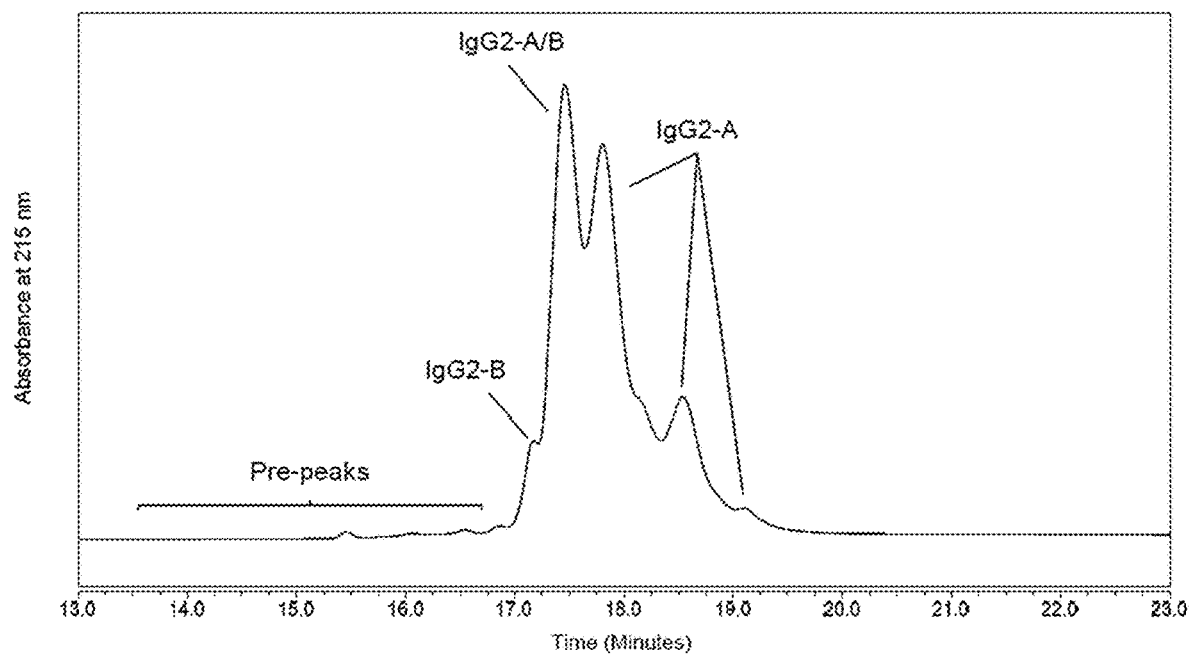
FIG. 16A is a non-reduced RP-HPLC profile of erenumab drug substance at expanded scale. Erenumab drug substance was analyzed by RP-HPLC using a Waters BEH300 C4 column (1.7 μm particle size, 2.1 mm×50 mm) and eluted using a 0.1% TFA-containing mobile phase and a gradient of 1-propanol at 75° C. with detection at 215 nm. IgG2-A, IgG2-AB, and IgG2-B correspond to different disulfide isoforms of erenumab. The structures of the different disulfide isoforms are schematically shown in FIGS. 15A-15C.

As detailed above, peptide mapping revealed the presence of disulfide-linked peptides for the predominant IgG2-A structure, as well as peptides bearing connectivity associated with the additional IgG2-AB and IgG2-B disulfide structural isoforms. As shown in FIG. 15, in IgG2-B isoforms, both Fab arms are linked to the hinge region whereas in IgG2-A isoforms, neither Fab arm is linked to the hinge. The IgG2-AB isoform is a hybrid between these two forms, with only one Fab arm disulfide-linked to the hinge. Separation of IgG2 disulfide isoforms by non-reduced reversed phase high performance liquid chromatography (RP-HPLC) has been previously reported (Wypych et al., 2008 and Dillon et al., 2008). In these studies, peptides corresponding to disulfide isoforms A, AB and B were identified in RP-HPLC peak fractions (Wypych et al., 2008 and Dillon et al., 2008). A representative profile for erenumab drug substance analyzed by non-reduced RP-HPLC is shown in FIG. 16A with disulfide isoform peaks labeled consistent with the elution order reported by Wypych et al., 2008. Late-eluting peaks are identified as IgG2-A isoforms and grouped with the IgG2-A peak for reporting of relative percent. The relative level of disulfide isoforms in erenumab drug substance is approximately 59.5% IgG2-A, 34.7% IgG2-AB, and 4.4% IgG2-B with approximately 1.5% early-eluting pre-peak species.

Figure 16B:
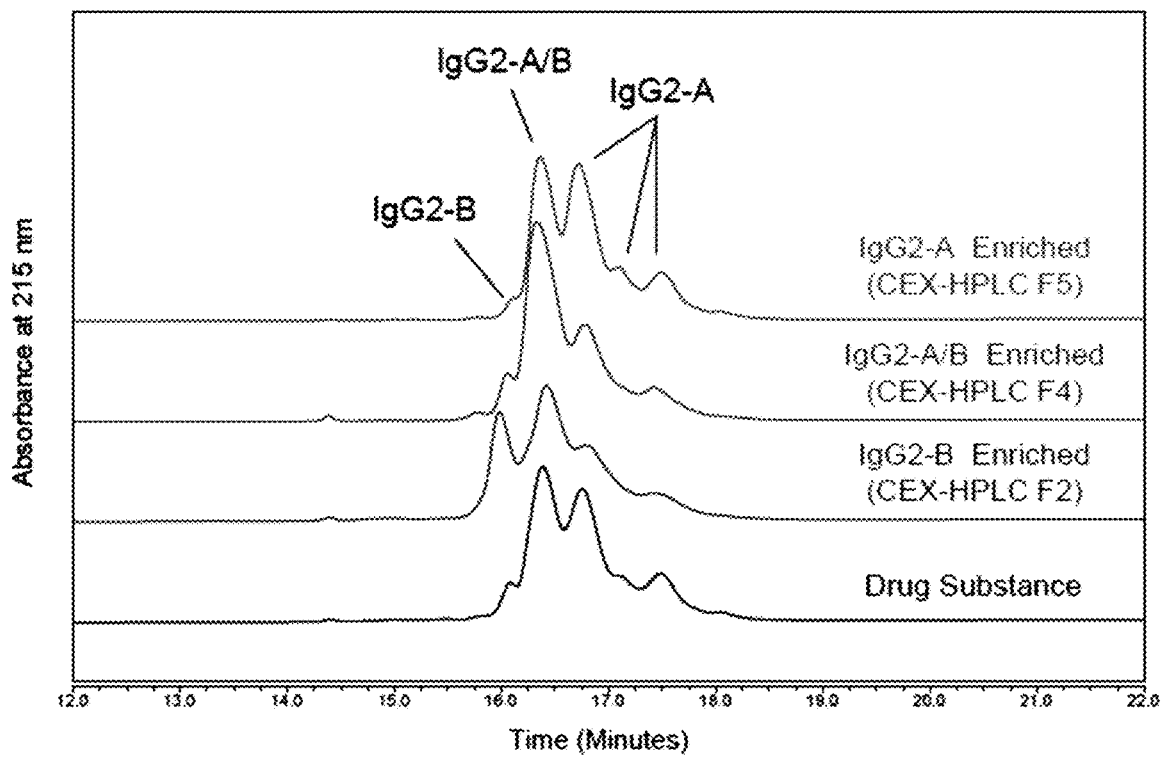
FIG. 16B is an overlay of RP-HPLC profiles of disulfide isoform variant-enriched CEX-HPLC fractions relative to erenumab drug substance. Erenumab drug substance and CEX-HPLC fractions were analyzed by RP-HPLC using a Waters BEH300 C4 column (1.7 μm particle size, 2.1 mm×50 mm) and eluted using a 0.1% TFA-containing mobile phase and a gradient of 1-propanol at 75° C. with detection at 215 nm.

Although non-reduced RP-HPLC is an effective method for determination of relative amounts of the disulfide isoform variants, the mobile phase and separation conditions are incompatible with the cell-based bioassay used to determine inhibitory potency of erenumab. Therefore, disulfide isoform enriched fractions were collected from semi-preparative CEX-HPLC as described in Example 3, and tested for potency using the cell-based bioassay described in Example 1. Three CEX-HPLC fractions, enriched in disulfide isoforms IgG2-A, IgG2-AB, and IgG2-B relative to drug substance (Table 16 and FIG. 13A), were analyzed for potency as described in more detail below. Enriched IgG2-A, IgG2-B, and IgG2-AB disulfide isoform CEX-HPLC fractions were analyzed by non-reduced RP-HPLC to confirm adequate purity prior to the potency evaluation. A RP-HPLC overlay of the three CEX-HPLC collected fractions relative to unfractionated drug substance is shown in FIG. 16B and the RP-HPLC disulfide isoform distribution data are provided in Table 20.

TABLE 20

Non-reduced RP-HPLC Relative Area % of CEX-HPLC Purified Fractions[1]

| IgG2 Isoform Enriched Sample | % Relative Area | | |
|---|---|---|---|
| (CEX-HPLC Fraction) | IgG2-B | IgG2-A/B | IgG2-A |
| IgG2-A (F5) | 2.9 | 33.9 | 62.4 |
| IgG2-A/B (F4) | 7.0 | 52.5 | 39.4 |
| IgG2-B (F2) | 21.4 | 40.4 | 35.8 |
| Drug Substance | 5.9 | 36.6 | 56.0 |

[1]All CEX-HPLC fractions were collected from the same drug substance lot. Purity of isoform of interest from each collected CEX-HPLC fraction emphasized and underlined.

As shown in Table 21, relative potency of the IgG2-A and IgG2-AB enriched isoform fractions are similar to the relative potency of erenumab drug substance. However, the fraction enriched for the IgG2-B disulfide isoform showed significantly reduced potency relative to the drug substance and the enriched IgG2-AB and IgG2-A isoform fractions.

TABLE 21

Potency of Erenumab Disulfide Isoforms

| Sample Description | % Relative Potency by Cell-Based Bioassay[1] | % CV |
|---|---|---|
| Drug Substance[2] | 91 | 13 |
| IgG2-B Enriched Fraction | 58 | 14 |

TABLE 21-continued

Potency of Erenumab Disulfide Isoforms

| Sample Description | % Relative Potency by Cell-Based Bioassay[1] | % CV |
|---|---|---|
| IgG2-A/B Enriched Fraction | 82 | 18 |
| IgG2-A Enriched Fraction | 101 | 16 |

[1]Average of 3 replicates
[2]Drug substance lot from which disulfide isoform enriched fractions were purified These data suggest that the structural conformation of the disulfide bonds in the hinge region of erenumab is important for the biological activity of the antibody. In particular, elevated levels of the IgG2-B disulfide isoform in the drug substance significantly impact the inhibitory potency. Analysis of several lots of erenumab drug substance manufactured at commercial scale revealed consistent levels of the IgG2-B disulfide isoform in drug substance, ranging from 4.6% to 5.2% as measured by non-reduced RP-HPLC. Levels of the IgG2-AB and IgG2-A disulfide isoforms in these erenumab drug substance lots were also consistent with IgG2-AB levels ranging from 34.2% to 35.5% and IgG2-A levels ranging from 57.4% to 59.3%.

Example 5. Identification and Characterization of Erenumab Size Variants

This example describes the identification and characterization of size variants of erenumab that exhibited reduced CGRP receptor inhibitory function. Size variants of erenumab can include high molecular weight (HMW) species and low molecular weight (LMW) species. HMW species, which are species larger than monomer (e.g. dimer and higher order oligomeric species), may be formed through non-covalent association, reducible covalent association, and/or non-reducible covalent association. LMW species can arise through fragmentation of the polypeptide backbone and/or incomplete assembly of subunit constituents, such as the light chain and heavy chain.

In this example, size heterogeneity of erenumab was evaluated by SE-UHPLC. SE-UHPLC separates proteins based primarily on differences in hydrodynamic volume. The SE-UHPLC method was performed under non-reducing, non-denaturing conditions to assess the size distribution of erenumab under native conditions. Samples of erenumab drug substance were loaded onto an analytical SE-UHPLC column (BEH200 column, 1.7 µm particle size, 4.6 mm×150 mm, Waters Corporation) and proteins were separated isocratically using a mobile phase comprising 100 mM sodium phosphate, 250 mM sodium chloride at pH 6.8. The eluent was monitored by UV absorbance at 280 nm. The column was operated at ambient temperature and the mobile phase was applied to the column at a flow rate of 0.4 mL/min.

Figure 17A:
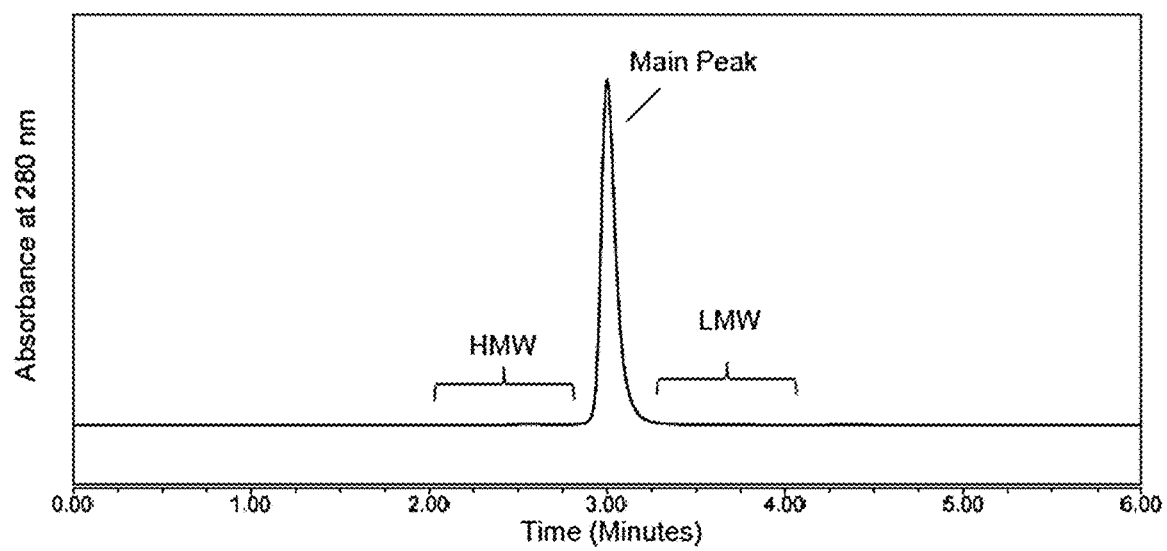
FIGS. 17A and 17B depict a representative SE-UHPLC profile of erenumab drug substance at full scale (FIG. 17A) and expanded scale (FIG. 17B). Erenumab drug substance was analyzed by SE-UHPLC using a 100 mM sodium phosphate, 250 mM sodium chloride, pH 6.8 mobile phase and detection at 280 nm absorbance. Buffer peak denoted with an asterisk (*).
Figure 17B:
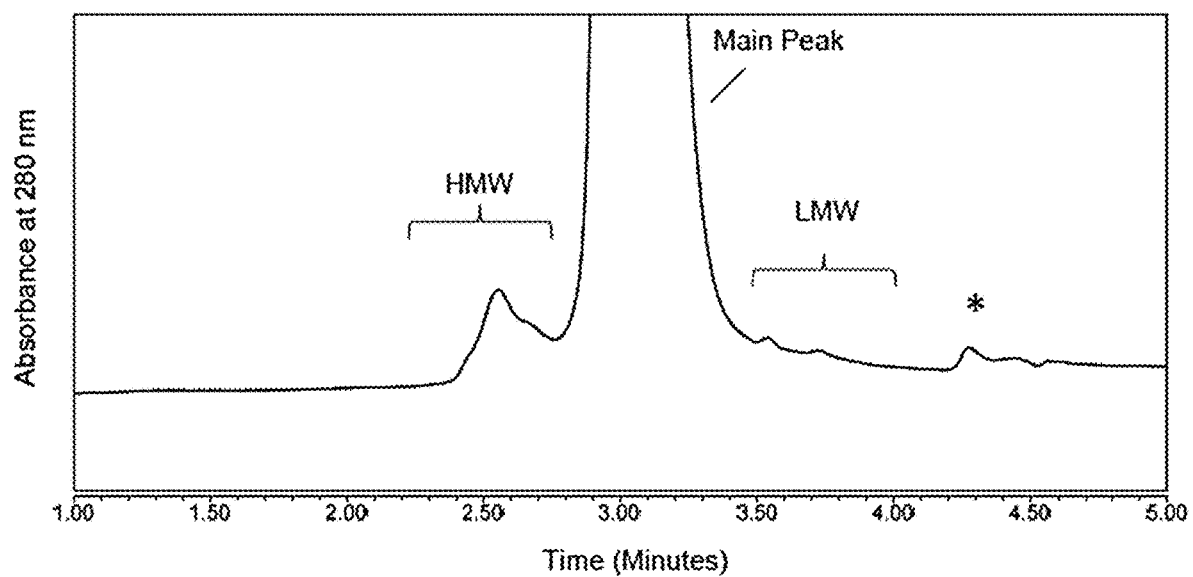
Figure 18A:
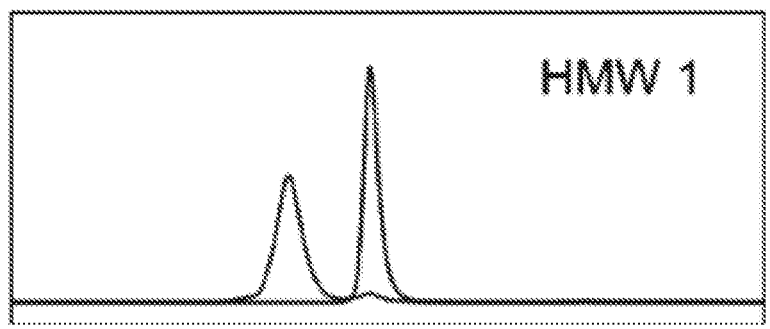
FIGS. 18A-18D show overlays of SE-UHPLC collected fractions and erenumab drug substance analyzed by SE-UHPLC. Erenumab drug substance and fractions collected from semi-preparative SE-HPLC (HMW1, HMW2, and Main.
Figure 18B:
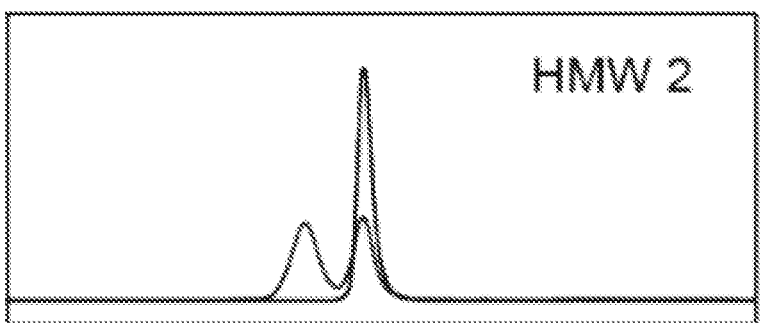
Figure 18C:
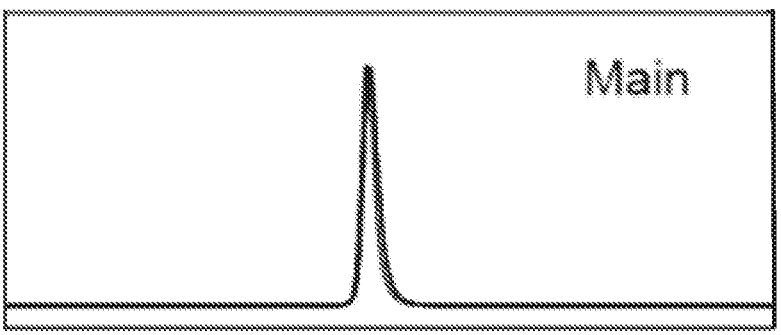
Figure 18D:
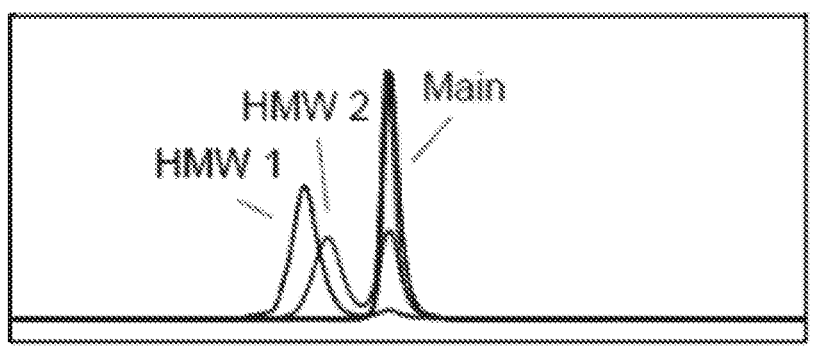

Three distinct regions were evident in the SE-UHPLC profile of erenumab drug substance, including a predominant monomer (main) peak and low levels of HMW (pre-peak) and LMW (post-peak) as shown in FIGS. 17A and 17B. Fractions from the pre-peak, main peak and post-peak regions were collected and the variants separated in the fractions were characterized. The HMW peak by SE-UHPLC (FIG. 17B) is comprised of two, incompletely resolved species and as such, was collected as two, separate fractions representing the leading and tailing edge of the HMW peak, respectively. The two HMW peaks and main peak were isolated using semi-preparative SE-HPLC, followed by further enrichment by analytical SE-HPLC. Collected HMW and main peak fractions were concentrated using a molecular weight cutoff filter and buffer exchanged into 15 mM sodium acetate, pH 5.2 prior to characterization analyses. The LMW peak group by SE-UHPLC (FIG. 17B) is comprised of two, small peaks, the sum of which is below the assay quantitation limit of 0.3% in drug substance. The LMW peak group was isolated and enriched using analytical SE-UHPLC and subjected to limited characterization testing as described in more detail below.

Characterization of SE-UHPLC HMW Fractions

The SE-UHPLC profiles and purities of the isolated HMW and main peak fractions, shown in FIGS. 18A-18D and Table 22, respectively, demonstrate that the fractions were of sufficient purity for characterization.

TABLE 22

SE-UHPLC Peak Area Percentage of Enriched Fractions[1]

| Sample Description | % HMW | % Main Peak | % LMW |
|---|---|---|---|
| Drug Substance | 0.5 | 99.2 | <0.3[2] |
| SE-UHPLC Fraction HMW 1 | 93.9 | 6.1 | <0.3[2] |
| SE-UHPLC Fraction HMW 2 | 53.9 | 45.9 | <0.3[2] |
| SE-UHPLC Fraction Main | <0.3[2] | 99.7 | <0.3[2] |

[1]All SE-UHPLC fractions were collected from the same drug substance lot.
[2]LOQ = 0.3%

The enriched HMW and main peak fractions in FIGS. 18A-18D and Table 22 were characterized by various analytical techniques, including SE-UHPLC with static light scattering detection, reduced sodium dodecyl sulfate capillary electrophoresis (rCE-SDS), non-reduced sodium dodecyl sulfate capillary electrophoresis (nrCE-SDS), and a cell-based bioassay.

The HMW and main peak fractions along with the non-fractionated drug substance were analyzed by SE-HPLC with static light scattering detection (SE-HPLC-SLS) to determine the molar mass of the dominant peaks in each chromatogram. The SE-HPLC-SLS analysis was performed using an Agilent 1100 HPLC system. The column was a TSK-GEL G3000SWxl, 5 µm particle size, 7.8 mm ID×300 mm length column (Tosoh Biosep). The detectors used were a Wyatt Heleos II light scattering detector, a Wyatt Optilab rEX RI detector, and an Agilent UV detector with wavelength set at 280 nm. The SE-HPLC runs were performed at room temperature, with 100 mM potassium phosphate, 250 mM potassium chloride, pH 6.8 buffer used as the mobile phase and the flow rate was 0.5 mL/min. Injection volumes were 4.3 µL to inject 300 µg of protein. For molecular weight (MW) calculation, LS (light scattering) and RI (refractive index) signals and a sample refractive increment (dn/dc) value of 0.185 were used.

The measured mass of monomer (intact antibody comprising 2 heavy chains and 2 light chains) from the main peak fraction was 149 kDa and from the drug substance control was 143 kDa, both of which are consistent with the theoretical molecular mass of erenumab monomer (148.8 kDa)(Table 23). The measured masses of the HMW peak for both HMW enriched fractions (HMW 1 and HMW 2) were 292 kDa and 279 kDa, respectively, both of which are consistent with the molecular mass for the erenumab dimer (297.6 kDa)(Table 23). These data demonstrate that both the HMW 1 and HMW 2 enriched fractions are predominantly comprised of erenumab dimer.

TABLE 23

SE-HPLC-SLS Measured Molar Mass of Enriched HMW and Main Peak Fractions

| Sample Description | % HMW | MW of HMW (kDa) | % Main Peak | MW of Main (kDa) |
|---|---|---|---|---|
| Drug Substance | 0.6 | 297 | 97.4 | 143 |
| SE-UHPLC Fraction HMW 1 | 93.1 | 292 | 6.9 | 210 |
| SE-UHPLC Fraction HMW 2 | 76.2 | 279 | 23.8 | 178 |
| SE-UHPLC Fraction Main | 0.4 | ND | 99.6 | 149 |

Analysis of the enriched fractions and unfractionated drug substance by nrCE-SDS according to the method described in Example 3 revealed that both HMW fractions are enriched in post-peaks, corresponding to covalent high molecular weight species larger than monomer (main peak), and have pre-peak areas comparable to the control (Table 24).

TABLE 24 nrCE-SDS Peak Area Percentage of Enriched SE-UHPLC Fractions[1]

| Sample Description | % Pre-peaks | % Main Peak | % Post-peaks |
|---|---|---|---|
| Drug Substance | 2.7 | 97.3 | 0.0 |
| SE-UHPLC Fraction HMW 1 | 4.3 | 31.4 | 64.3 |
| SE-UHPLC Fraction HMW 2 | 5.1 | 39.9 | 54.9 |
| SE-UHPLC Fraction Main | 2.7 | 97.3 | 0.0 |

[1]All SE-UHPLC fractions were collected from the same drug substance lot.

The proportions of non-covalent and covalent dimers can be approximated by comparing the purity of the enriched fractions under native conditions to those under denaturing conditions. In comparing the level of dimer under native conditions (SE-UHPLC: % HMW in Table 22) to the level of covalent-dimer under denaturing conditions (nrCE-SDS: % post-peaks in Table 24), the level of covalent dimer can be estimated in the native drug substance. Based on this comparison, a majority of the native dimer species in erenumab drug substance are covalent with approximately 68% of the HMW 1 dimer species and nearly all of the HMW 2 dimer remaining under denaturing testing conditions.

Figure 19:
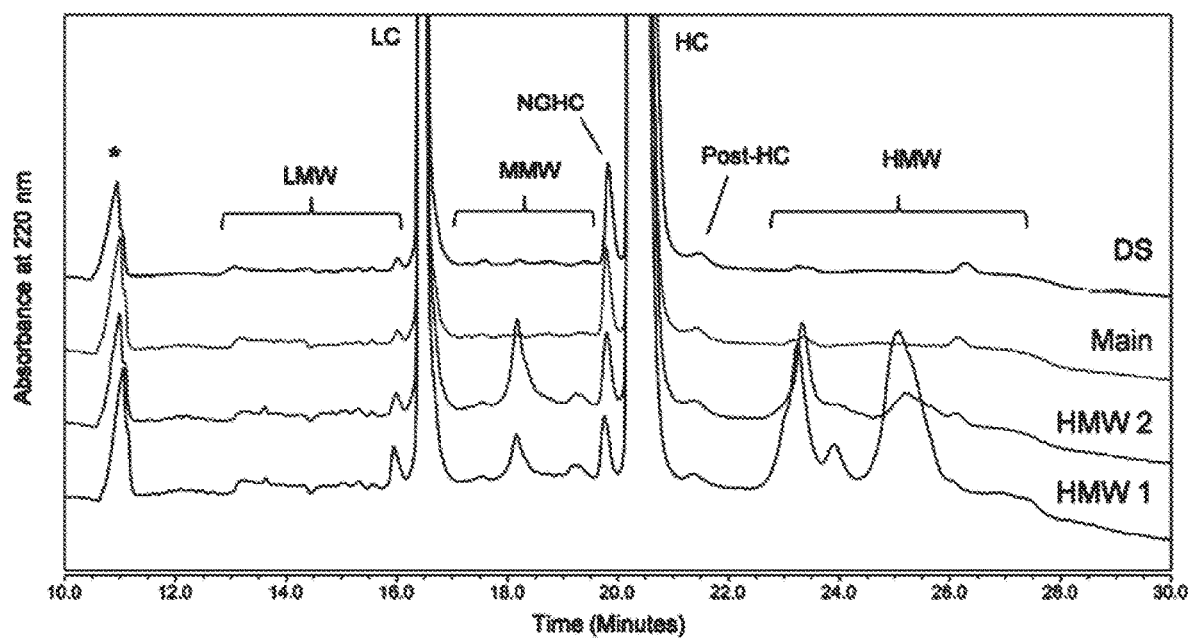
FIG. 19 is an rCE-SDS profile of SE-UHPLC collected fractions and erenumab drug substance at expanded scale. Erenumab drug substance (DS) and the SE-UHPLC fractions (Main, HMW1, HMW2) were denatured and reduced prior to electrokinetic injection into a bare-fused silica capillary filled with SDS gel buffer at 25° C. Absorbance was monitored at 220 nm. System peak is denoted with an asterisk (*). LMW=low molecular weight species; MMW=middle molecular weight species; HMW=high molecular weight species; LC=light chain; HC=heavy chain; NGHC=non-glycosylated heavy chain; post-HC=post heavy chain.

The erenumab drug substance and enriched HMW species and main peak fractions were also analyzed by rCE-SDS according to the method described in Example 3. As shown in FIG. 19, the results of the rCE-SDS analysis showed that both HMW 1 and HMW 2 fractions are enriched in middle molecular weight (MMW) and high molecular weight (HMW) species relative to the drug substance. Similar to the assessment of the level of covalent and non-covalent dimer species, rCE-SDS can be used to approximate the level of reducible and non-reducible dimer species in drug substance. In comparing the level of dimer under native conditions (SE-UHPLC: % HMW) to the level of non-reducible dimer under reducing and denaturing conditions (rCE-SDS: % HMW), the level of non-reducible dimer can be estimated in the native drug substance. Based on the comparison as shown in Table 25, a majority of the native dimer species in erenumab drug substance are reducible with approximately 87% of the HMW 1 dimer species and approximately 93% of the HMW 2 dimer species reducing to individual components under reducing and denaturing conditions.

TABLE 25

Estimation of the Levels of Reducible and Non-reducible Dimer in Erenumab Drug Substance (DS)

| Sample Description | % HMW by SE-UHPLC | % HMW by rCE-SDS | % Reducible Dimer in Starting DS | % Non-reducible Dimer in Starting DS |
|---|---|---|---|---|
| SE-UHPLC Fraction HMW 1 | 93.9 | 12.5 | 87 | 13 |
| SE-UHPLC Fraction HMW 2 | 53.9 | 3.8 | 93 | 7 |

The biological activity of the enriched SE-UHPLC fractions compared to erenumab drug substance was evaluated by the cell-based bioassay described in Example 1. As shown in Table 26, both the HMW 1 and HMW 2 enriched fractions exhibited reduced potency relative to the drug substance and to the enriched main peak. A significant portion of the HMW species in these fractions is covalently linked and non-dissociable as described above. Self-association imposes steric constraints that may result in conformational changes, which in turn may affect binding of the molecule to the CGRP receptor target, thereby explaining the reduced potency observed.

TABLE 26

Potency of Enriched SE-UHPLC Fractions

| Sample Description | % Relative Potency by Cell-Based Bioassay[1] | % CV |
|---|---|---|
| Drug Substance | 96 | 2 |
| SE-UHPLC Fraction HMW 1 | 42 | 7 |
| SE-UHPLC Fraction HMW 2 | 62 | 6 |
| SE-UHPLC Fraction Main | 97 | 4 |

[1]Average of 3 replicates

Characterization of SE-UHPLC LMW Fraction

The LMW peaks (FIG. 17B) were collected by SE-UHPLC in a single fraction and concentrated using a molecular weight cutoff filter prior to characterization analyses. Re-injection of the LMW fraction on SE-UHPLC showed enrichment of the LMW species to approximately 34.4% (data not shown). The collected, enriched LMW fraction was analyzed by whole mass analysis under non-reducing conditions to characterize the nature of the LMW species.

The mass of the enriched LMW fraction was determined by mass spectrometric analysis under native, non-reducing conditions using RP-HPLC coupled to an electrospray ionization time of flight mass spectrometry. The results from the analysis indicate that the collected LMW fraction is enriched in covalently-linked light chain dimer (LC-LC) relative to the non-fractionated drug substance.

The results of the analyses described in this example show that erenumab was shown to exist primarily in its expected monomeric form as an intact antibody comprising 2 heavy chains and 2 light chains (approximately 99.2% of drug substance) by SE-UHPLC under non-denaturing conditions. The remaining portion consists of HMW species (0.5% of drug substance) made up primarily of dimer as well as trace levels of LMW species. No higher order oligomers were observed. SE-UHPLC fractions of eruenamb drug substance enriched in HMW species exhibited reduced inhibitory potency relative to the monomeric form of erenumab.

Erenumab dimer is comprised primarily of covalently-linked monomer subunits and does not dissociate under denaturing conditions. The majority of dimer is reducible, converting to heavy and light chain components under reducing and denaturing conditions and are therefore associated through disulfide bonding. Non-reducible species are present as a minor component of covalent dimer, migrating after the heavy chain peaks by rCE-SDS. Characterization of the SE-UHPLC LMW peak showed the peak to be enriched in light chain dimer.

Several lots of erenumab drug substance (140 mg/mL) manufactured at commercial scale were analyzed by SE-UHPLC to assess the presence and quantity of size variants (e.g. HMW and LMW species) as measured by the peak area percentage of the HMW and LMW peaks in the SE-UHPLC chromatogram. Potency of the drug substance lots was also evaluated by the cell-based potency assay and compared to the potency of Lot No. 78137, which is representative of the erenumab drug substance employed in Phase II/Phase III clinical trials. A summary of the data is provided in Table 27 below.

TABLE 27

SE-UHPLC and Potency Data for Erenumab Drug Substance Lots

| Lot Number | SE-UHPLC | | | Cell-Based Bioassay % Relative Potency |
|---|---|---|---|---|
| | % Main Peak | % HMW | % LMW | |
| 78137 (clinical trial material) | — | — | — | 101 |
| 63130 | 99.2 | 0.6 | <0.3 | 98 |
| 63131 | 99.2 | 0.6 | <0.3 | 124 |
| 63132 | 99.3 | 0.6 | <0.3 | 92 |
| 63133 | 99.3 | 0.6 | <0.3 | 96 |
| 63134 | 99.2 | 0.6 | <0.3 | 101 |

As shown by the data in Table 27, erenumab drug substance manufactured at commercial scale contained a consistent level of about 0.6% HMW species as measured by SE-UHPLC. Drug substance that contained this level of HMW species exhibited a potency that was comparable to the potency of the erenumab drug substance employed in clinical trials.

Three of the drug substance batches from Table 27 (63131, 63132, and 63133) were stored for three months at 25° C. and samples were subject to SE-UHPLC analysis and potency testing to assess any impact on drug substance potency due to change in levels of size variants over time. The results of this stability study are shown in Table 28.

TABLE 28

SE-UHPLC and Potency Data for Erenumab Drug Substance Lots Stored at 25° C.

| Lot Number | SE-UHPLC at 3 Months | | | Cell-Based Bioassay at 3 Months % Relative Potency |
|---|---|---|---|---|
| | % Main Peak | % HMW | % LMW | |
| 63131 | 98.3 | 1.4 | 0.3 | 90 |
| 63132 | 98.2 | 1.5 | 0.3 | 94 |
| 63133 | 98.1 | 1.6 | 0.3 | 86 |

Drug substance that contained levels of HMW species as high as 1.6% had a comparable potency to erenumab drug substance employed in clinical trials.

To evaluate the susceptibility of erenumab to form size variants under thermal stress conditions, erenumab drug substance was incubated at 50° C. for 14 days. Samples were removed at various time points over the duration of the study and frozen. After the final time point, all samples were analyzed side-by-side to minimize analytical variability. The samples were assessed by SE-UHPLC according to the method described above and by the cell-based bioassay described in Example 1.

Figure 20:
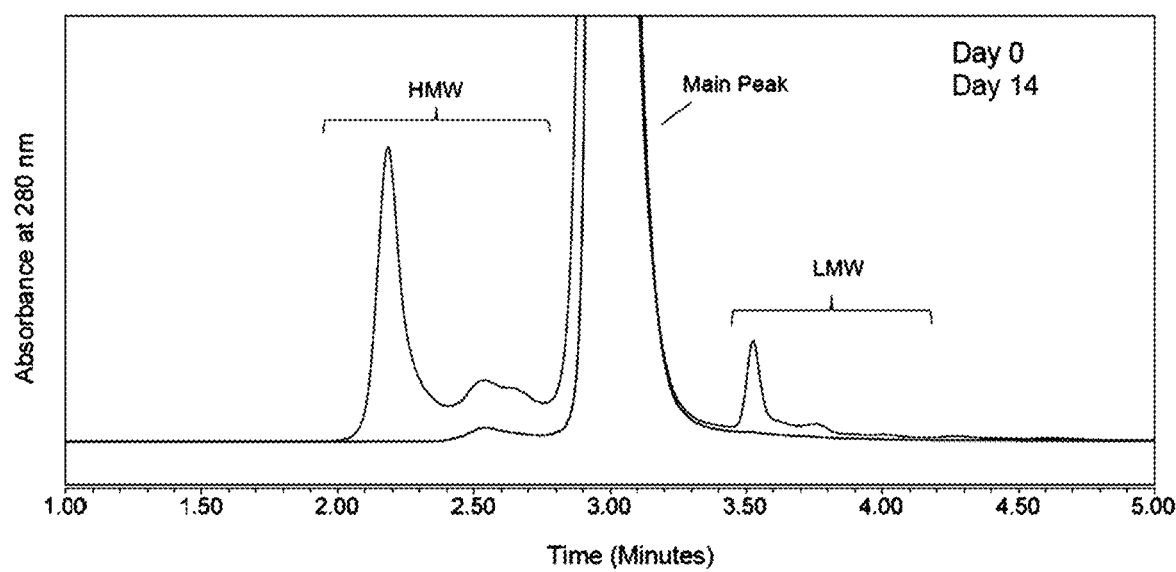
FIG. 20 is a SE-UHPLC profile of erenumab drug substance exposed to thermal stress. Erenumab drug substance incubated at 50° C. for up to 14 days was analyzed by SE-UHPLC using a 100 mM sodium phosphate, 250 mM sodium chloride, pH 6.8 mobile phase and detection at 280 nm absorbance. The top trace corresponds to the Day 14 time point.

The native SE-UHPLC profiles of day 0 and day 14 samples of erenumab drug substance stressed at 50° C. are shown in FIG. 20. The relative peak area % for the peaks shown in FIG. 20 are presented in Table 29 along with the % relative potency of the samples as evaluated by the cell-based bioassay. HMW species were the predominant degradant displaying an increase over 14 days with a corresponding decrease in main peak. The HMW species generated were predominantly comprised of higher order aggregates (HMW species greater than dimer). There was also an increase in LMW species observed at day 14. The thermally stressed sample of erenumab drug substance exhibited significantly reduced potency. The reduced potency was primarily due to the increase in HMW species as well as the increase in $Asp^{105}$ isomerization variants, which were also elevated in thermally stressed samples of erenumab drug substance (see Example 2).

TABLE 29

SE-UHPLC Peak Area % and Relative Potency of Erenumab Stressed at 50° C.

| Time Point (Days) | % HMW | % Main Peak | % LMW | % Relative Potency by Cell-Based Bioassay[1] (% CV) |
|---|---|---|---|---|
| 0 | 0.5 | 99.1 | 0.4 | 93 (4) |
| 14 | 9.6 | 88.2 | 2.2 | 71 (7) |

[1]Average of 3 replicates

Further thermal stress studies were conducted on additional erenumab drug substance batches manufactured at commercial scale. Three of the drug substance batches from Table 27 (63131, 63132, and 63133) were stored for up to 30 days at 40° C. and samples were subject to SE-UHPLC analysis and cell-based potency testing to further assess any impact on drug substance potency due to change in levels of size variants over time. The results of this thermal stress study are shown in Table 30.

TABLE 30

SE-UHPLC and Potency Data for Erenumab Drug Substance Lots Stored at 40° C.

| Lot Number | Days at 40° C. | SE-UHPLC | | | Cell-Based Bioassay |
| | | % Main Peak | % HMW | % LMW | % Relative Potency |
|---|---|---|---|---|---|
| 63131 | 14 | 97.0 | 2.3 | 0.7 | 91 |
| 63131 | 30 | 95.6 | 3.4 | 1.0 | 83 |
| 63132 | 14 | 97.0 | 2.3 | 0.7 | 96 |
| 63132 | 30 | 94.7 | 4.2 | 1.1 | 96 |
| 63133 | 14 | 96.9 | 2.4 | 0.7 | 91 |
| 63133 | 30 | 95.1 | 3.8 | 1.1 | 76 |

The results of this study show a general trend of a reduction in potency with an increase in HMW and LMW species. In particular, levels of HMW species greater than about 2.5% in drug substance were associated with a reduction in potency of the drug substance. It is noted that the 30 day sample of the 63132 lot did not show a reduction in potency, however, this is likely due to the variability of the cell-based bioassay.

All publications, patents, and patent applications discussed and cited herein are hereby incorporated by reference in their entireties. It is understood that the disclosed invention is not limited to the particular methodology, protocols and materials described as these can vary. It is also understood that the terminology used herein is for the purposes of describing particular embodiments only and is not intended to limit the scope of the appended claims.

Those skilled in the art will recognize, or be able to ascertain using no more than routine experimentation, many equivalents to the specific embodiments of the invention described herein. Such equivalents are intended to be encompassed by the following claims.

What is claimed:

1. A composition comprising:
   erenumab, wherein erenumab comprises two heavy chains and two light chains, each said heavy chain having a sequence of SEQ ID NO: 1 or SEQ ID NO: 3 and each said light chain having a sequence of SEQ ID NO: 2 or SEQ ID NO: 4;
   (ii) an erenumab isomerization variant, wherein the isomerization variant has an isoaspartic acid residue or a succinimide at amino acid position 105 in either or both heavy chains of erenumab; and
   (iii) an erenumab deamidation variant, wherein the deamidation variant has an aspartic acid residue, a succinimide, or an isoaspartic acid residue at amino acid position 102 in either or both heavy chains of erenumab, and
   wherein the amount of the isomerization variant and deamidation variant in the composition is from about 1% to about 15%.

2. The composition of claim 1, wherein the amount of the isomerization variant and deamidation variant in the composition is from about 1% to about 10%.

3. The composition of claim 1, wherein the amount of the isomerization variant and deamidation variant in the composition is from about 1% to about 4%.

4. The composition of claim 1, wherein the amount of the isomerization variant and deamidation variant in the composition is determined by hydrophobic interaction chromatography high performance liquid chromatography (HIC-HPLC).

5. The composition of claim 1, wherein each heavy chain of erenumab has the sequence of SEQ ID NO: 3 and each light chain of erenumab has the sequence of SEQ ID NO: 4, and wherein the amount of erenumab in the composition is about 90% or greater as measured by the main peak in HIC-HPLC and the amount of the isomerization variant and deamidation variant in the composition is from about 1% to about 10% as measured by the pre-peaks in HIC-HPLC.

6. The composition of claim 1, wherein each heavy chain of erenumab has the sequence of SEQ ID NO: 1 and each light chain of erenumab has the sequence of SEQ ID NO: 2.

7. The composition of claim 1, wherein each heavy chain of erenumab has the sequence of SEQ ID NO: 3 and each light chain of erenumab has the sequence of SEQ ID NO: 4.

8. A pharmaceutical formulation comprising the composition of claim 1 and one or more pharmaceutically acceptable excipients.

9. A composition comprising an erenumab IgG2-A isoform, an erenumab IgG2-AB isoform, and an erenumab IgG2-B isoform, wherein each erenumab isoform comprises two heavy chains and two light chains, each said heavy chain having a sequence of SEQ ID NO: 1 or SEQ ID NO: 3 and each said light chain having a sequence of SEQ ID NO: 2 or SEQ ID NO: 4; wherein:
   (i) the amount of the IgG2-A isoform in the composition is from about 52% to about 66%:
   (ii) the amount of the IgG2-AB isoform in the composition is from about 32% to about 38%; and
   (iii) the amount of the IgG2-B isoform in the composition is from about 1% to about 10%.

10. The composition of claim 9, wherein:
    (i) the amount of the IgG2-A isoform in the composition is from about 56% to about 60%;
    (ii) the amount of the IgG2-AB isoform in the composition is from about 34% to about 37%; and
    (iii) the amount of the IgG2-B isoform in the composition is from about 4% to about 8%.

11. The composition of claim 9, wherein the amount of each erenumab isoform in the composition is determined by non-reduced reversed phase high performance liquid chromatography (RP-HPLC).

12. The composition of claim 9, wherein each heavy chain of erenumab has the sequence of SEQ ID NO: 1 and each light chain of erenumab has the sequence of SEQ ID NO: 2.

13. The composition of claim 9, wherein each heavy chain of erenumab has the sequence of SEQ ID NO: 3 and each light chain of erenumab has the sequence of SEQ ID NO: 4.

14. A pharmaceutical formulation comprising the composition of claim 9 and one or more pharmaceutically acceptable excipients.

15. A pharmaceutical formulation comprising 70 mg/mL of an erenumab composition, about 25 mM acetate, about 7.3% (w/v) sucrose, and about 0.010% (w/v) polysorbate 80, wherein the formulation has a pH of about 5.2±0.2, wherein the erenumab composition comprises erenumab and one or more erenumab variants, wherein erenumab comprises two heavy chains and two light chains, each said heavy chain having a sequence of SEQ ID NO: 1 or SEQ ID NO: 3 and each said light chain having a sequence of SEQ ID NO: 2 or SEQ ID NO: 4, wherein the erenumab variants comprise isomerization variants, deamidation variants, acidic variants, HMW species, or combinations thereof, and wherein the composition has all of the following characteristics:
  (a) the amount of acidic variants in the composition is from about 25% to about 38% as measured by cation exchange high performance liquid chromatography (CEX-HPLC);
  (b) the amount of HMW species in the composition is about 2.1% or less as measured by size exclusion ultra-high performance liquid chromatography (SE-UHPLC); and
  (c) the amount of isomerization variants and deamidation variants in the composition is about 8% or less as measured by the pre-peaks in HIC-HPLC.

16. A pre-filled syringe or autoinjector comprising the pharmaceutical formulation of claim 15.

17. The pre-filled syringe or autoinjector of claim 16, wherein the injection volume of the syringe or autoinjector is about 1 mL.

18. A pharmaceutical formulation comprising 140 mg/mL of an erenumab composition, about 34 mM acetate, about 6.5% (w/v) sucrose, and about 0.010% (w/v) polysorbate 80, wherein the formulation has a pH of about 5.2±0.2, wherein the erenumab composition comprises erenumab and one or more erenumab variants, wherein erenumab comprises two heavy chains and two light chains, each said heavy chain having a sequence of SEQ ID NO: 1 or SEQ ID NO: 3 and each said light chain having a sequence of SEQ ID NO: 2 or SEQ ID NO: 4, wherein the erenumab variants comprise isomerization variants, deamidation variants, acidic variants, HMW species, or combinations thereof, and wherein the composition has all of the following characteristics:
  (a) the amount of acidic variants in the composition is from about 25% to about 38% as measured by CEX-HPLC;
  (b) the amount of HMW species in the composition is about 2.1% or less as measured by SE-UHPLC; and
  (c) the amount of isomerization variants and deamidation variants in the composition is about 8% or less as measured by the pre-peaks in HIC-HPLC.

19. A pre-filled syringe or autoinjector comprising the pharmaceutical formulation of claim 18.

20. The pre-filled syringe or autoinjector of claim 19, wherein the injection volume of the syringe or autoinjector is about 1 mL.

21. A pharmaceutical formulation comprising an erenumab composition, wherein the pharmaceutical formulation is prepared by a method comprising:
  (i) obtaining a partially purified composition comprising erenumab and erenumab isomerization and deamidation variants, wherein erenumab comprises two heavy chains and two light chains, each said heavy chain having a sequence of SEQ ID NO: 1 or SEQ ID NO: 3 and each said light chain having a sequence of SEQ ID NO: 2 or SEQ ID NO: 4;
  (ii) measuring the amount of the isomerization and deamidation variants in the partially purified composition using HIC-HPLC, wherein the isomerization variant has an isoaspartic acid residue or a succinimide at amino acid position 105 in either or both heavy chains of erenumab and the deamidation variant has an aspartic acid residue, a succinimide, or an isoaspartic acid residue at amino acid position 102 in either or both heavy chains of erenumab;
  (iii) comparing the measured amount of the isomerization and deamidation variants to a pre-determined reference criterion, wherein the pre-determined reference criterion is a range from about 1% to about 10%; and
  (iv) combining the erenumab composition with one or more excipients to prepare the pharmaceutical formulation if the comparison indicates that the pre-determined reference criterion is met.

22. The pharmaceutical formulation of claim 21, wherein if the comparison in step (iii) indicates that the pre-determined reference criterion is not met, the method further comprises subjecting the erenumab composition to hydrophobic interaction chromatography to reduce the amount of the isomerization and deamidation variants to meet the pre-determined reference criterion to produce a reprocessed erenumab composition and subsequently combining the reprocessed erenumab composition with one or more excipients to prepare the pharmaceutical formulation.

23. The pharmaceutical formulation of claim 21, wherein the partially purified composition is a cell culture harvest from a Chinese Hamster Ovary cell line that recombinantly expresses a nucleic acid encoding a heavy chain of SEQ ID NO: 1 and a nucleic acid encoding a light chain of SEQ ID NO: 2.

24. The pharmaceutical formulation of claim 21, wherein the partially purified composition is an elution pool from a cation exchange chromatography material.

25. The pharmaceutical formulation of claim 21, wherein the pre-determined reference criterion is a range from about 1% to about 4%.

26. The pharmaceutical formulation of claim 21, wherein each heavy chain of erenumab has the sequence of SEQ ID NO: 3 and each light chain of erenumab has the sequence of SEQ ID NO: 4.

27. The pharmaceutical formulation of claim 21, wherein the one or more excipients combined with the erenumab composition include acetate, sucrose, and polysorbate.

* * * * *